US011484567B2

(12) United States Patent
Bahrami et al.

(10) Patent No.: US 11,484,567 B2
(45) Date of Patent: Nov. 1, 2022

(54) USE OF IMMUNE SUPPRESSIVE DOMAINS AS MEDICAMENTS

(71) Applicants: iSD Immunotech ApS, Copenhagen N (DK); Aarhus Universitet, Aarhus C (DK)

(72) Inventors: Shervin Bahrami, Aarhus C (DK); Mogens Ryttergård Duch, Risskov (DK); Christian Kanstrup Holm, Lystrup (DK); Magdalena Janina Laska, Aarhus C (DK)

(73) Assignees: Aarhus Universitet, Aarhus N (DK); iSD Immunotech ApS, Copenhagen C (DK)

( * ) Notice: Subject to any disclaimer, the term of this patent is extended or adjusted under 35 U.S.C. 154(b) by 553 days.

(21) Appl. No.: 14/783,286

(22) PCT Filed: Apr. 10, 2014

(86) PCT No.: PCT/DK2014/050091
§ 371 (c)(1),
(2) Date: Oct. 8, 2015

(87) PCT Pub. No.: WO2014/166502
PCT Pub. Date: Oct. 16, 2014

(65) Prior Publication Data

US 2016/0175387 A1 Jun. 23, 2016

(30) Foreign Application Priority Data

Apr. 10, 2013 (DK) ........................... PA 2013 70200
Apr. 10, 2013 (DK) ........................... PA 2013 70202
Apr. 11, 2013 (DK) ........................... PA 2013 70204

(51) Int. Cl.

| | |
|---|---|
| *A61K 38/16* | (2006.01) |
| *A61K 38/00* | (2006.01) |
| *A61K 39/00* | (2006.01) |
| *A61K 39/12* | (2006.01) |
| *A61K 45/06* | (2006.01) |
| *C12N 7/00* | (2006.01) |

(52) U.S. Cl.
CPC ........ *A61K 38/162* (2013.01); *A61K 39/0008* (2013.01); *A61K 39/12* (2013.01); *A61K 45/06* (2013.01); *C12N 7/00* (2013.01); *A61K 38/00* (2013.01); *A61K 39/00* (2013.01); *C12N 2760/14033* (2013.01); *C12N 2760/16133* (2013.01); *C12N 2760/16233* (2013.01); *C12N 2760/16333* (2013.01); *C12N 2770/20033* (2013.01); *Y02A 50/30* (2018.01)

(58) Field of Classification Search
CPC ...... A61K 38/162; A61K 45/06; A61K 38/10; A61K 39/145; C12N 2760/16011
See application file for complete search history.

(56) References Cited

U.S. PATENT DOCUMENTS 9,631,018 B2 * 4/2017 Noelle ............. C07K 14/70503
2007/0185025 A1 * 8/2007 Palacios ............ G01N 33/5047
424/218.1

FOREIGN PATENT DOCUMENTS

| | | |
|---|---|---|
| WO | 2001/019380 | 3/2001 |
| WO | 2009/033786 | 3/2009 |
| WO | 2009/065618 | 5/2009 |
| WO | 2013/050048 | 4/2013 |

OTHER PUBLICATIONS

Lambert, Influenza Vaccines for the Future, N Engl J Med 2010; 363:2036-44 (Year: 2010).*
Julkunen, Inflammatory responses in influenza A virus infection, Vaccine 2001, 19: S32-S37 (Year: 2001).*
Cross, Composition and Functions of the Influenza Fusion Peptide, Protein & Peptide Letters, 2009, 16, 766-778 (Year: 2009).*
Holvast, Influenza vaccination in systemic lupus erythematosus: Safe and protective?, Autoimmunity Reviews 2007, 6: 300-305 (Year: 2007).*
National Institutes of Health, "Autoimmune disorders", Medline Plus, updated 2020, obtained from //medlineplus.gov/ency/article/000816.htm; (Year: 2020).*
Harvard Medical School, "What's the deal with autoimmune disease?", Harvard Health Publishing, 2018 (Year: 2018).*
Stojanovich et al., "Stress as a trigger of autoimmune disease", Autoimmunity Reviews, 2008, pp. 209-213 (Year: 2008).*
Ground-breaking discovery finds new link between autoimmune diseases and a gut bacterium (Oct. 29, 2018) retrieved Aug. 29, 2020 from https://medicalxpress.com/news/2018-10-ground-breaking-discovery-link-autoimmune-diseases.html; (Year: 2018).*
Centers for Disease Control and Prevention, "Systemic Lupus Erythematosus (SLE)", 2018; retrieved from https://www.cdc.gov/lupus/facts/detailed.html (Year: 2018).*
Demirkaya et al., "New Horizons in the Genetic Etiology of Systemic Lupus Erythematosus and Lupus-like Disease: Monogenic Lupus and Beyond", Journal of Clinical Medicine, 2020, pp. 1-20 (Year: 2020).*
Scherer et al., "The etiology of rheumatoid arthritis", Journal of Autoimmunity, 2020; pp. 1-15 (Year: 2020).*
Martinez et al., "Comparative virology of HTLV-1 and HTLV-2", Retrovirology, 2019, pp. 1-19 (Year: 2019).*
Garcia-Montojo, "Human endogenous retrovirus-K (HML-2): a comprehensive review", Critical Reviews in Microbiology, 2018, pp. 715-738 (Year: 2016).*
Cianciolo G.J., et al., "Human retrovirus-related synthetic peptides inhibit T lymphocyte proliferation", Immunology Letters, vol. 19, 1988, pp. 7-14.
Denner J, et al., "The immunosuppressive peptide of HIV-1: functional domains and immune response in AIDS patients", AIDS, vol. 8, 1994, pp. 1063-1072.

(Continued)

*Primary Examiner* — Lianko G Garyu
(74) *Attorney, Agent, or Firm* — Verrill Dana, LLP

(57) ABSTRACT

The present invention concerns uses of immune suppressive domains. In particular, the present invention concerns a use of an immune suppressive domain (ISD) for immune suppression and for reduction of inflammation.

22 Claims, 15 Drawing Sheets

Specification includes a Sequence Listing.

(56) References Cited

OTHER PUBLICATIONS

Harrell R.A., et al., "Suppression of the respiratory burst of human monocytes by a synthetic peptide homologous to envelope proteins of human and animal retroviruses", J Immunol., vol. 136, 1986, pp. 3517-3520.
Kleinerman E.S., et al., "A synthetic peptide homologous to the envelope proteins of retroviruses inhibits monocyte-mediated killing by inactivating interleukin 1", J Immunol., vol. 139, 1987, pp. 2329-2337.
Mangeney M. and Heidmann T., "Tumor cells expressing a retroviral envelope escape immune rejection in vivo", Proceedings of the National Academy of Sciences of the United Statesof America, vol. 95, No. 25, Dec. 8, 1998, pp. 14920-14925.
Haraguchi S, et al., "Induction of ii ill acellular cAMP by a synthetic retroviral envelope peptide: a possible mechanism of immunopathogenesis in retroviral infections", Proceedings of the National Academy of Sciences of the United States of America, vol. 92, No. 12, Jun. 6, 1995, pp. 5568-5571.
Haraguchi S., et al., "Differential modulation of Th1-and Th2-related cytokine mRNA expression by a synthetic peptide homologous to a conserved domain within retroviral envelope protein" Proceedings of the National Academy of Sciences of the United States of America, vol. 92, Apr. 1995, pp. 3611-3615.
Haraguchi S., et al., "A potent immunosuppressive retroviral peptide: cytokine patterns and signaling pathways", Immunol. Res., vol. 41, No. 1, May 1, 2008, pp. 46-55.
Mangeney, M., et al. "Placental syncytins: Genetic disjunction between the fusogenic and immunosuppressive activity of retroviral envelope proteins", Proceedings of the National Academy of Sciences of the United States of America, vol. 104, No. 51, Dec. 18, 2007, pp. 20534-20539.
Sander, H.M., et al., "The annual cost of psoriasis", J. Am. Acad. Dermatol., vol. 28, 1993, pp. 422-425.
Funding, A.T., et al., "Reduced oxazolone-induced skin inflammation in MAPKAP kinase 2 knockout mice", J. Invest. Dermatol., vol. 129, 2009, pp. 891-898.
Kim, S.D., et al., "The agonists of formyl peptide receptors prevent development of severe sepsis after microbial infection", J. Immunol., vol. 185, 2010, pp. 4302-4310.
Hillenbrand, A, et al., "Sepsis induced changes of adipokines and cytokines—septic patients compared to morbidly obese patients", BMC Surgery, vol. 10, No. 26, 2010, 9 pages.
Hamishehkar, H., et al., "Identification of enhanced cytokine generation following sepsis. Dream of magic bullet for mortality prediction and therapeutic evaluation", DARU, Vo. 18, No. 3, 2010, pp. 155-162.
Delavallèe, L, et al., "Anti-cytokine vaccination in autoimmune diseases", Swiss Med Wkly., vol. 140:w13108; 2010, 6 pgs.
Finkelman, F.D., et al., "Importance of cytokines in murine allergic airway disease and human asthma", J Immunol., vol. 184, 2010, pp. 1663-1674.
Corren, J., "Cytokine inhibition in severe asthma: current knowledge and future directions", Current Opinion in Pulmonary Medicine, vol. 17, 2011, pp. 29-33.
De Paz, B, et al., "Cytokines and regulatory T cells in rheumatoid arthritis and their relationship with response to corticosteroids". The Journal of Rheumatology, vol. 37, No. 12, 2010, pp. 2502-2510.
Agarwal, V. and Malaviya, A.N., "Cytokine network and its manipulation in rheumatoid arthritis", J. Indian Rheumatol. Assoc., vol. 13, 2005, pp. 86-91.
Broos, S. et al., "Immunomodulatory nanoparticles as adjuvants and allergen-delivery system to human dendritic cells: Implications for specific immunotherapy", Vaccine, vol. 28, 2010, pp. 5075-5085.
Morimoto, Y., et al., "Expression of inflammation-related cytokines following ii illatracheal instillation of nickel oxide nanoparticles", Nanotoxicology, vol. 4, No. 2, Jun. 2010, pp. 161-176.
Summer, B., et al., "Nickel (Ni) allergic patients with complications to Ni containing joint replacement show preferential IL-17 type reactivity to Ni", Contact Dermatitis, vol. 63, 2010, pp. 15-22.
Schutte, R.J., et al., "In vivo cytokine-associated responses to biomaterials", Biomaterials, vol. 30, 2009, pp. 160-168.
Rodriguez, A., et al., "Quantitative in vivo cytokine analysis at synthetic biomaterial implant sites", Journal of Biomedical Materials Research Part A, vol. 89, No. 1, Apr. 2008, pp. 152-159.
Roberts-Thomson, I.C., et al., "Cells, cytokines and inflammatory bowel disease: a clinical perspective", Expert Review of Gaslioenterology and Hepatology, vol. 5, No. 6, Dec. 2011, pp. 703-716.
Rogler, G. and Andus, T., "Cytokines in inflammatory bowel disease", World Journal of Surgery, vol. 22, 1998, pp. 382-389.
Chanput, W., et al., "Transcriptional pioliles of LPS-stimulated THP-1 monocytes and macrophages: a tool to study inflammation modulating effects of food-derived compounds", Food & Function, vol. 1, 2010, pp. 254-261.

* cited by examiner

USE OF IMMUNE SUPPRESSIVE DOMAINS AS MEDICAMENTS

The present invention relates to uses of immune suppressive domains. In particular, the present invention concerns a use of an immune suppressive domain (ISD) for immune suppression and for reduction of inflammation. Further, the invention concerns a class of multifunctional drugs for treatment of inflammatory diseases or as coatings for biomaterial or nanoparticles. Additionally, the invention relates to compositions comprising immunosuppressive polypeptides that are derived from enveloped RNA viruses. The present invention also relates to methods for producing said compositions, as well as the usage of said compositions for treatment of inflammatory disorders or protection of nanoparticles, biomaterials and/or medical devices such as cathedra, implants, plaster, etc to prevent or subdue undesired immunological adverse effects from the host.

TECHNICAL BACKGROUND

Retroviral infections cause a significant immunosuppression. A small part of the viral glycoprotein induces a significant immunosuppressive effect. This part has been termed the immunosuppressive domain (ISD) and comprise only 17 amino acids. ISD when produced as an isolated 17 amino acid peptide has several effects on the immune response, which among others are: In vitro inhibition of Natural Killer cells, cytotoxic T lymphocytes (CTLs) and inhibition of IL-2 dependent proliferation of T lymphocytes [Cianciolo 1985, Denner 1994, Harrell 1986, Kleinerman 1987]. Furthermore, human endogenous retroviruses can antagonize the immune-dependent elimination of tumor cells injected into immunocompetent mice after transduction of these tumor cells by an envelope-expression vector [Mangeney 1998]. ISD activates intracellular signaling molecules causing inhibition of Th1 cytokines (IL-1α, IL-2, IL-6 IL-12, INF-α/γ, TNF-α) [Haraguchi 1995, Haraguchi 1995a, Haraguchi 2008, coelcialli 2012]). Finally, a human gene syncytin-2 contains a homologous domain with immunosuppressive activity. This gene is expressed during placental morphogenesis and is believed to be involved in paterno-fetal immune tolerance [Mangeney 2007].

For sepsis many papers has described the desired effect upon the cytokine profile following treatment. Below are reference for three such papers:

In one investigation plasma levels of critically ill patients of resistin, active PAI-1, MCP-1, IL-1 alpha, IL-6, IL-8, IL-10, and TNF-alpha were significantly elevated compared to 60 healthy blood donors. Making these cytokines targets for downregulation by immunosuppressive peptides (BMC Surg. 2010 Sep. 9; 10:26.Sepsis induced changes of adipokines and cytokines—septic patients compared to morbidly obese patients. Hillenbrand A, Knippschild U, Weiss M, Schrezenmeier H, Henne-Bruns D, Huber-Lang M, Wolf A M. Department of General-, Visceral-, and Transplantation Surgery, University Hospital of Ulm, Steinhoevelstr, Ulm, Germany. Andreas.Hillenbrand@uniklinik-ulm.)

In a second paper A prospective observational study was used to determine the predictive role of Tumor Necrosis Factor alpha (TNF-α), Interleukin (IL)-1β and IL-6 as three main pro-inflammatory cytokines and Acute Physiology and Chronic Health Evaluation (APACHE II) and Sequential Organ Failure Assessment (SOFA) as two scoring systems in mortality of critically ill patients with severe sepsis. Fifty and five patients with criteria of severe sepsis were included in this study. An exclusion criterion was post Cardiopulmonary Resuscitation (CPR) status. Cytokines (TNF-α, IL-1β and IL-6) were assayed in the first, third and seventh days in blood of patients. RESULTS AND MAJOR CONCLUSION: Among three measured cytokines, sequential levels of TNF-α and IL-6 showed significant differences between survivors and nonsurvivors. IL-6 had a good correlation with outcome and scoring systems during the period of this study. The areas under the receiver operating characteristic (AUROC) curve indicated that APACHE II (0.858, 0.848, 0.861) and IL-6 (0.797, 0.799, 0.899) had discriminative power in prediction of mortality during sequental measured days. Multiple logestic regression analysis identified that evaluation of APACHE II and TNF-α in the first day and APACHE II and IL-6 in the third and seventh days of severe septic patients are independent outcome predictors. Results of this study suggest that IL-6 and APACHE II are useful cytokine and scoring systems respectively in prediction of mortality and clinical evaluation of severe septic patients. (Daru. 2010; 18(3):155-62. Identification of enhanced cytokine generation following sepsis. Dream of magic bullet for mortality prediction and therapeutic evaluation. Hamishehkar H, Beigmohammadi M T, Abdollahi M, Ahmadi A, Mahmoodpour A, Mirjalili M R, Abrishami R, Khoshayand M R, Eslami K, Kanani M, Baeeri M, Mojtahedzadeh M. Department of Clinical Pharmacy, acuity of Pharmacy and Pharmaceutical Sciences Research Center, Tehran University of Medical Sciences, Tehran).

Paper 3: J Immunol. 2010 Oct. 1; 185(7):4302-10. Epub 2010 Sep. 3. The agonists of formyl peptide receptors prevent development of severe sepsis after microbial infection. Kim S D, Kim Y K, Lee H Y, Kim Y S, Jeon S G, Baek S H, Song D K, Ryu S H, Bae Y S. Department of Biological Sciences, Sungkyunkwan University, Suwon, South Korea.

Autoimmune Diseases

Autoimmune diseases arise from an inappropriate immune response of the body against substances and tissues normally present in the body. In other words, the immune system mistakes some part of the body as a pathogen and attacks its own cells. This may be restricted to certain organs (e.g. in autoimmune thyroiditis) or involve a particular tissue in different places (e.g. Goodpasture's disease which may affect the basement membrane in both the lung and the kidney). The treatment of autoimmune diseases is typically with immunosuppression—medication which decreases the immune response For autoimmune diseases several papers has described the desired effect upon the cytokine profile following treatment. Below is the abstract and reference for one such As described in one paper: The concept of therapeutic vaccination represents a novel strategy of active immunotherapy that can be applied to autoimmune disease. The principle is to design molecules which can trigger an immune response, targeting a cytokine that is pathogenic and over-expressed in a given disease. The mostly available vaccines are an application of vaccination using either the self-protein coupled to a carrier (type I A), or a modified form of the protein engineered to include neo-epitopes (type I B). These approaches have been developed in models of several autoimmune diseases, mainly in TNFα-dependent diseases such as rheumatoid arthritis and Crohn's disease, but also in systemic lupus erythematosus, multiple sclerosis and myasthenia gravis. Clinical trials are in progress in rheumatoid arthritis, Crohn's disease and diabetes. The benefit/risk ratio of anti-cytokine vaccination is currently under study to further develop the vaccination strategies. (Swiss Med Wkly. 2010 Nov. 1; 140:w13108. doi: 10.4414/smw.2010.13108. Anti-cytokine vaccination in autoimmune diseases. Delavallée L, Duvallet E, Semerano L, Assier E, Boissier M C. University Paris 13, PRES Paris Cité Sorbonne, Bobigny, France. laure.delavallee@upmc.fr).

Asthma

Asthma is the common chronic inflammatory disease of the airways characterized by variable and recurring symptoms, reversible airflow obstruction, and bronchospasm. Symptoms include wheezing, coughing, chest tightness, and shortness of breath. Asthma is clinically classified according to the frequency of symptoms, forced expiratory volume in 1 second (FEV1), and peak expiratory flow rate. Asthma may also be classified as atopic (extrinsic) or non-atopic (intrinsic).

It is thought to be caused by a combination of genetic and environmental factors. Treatment of acute symptoms is usually with an inhaled short-acting beta-2 agonist (such as salbutamol). Symptoms can be prevented by avoiding triggers, such as allergens and irritants, and by inhaling corticosteroids. Leukotriene antagonists are less effective than corticosteroids and thus less preferred. Its diagnosis is usually made based on the pattern of symptoms and/or response to therapy over time. The prevalence of asthma has increased significantly since the 1970s. As of 2010, 300 million people were affected worldwide. In 2009 asthma caused 250,000 deaths globally.

For Asthma several papers has described the desired effect upon the cytokine profile following treatment. Below is the abstract and reference for two such papers:

The first paper notes that Asthma is a common, disabling inflammatory respiratory disease that has increased in frequency and severity in developed nations. We review studies of murine allergic airway disease (MAAD) and human asthma that evaluate the importance of Th2 cytokines, Th2 response-promoting cytokines, IL-17, and proinflammatory and anti-inflammatory cytokines in MAAD and human asthma. We discuss murine studies that directly stimulate airways with specific cytokines or delete, inactivate, neutralize, or block specific cytokines or their receptors, as well as controversial issues including the roles of IL-5, IL-17, and IL-13Ralpha2 in MAAD and IL-4Ralpha expression by specific cell types. Studies of human asthmatic cytokine gene and protein expression, linkage of cytokine polymorphisms to asthma, cytokine responses to allergen stimulation, and clinical responses to cytokine antagonists are discussed as well. Results of these analyses establish the importance of specific cytokines in MAAD and human asthma and have therapeutic implications. (J Immunol. 2010 Feb. 15; 184(4):1663-74. Importance of cytokines in murine allergic airway disease and human asthma. Finkelman F D, Hogan S P, Hershey G K, Rothenberg M E, Wills-Karp M. Department of Medicine, Cincinnati Veterans Affairs Medical Center, Cincinnati, Ohio 45220, USA. finkelman@pol.net).

The second paper notes that a growing list of cytokines that contribute to the pathogenesis of asthma has been identified. The purpose of this review is to explore the specific cytokines involved in asthma, including their functions, cell sources, and clinical evidence that they participate in asthma. Existing data from clinical trials of cytokine antagonists in asthmatic patients are then reviewed to determine the efficacy and safety of these compounds. RECENT FINDINGS: Cytokine antagonists that have been investigated recently in asthma include monoclonal antibodies directed against interleukin (IL)-5, tumor necrosis factor-alpha (TNF-α), and IL-4/IL-13. Ongoing and future clinical investigations of inhibitors directed at IL-9, IL-13, IL-17, and thymic stromal lymphopoietin may offer potential new agents that will play roles in the treatment of severe asthma. (Curr Opin Pulm Med. 2011 January; 17(1):29-33. Cytokine inhibition in severe asthma: current knowledge and future directions. Corren J. Research Division, Allergy Medical Clinic, Los Angeles, Calif. 90025, USA. jcorren@ucla.edu).

Arthritis

Arthritis (from Greek arthro-, joint+-itis, inflammation; plural: arthritides) is a form of joint disorder that involves inflammation of one or more joints.

There are over 100 different forms of arthritis. The most common form, osteoarthritis (degenerative joint disease), is a result of trauma to the joint, infection of the joint, or age. Other arthritis forms are rheumatoid arthritis, psoriatic arthritis, and related autoimmune diseases. Septic arthritis is caused by joint infection.

The major complaint by individuals who have arthritis is joint pain. Pain is often a constant and may be localized to the joint affected. The pain from arthritis is due to inflammation that occurs around the joint, damage to the joint from disease, daily wear and tear of joint, muscle strains caused by forceful movements against stiff, painful joints and fatigue.

For Arthritis several papers has described the desired effect upon the cytokine profile following treatment. Below is the abstract and reference for two such papers:

The first paper sets out to analyze circulating cytokines and regulatory T cells (Treg) in patients with rheumatoid arthritis (RA) of different durations, and their association with functional interleukin 10 (IL-10) and tumor necrosis factor-α (TNF-α) genotypes in patients treated with corticosteroids. METHODS: Serum levels of IL-6, IL-10, IL-17, IL-18, TNF-α, and transforming growth factor-ß (TGF-ß) were quantified in 196 patients and 61 healthy controls. Percentage of CD4+CD25high cells was determined by flow cytometry and Foxp3 expression by real-time reverse-transcription polymerase chain reaction. Data were related to clinical measurements and presence of the genotype-1082GG IL-10/-308GG TNF-α, previously associated with good response to corticosteroids. RESULTS: Levels of TNF-α, IL-6, and IL-18 were significantly higher in patients compared to controls, while TGF-ß and IL-10 were lower. Serum samples of patients at disease onset (n=32) had increased IL-6 and decreased TGF-ß, but there were no differences in other cytokines. These patients also presented a higher percentage of CD4+CD25high cells than those with established disease, although no significant differences were detected in Foxp3. Patients under corticosteroid treatment who were carriers of the good responder genotype had higher levels of TGF-ß, Foxp3, and Treg compared to patients with other genotypes, while relatively lower levels of TNF-α and IL-17 were observed. CONCLUSION: Patients at onset of RA present fewer alterations in cytokine levels and Treg than those with longer disease duration, supporting the role of disease progression in subsequent changes. The antiinflammatory balance observed in high IL-10/low TNF-α patients treated with prednisone supports the use of these genetic polymorphisms as predictors of response to corticosteroid therapy. (J Rheumatol. 2010 December; 37(12):2502-10. Epub 2010 Oct. 15. Cytokines and regulatory T cells in rheumatoid arthritis and their relationship with response to corticosteroids. de Paz B, Alperi-López M, Ballina-García F J, Prado C, Gutiérrez C, Suárez A. Department of Functional Biology, Immunology Area, University of Oviedo, Oviedo, Spain.)

The second paper provides studies of the inflammatory process in the inflamed synovium from rheumatoid arthritis patients have shown an intricate network of molecules involved in its initiation, perpetuation and regulation trial balances the pro- and anti-inflammatory process. This system is self-regulating though the action of anti-inflammatory and pro-inflammatory cytokines cytokine receptor antagonists and naturally occurring antibodies cytokines. Inflammatory synovitis in rheumatoid arthritis (and possibly in other inflammatory arthritidies) appears to be the result of an imbalance in the cytokine network with either an excess production of pro-inflammatory cytokines or from inadequacy of the natural anti-inflammatory mechanisms. Using this knowledge the newer therapeutic approaches to RA and other inflammatory arthritides are being aimed at correcting this imbalance. Monoclonal antibodies to INF-alpha (humanised form of this is called infliximab), soluble TNF-alpha receptors (etanercept) are already in clinical use and adalimumab (humanised TNF-alpha antibody). IL-1Ra is undergoing clinical trials. Other promising therapeutic agents that could regulate the cytokine network are in various stages of laboratory and clinical evaluation. These studies promise to yield therapeutic targets that could dramatically change the way inflammatory diseases would be treated in the future. The now established efficacy of infliximab and etanercept in inflammatory arthritides could be considered just a glimpse of the exciting scenario of the future. (J Assoc Physicians India. 2006 June; 54 Suppl:15-8. Cytokine network and its manipulation in rheumatoid arthritis. Malaviya A M. A7R Clinic for Arthritis and Rheumatism, Consultant Rheumatologist Indian Spinal Centre, New Delhi—110 07.)

Inflammatory Bowel Disease

In medicine, inflammatory bowel disease (IBD) is a group of inflammatory conditions of the colon and small intestine. The major types of IBD are Crohn's disease and ulcerative colitis.

For Inflammatory bowel disease several papers has described the desired effect upon the cytokine profile following treatment. Below is the abstract and reference for two such papers:

The first paper discloses that Cytokines play a central role in the modulation of the intestinal immune system. They are produced by lymphocytes (especially T cells of the Th1 and Th2 phenotypes), monocytes, intestinal macrophages, granulocytes, epithelial cells, endothelial cells, and fibroblasts. They have proinflammatory functions [interleukin-1 (IL-1), tumor necrosis factor (TNF), IL-6, IL-8, IL-12] or antiinflammatory functions [interleukin-1 receptor antagonist (IL-1ra), IL-4, IL-10, IL-11, transforming growth factor beta (TGF beta)]. Mucosal and systemic concentrations of many pro- and antiinflammatory cytokines are elevated in inflammatory bowel disease (IBD). An imbalance between proinflammatory and antiinflammatory cytokines was found for the IL-1/IL-1ra ratio in the inflamed mucosa of patients with Crohn's disease, ulcerative colitis, diverticulitis, and infectious colitis. Furthermore, the inhibition of proinflammatory cytokines and the upplementations with antiinflammatory cytokines reduced inflammation in animal models, such as the dextran sulfate colitis (DSS) model, the trinitrobenzene sulfonic acid (TNBS) model, or the genetically engineered model of IL-10 knockout mice. Based on these findings a rationale for cytokine treatment was defined. The first clinical trials using neutralizing monoclonal antibodies against TNF alpha (cA2) or the antiinflammatory cytokine IL-10 have shown promising results. However, many questions must be answered before cytokines can be considered standard therapy for IBD. (World J Surg. 1998 April; 22(4): 382-9. Cytokines in inflammatory bowel disease. Rogler G, Andus T. Department of Internal Medicine I, University of Regensburg, Germany.)

The second paper discloses that Ulcerative colitis and Crohn's disease are chronic inflammatory disorders of the GI tract. Although the disorders can usually be distinguished on clinical and pathological criteria, there are similarities in natural history and response to therapy. The purpose of this article is to examine the inflammatory infiltrate in both disorders and the cytokine profiles in intestinal mucosa and peripheral blood. For both disorders, the predominant cells in inflamed mucosa are neutrophils and lymphocytes positive for CD4. There are also increases in the number of B cells, macrophages, dendritic cells, plasma cells, eosinophils and perhaps mast cells. Cytokine levels and cytokine expression are also similar for both disorders, with increases in TNF-α and IFN-γ consistent with a Th1 response. As inflammation occurs in a microbial environment, one possibility is that the nature of the inflammatory response is largely independent of initiating factors. One concept that might be useful is that of initiating cells and cytokines and effector cells and cytokines. Persuasive evidence exists for a defect in phagocytic cells in Crohn's disease, perhaps with the expansion of a subset of activated macrophages. There are also possible links to natural killer cells and changes in the regulation of IL-8 and perhaps IL-22. For ulcerative colitis, the cellular events are less clear, but natural killer T cells may be important as initiating cells, and there is some evidence for upregulation of cytokines involved in Th2 responses, including IL-4 and IL-13. For both disorders, proinflammatory cytokines include TNF-α, IL-12, IL-23, and perhaps IL-17 and IFN-γ. Research challenges include the identification, activation and function of subsets of inflammatory cells, as well as new ways to terminate the inflammatory response. (Expert Rev Gastroenterol Hepatol. 2011 December; 5(6):703-16. Cells, cytokines and inflammatory bowel disease: a clinical perspective. Roberts-Thomson I C, Fon J, Uylaki W, Cummins A G, Barry S. Department of Gastroenterology and Hepatology, The Queen Elizabeth Hospital, Adelaide, South Australia, Australia. ian.roberts-thomson@health.sa.gov.au).

Food Allergy

A food allergy is an adverse immune response to a food protein. They are distinct from other adverse responses to food, such as food intolerance, pharmacological reactions, and toxin-mediated reactions.

The protein in the food is the most common allergic component. These kinds of allergies occur when the body's immune system mistakenly identifies a protein as harmful. Some proteins or fragments of proteins are resistant to digestion and those that are not broken down in the digestive process are tagged by the Immunoglobulin E (IgE). These tags fool the immune system into thinking that the protein is harmful. The immune system, thinking the organism (the individual) is under attack, triggers an allergic reaction. These reactions can range from mild to severe. Allergic responses include dermatitis, gastrointestinal and respiratory distress, including such life-threatening anaphylactic responses as biphasic anaphylaxis and vasodilation; these require immediate emergency intervention. Individuals with protein allergies commonly avoid contact with the problematic protein. Some medications may prevent, minimize or treat protein allergy reactions.

Treatment consists of either immunotherapy (desensitisation) or avoidance, in which the allergic person avoids all forms of contact with the food to which they are allergic. Areas of research include anti-IgE antibody (omalizumab, or Xolair) and specific oral tolerance induction (SOTI), which have shown some promise for treatment of certain food allergies. People diagnosed with a food allergy may carry an injectable form of epinephrine such as an EpiPen, or wear some form of medical alert jewelry, or develop an emergency action plan, in accordance with their doctor.

The scope of the problem, particularly for young people, is a significant public health issue.

Food allergy is thought to develop more easily in patients with the atopic syndrome, a very common combination of diseases: allergic rhinitis and conjunctivitis, eczema and asthma. The syndrome has a strong inherited component; a family history of allergic diseases can be indicative of the atopic syndrome.

Food Intolerance

Food intolerance or non-allergic food hypersensitivity is a term used widely for varied physiological responses associated with a particular food, or compound found in a range of foods.

Food intolerance is negative reaction, often delayed, to a food, beverage, food additive, or compound found in foods that produces symptoms in one or more body organs and systems, but it is not a true food allergy. A true food allergy requires the presence of Immunoglobin E (IgE) antibodies against the food, and a food intolerance does not.

Food intolerances can be classified according to their mechanism. Intolerance can result from the absence of specific chemicals or enzymes needed to digest a food substance, as in hereditary fructose intolerance. It may be a result of an abnormality in the body's ability to absorb nutrients, as occurs in fructose malabsorption. Food intolerance reactions can occur to naturally occurring chemicals in foods, as in salicylate sensitivity. Drugs sourced from plants, such as aspirin, can also cause these kinds of reactions. Finally, it may be the result of non-IgE-mediated immune responses.

Non-allergic food hypersensitivity is the medical name for food intolerance, loosely referred to as food hypersensitivity, or previously as pseudo-allergic reactions. Non-allergic food hypersensitivity should not be confused with true food allergies Food intolerance reactions can include pharmacologic, metabolic, and gastro-intestinal responses to foods or food compounds. Food intolerance does not include either psychological responses or foodborne illness.

Nanoparticle

In nanotechnology, a particle is defined as a small object that behaves as a whole unit in terms of its transport and properties. Particles are further classified according to size: in terms of diameter, coarse particles cover a range between 10,000 and 2,500 nanometers. Fine particles are sized between 2,500 and 100 nanometers. Ultrafine particles, or nanoparticles are sized between 100 and 1 nanometers. The reason for this double name of the same object is that, during the 1970-80's, when the first thorough fundamental studies were running with "nanoparticles" in the USA (by Granqvist and Buhrman) and Japan, (within an ERATO Project) they were called "ultrafine particles" (UFP). However, during the 1990s before the National Nanotechnology Initiative was launched in the USA, the new name, "nanoparticle" had become fashionable (see, for example the same senior author's paper 20 years later addressing the same issue, lognormal distribution of sizes). Nanoparticles may or may not exhibit size-related properties that differ significantly from those observed in fine particles or bulk materials. Although the size of most molecules would fit into the above outline, individual molecules are usually not referred to as nanoparticles.

Nanoparticle research is currently an area of intense scientific interest due to a wide variety of potential applications in biomedical, optical and electronic fields.

For coating and production of nanoparticles several papers has described the desired effect upon the cytokine profile following injection into the patient. Below is the abstract and reference two such papers:

The first paper discloses novel adjuvants and antigen-delivery systems with immunomodulatory properties that shift the allergenic Th2 response towards a Th1 or regulatory T cell response are desired for allergen-specific immunotherapy. This study demonstrates that 200-nm sized biodegradable poly(gamma-glutamic acid) (gamma-PGA) nanoparticles (NPs) are activators of human monocyte-derived dendritic cells (MoDCs). Gamma-PGA NPs are efficiently internalized by immature MoDCs and strongly stimulate production of chemokines and inflammatory cytokines as well as up-regulation of co-stimulatory molecules and immunomodulatory mediators involved in efficient T cell priming. Furthermore, MoDCs from allergic subjects stimulated in vitro with a mixture of gamma-PGA NPs and extract of grass pollen allergen Phleum pratense (Phl p) augment allergen-specific IL-10 production and proliferation of autologous CD4(+) memory T cells. Thus, gamma-PGA NPs are promising as sophisticated adjuvants and allergen-delivery systems in allergen-specific immunotherapy. (Vaccine. 2010 Jul. 12; 28(31):5075-85. Epub 2010 May 15. Immunomodulatory nanoparticles as adjuvants and allergen-delivery system to human dendritic cells: Implications for specific immunotherapy. Broos S, Lundberg K, Akagi T, Kadowaki K, Akashi M, Greiff L, Borrebaeck C A, Lindstedt M. Department of Immunotechnology, Lund University, Lund, Sweden.)

The second paper has the objective to examine what kinds of cytokines are related to lung disorder by well-dispersed nanoparticles. The mass median diameter of nickel oxide in distilled water was 26 nm. Rats intratracheally received 0.2 mg of nickel oxide suspended in distilled water, and were sacrificed from three days to six months. The concentrations of 21 cytokines including inflammation, fibrosis and allergy-related ones were measured in the lung. Infiltration of alveolar macrophages was observed persistently in the nickel oxide-exposed group. Expression of macrophage inflammatory protein-1alpha showed a continued increase in lung tissue and broncho-alveolar lavage fluid (BALF) while interleukin-1alpha (IL-1alpha), IL-1beta in lung tissue and monocyte chemotactic protein-1 in BALF showed transient increases. Taken together, it was suggested that nano-agglomerates of nickel oxide nanoparticles have a persistent inflammatory effect, and the transient increase in cytokine expression and persistent increases in CC chemokine were involved in the persistent pulmonary inflammation. (Nanotoxicology. 2010 June; 4(2):161-76. Expression of inflammation-related cytokines following intratracheal instillation of nickel oxide nanoparticles. Morimoto Y, Ogami A, Todoroki M, Yamamoto M, Murakami M, Hirohashi M, Oyabu T, Myojo T, Nishi K, Kadoya C, Yamasaki S, Nagatomo H, Fujita K, Endoh S, Uchida K, Yamamoto K, Kobayashi N, Nakanishi J, Tanaka I. Institute of Industrial Ecological Sciences, University of Occupational and Environmental Health, Kitakyushu, Fukuoka, Japan. yasuom@med.uoeh-u.ac.jp).

Biomaterials

A biomaterial is any matter, surface, or construct that interacts with biological systems. The development of biomaterials, as a science, is about fifty years old. The study of biomaterials is called biomaterials science. It has experienced steady and strong growth over its history, with many companies investing large amounts of money into the development of new products. Biomaterials science encompasses elements of medicine, biology, chemistry, tissue engineering and materials science.

Biomaterials can be derived either from nature or synthesized in the laboratory using a variety of chemical approaches utilizing metallic components or ceramics. They are often used and/or adapted for a medical application, and thus comprises whole or part of a living structure or biomedical device which performs, augments, or replaces a natural function. Such functions may be benign, like being used for a heart valve, or may be bioactive with a more interactive functionality such as hydroxy-apatite coated hip implants. Biomaterials are also used every day in dental applications, surgery, and drug delivery. E.G. A construct with impregnated pharmaceutical products can be placed into the body, which permits the prolonged release of a drug over an extended period of time. A biomaterial may also be an autograft, allograft or xenograft used as a transplant material.

Materials scientists are currently paying more and more attention to the process inorganic crystallization within a largely organic matrix of naturally occurring compounds. This process typically generally occurs at ambient temperature and pressure. Interestingly, the vital organisms through which these crystalline minerals form are capable of consistently producing intricately complex structures. Understanding the processes in which living organisms are capable of regulating the growth of crystalline minerals such as silica could lead to significant scientific advances and novel synthesis techniques for nanoscale composite materials—or nanocomposites.

Biomaterials are used in: Joint replacements, Bone plates, Bone cement, Artificial ligaments and tendons, Dental implants for tooth fixation, Blood vessel prostheses, Heart valves, Skin repair devices (artificial tissue), Cochlear replacements, Contact lenses, Breast implants Biomaterials must be compatible with the body, and there are often issues of biocompatibility which must be resolved before a product can be placed on the market and used in a clinical setting. Because of this, biomaterials are usually subjected to the same requirements as those undergone by new drug therapies.

For coating and production of biomaterials several papers has described the desired effect upon the cytokine profile following injection into the patient. Below is the abstract and reference three such papers:

The first paper discloses that some nickel (Ni) allergic patients develop complications following Ni-containing arthroplasty. In the peri-implant tissue of such patients, we had observed lymphocyte dominated inflammation together with IFN-gamma and IL-17 expression. OBJECTIVES: To determine whether Ni stimulation of peripheral blood mononuclear cells (PBMCs) of such patients would lead to a different cytokine pattern as compared to Ni-allergic patients with symptom-free arthroplasty. PATIENTS AND METHODS: Based on history and patch testing in 15 Ni-allergic patients (five without implant, five with symptom-free arthroplasty, five with complicated arthroplasty) and five non-allergic individuals, lymphocyte transformation test (LTT) was performed using PBMC. In parallel in vitro cytokine response to Ni was assessed by real-time reverse anscriptase-polymerase chain reaction (RT-PCR).

RESULTS: All 15 Ni-allergic individuals showed enhanced LTT reactivity to Ni (mean SI=8.42+/−1.8) compared to the non-allergic control group. Predominant IFN-gamma expression to Ni was found both in the five allergic patients without arthroplasty and also in the five allergic, symptom-free arthroplasty patients. In contrast, in the five Ni-allergic patients with arthroplasty-linked complications a predominant, significant IL-17 expression to Ni was seen but not in patients with symptom-free arthroplasty. CONCLUSIONS: The predominant IL-17 type response to Ni may characterize a subgroup of Ni-allergic patients prone to develop lymphocytic peri-implant hyper-reactivity. (Contact Dermatitis. 2010 July; 63(1):15-22. Nickel (Ni) allergic patients with complications to Ni containing joint replacement show preferential IL-17 type reactivity to Ni. Summer B, Paul C, Mazoochian F, Rau C, Thomsen M, Banke I, Gollwitzer H, Dietrich K A, Mayer-Wagner S, Ruzicka T, Thomas P. Klinik und Poliklinik für Dermatologie und Allergologie, Ludwig-Maximilians-Universitat, Munchen, Germany. Burkhard.Summer@med.uni-muenchen.de).

The second paper says that cytokines, chemokines, and growth factors were analyzed periodically over eight weeks from the wound exudate fluid surrounding biomaterials implanted subcutaneously within stainless steel mesh cages. TNF-alpha, MCP-1, MIP-1alpha, IL-2, IL-6, IL-1beta, VEGF, IL-4, and IL-10 were measured from exudate samples collected from cages containing specimens of polyethylene (PE), polyurethane (PU), or organotin polyvinyl chloride (ot-PVC). Empty cages served as negative controls, and lipopolysaccharide (LPS) served as a positive control. Cytokine, chemokine, and growth factor concentrations decreased from the time of implantation to eight weeks post-implantation, and there was an overall increase in cytokine, chemokine, and growth factor production for material-containing cages compared to empty cages. However, cytokine production was only modestly affected by the different surface chemistries of the three implanted polymeric materials. (Biomaterials. 2009 January; 30(2):160-8. Epub 2008 Oct. 11. In vivo cytokine-associated responses to biomaterials. Schutte R J, Xie L, Klitzman B, Reichert W M. Department of Biomedical Engineering, Duke University, Durham, N.C. 27708, USA.)

The third paper sets out to further elucidate the foreign body reaction, investigation of cytokines at biomaterial implant sites was carried out using a multiplex immunoassay and ELISA. Macrophage activation cytokines (IL-1beta, IL-6, and TNFalpha), cytokines important for macrophage fusion (IL-4 and IL-13), antiinflammatory cytokines (IL-10 and TGFbeta), chemokines (GRO/KC, MCP-1), and the T-cell activation cytokine IL-2 were quantified at biomaterial implant sites. Empty cages (controls) or cages containing synthetic biomedical polymer (Elasthane 80A (PEU), silicone rubber (SR), or polyethylene terephthalate (PET)) were implanted subcutaneously in Sprague-Dawley rats for 4, 7, or 14 days, and cytokines in exudate supernatants and macrophage surface adhesion and fusion were quantified. The presence of a polymer implant did not affect the levels of IL-1beta, TGFbeta, and MCP-1 in comparison to the control group. IL-2 was not virtually detected in any of the samples. Although the levels of IL-4, IL-13, IL-10, and GRO/KC were affected by polymer implantation, but not dependent on a specific polymer, IL-6 and TNFalpha were significantly greater in those animals implanted with PEU and SR, materials that do not promote fusion. The results indicate that differential material-dependent cytokine profiles are produced by surface adherent macrophagesand foreign body giant cells in vivo. (J Biomed Mater Res A. 2009 April; 89(1):152-9. Quantitative in vivo cytokine analysis at synthetic biomaterial implant sites. Rodriguez A, Meyerson H, Anderson J M. Department of Pathology, Case Western Reserve University, Cleveland, Ohio 44106, USA.)

SUMMARY OF THE INVENTION

According to an aspect, the present invention relates to compositions of immunosuppressive peptides derived from enveloped RNA viruses.

In another aspect the present invention relates to compositions of immunosuppressive peptides derived from the fusion peptide of enveloped RNA viruses.

In third aspect the present invention relates to compositions of immunosuppressive peptides derived from the fusion peptide of influenza virus.

In fourth aspect the present invention relates to a composition comprising one or more of said immunosuppressive peptides, or part thereof.

In a fifth aspect the present invention relates to a pharmaceutical composition comprising one or more immunosuppressive peptides and further comprising a pharmaceutical acceptable carrier or salt.

In a sixth aspect the present invention relates to usage of compositions of said immunosuppressive peptides for treatment of inflammatory disorders.

In a seventh aspect the present invention relates to usage of compositions of said immunosuppressive peptides for usage for protection of nanoparticles or biomaterials from undesirable immunological adverse reactions.

In a further aspect the present invention relates to a method of producing a composition comprising immunosuppressive peptides, said method comprising the steps of:

a) providing one or more immunosuppressive peptides
b) optionally cross-linking the immunosuppressive peptides provided in step a),
c) optionally providing a carrier
d) providing a substance
e) mixing the peptides of step a) or optionally step b) or step c) with the substance of step d.
f) obtaining the composition of the present invention.

According to an additional aspect, the invention concerns an immune suppressive domain for use as a medicament.

According to another aspect, the invention concerns a use of an immune suppressive domain for the manufacture of a medicament for immune suppression.

According to an additional aspect, the invention concerns a method for the preparation of a pharmaceutical composition comprising the steps of:

a. Providing one or more immunosuppressive peptides selected from Seqid 1 to Seqid 287, and optionally cross-linking said one or more immunosuppressive peptides;
b. Optionally providing a carrier;
c. Providing a substance;
d. Mixing the provided one or more peptides with any carrier of optional step b. and the substance of step d. to obtain the pharmaceutical composition.

According to an additional aspect, the invention concerns a pharmaceutical composition obtainable according to the invention.

According to another aspect, the invention concerns a pharmaceutical composition comprising an immune suppressive domain as an active substance.

According to an additional aspect, the invention concerns a use of the composition according to the invention, for treatment of a disease by IV injection.

According to an additional aspect, the invention concerns the use of the composition according to the invention, to increase the half-life of nanoparticles or biomaterials in vivo in a patient.

According to an additional aspect, the invention concerns a vaccine comprising an immune suppressive domain selected among Seqid 275 to 287 against PRRS.

According to another aspect, the invention concerns a vaccine against PRRS comprising a mutated immunosuppressive domain selected among Seqid 275 to Seqid 287, subject to the proviso that the immunosuppressive properties of said domain have been abrogated.

According to another aspect, the invention concerns a peptide having the sequence of an Immune Suppressive Domain according to the invention.

According to an aspect, the invention concerns the use of a peptide according to the invention, said use being selected among any of the uses of Immune Suppressive Domains of the invention.

According to an aspect, the invention concerns a method of treatment of an indication selected among the indications of the present application and the viral infections of Table 1 comprising administration of an effective amount of an entity selected among the Immune Suppressive Domains of the invention, the compositions of the invention, and the peptides of the invention.

DETAILED DISCLOSURE

According to an embodiment, the present invention concerns compositions of one or more immunosuppressive peptides. Immunosuppressive polypeptides are polypeptides that are capable of suppressing an immune response in animals, including human beings and other animal such as domestic or agricultural (cats, dogs, cows, sheep, horses, pigs, etc.) or test species such as mouse, rats, rabbits and the like.

In one embodiment of the present invention the immunosuppressive polypeptides are capable of at least 5% inhibition of T-lymphocyte proliferation, at least 10%, at least 20%, such as at least 30%, at least 40%, at least 50%, such as at least 60%, such as at least 70% inhibition of T-lymphocyte proliferation. In particular embodiments the immunosuppressive peptides of the present invention are capable of at least 75% inhibition of T-lymphocyte proliferation, at least 80%, such as at least 85%, at least 90%, such as at least 95%, at least 97%, such as at least 99%, at least 100% inhibition of T-lymphocyte proliferation.

According to another embodiment of the present invention the immunosuppressive polypeptides are capable of suppressing the immune response in an animal suffering from a general skin inflammation according to the TPA model, an irritant contact dermatitis model, as described herein below. According to the present invention, the immunosuppressive polypeptides of the present invention are capable of reducing the ear thickening in mice challenged with phorbol 12-myristate 13-acetate (TPA), the ear thickening being reduced with at least 5%, such as least 10%, at least, 15%, at least 20%, such as at least 25%, at least 30%, at least 35%, such as at least 40%, at least 45%, such as at least 50%, at least 55%, such as at least 60%, at least 65%, such as at least 70%, at least 75%, such as at least 80%, at least 85% reduction of ear thickening following TPA challenge.

Hence, the present invention comprise one or more immunosuppressive peptides, such as 2, for example 3, such as 4, such as 5, for example 6, such as 7, such as 8, for example 9, such as 10, such as 11, for example 12, such as 13, such as 14, for example 15, such as 16, such as 17, for example 18, such as 19, such as 20 immunosuppressive peptides.

The present invention may comprise the same immunosuppressive polypeptide, or the compositions may comprise different immunosuppressive polypeptides. In one embodiment of the present invention, the immunosuppressive polypeptides are monomeric. In another embodiment of the present invention the immunosuppressive polypeptides are dimeric. In another embodiment of the present invention the immunosuppressive polypeptides are trimeric. In yet another embodiment of the present invention the immunosuppressive polypeptides are multimeric. Thus, according to the present invention the immunosuppressive polypeptides may be monomeric, homologous dimeric, heterologous dimeric, homologous trimeric, heterologous trimeric, homologous multimeric and/or heterologous multimeric. In a particular preferred embodiment the immunosuppressive polypeptides of the present invention are homologous dimeric.

Additionally, the present invention may comprise combinations of di-, tri- and/or multimeric immunosuppressive peptides. In one embodiment the present invention comprises homologues dimeric peptides in combination with other homologous dimeric peptides. In another embodiment the invention comprises homologous dimeric peptides in combination with heterologous dimeric peptides. The following combinations of peptides are also within the scope of this invention: homologous dimeric peptides with homologous trimeric, homologous dimeric with heterologous trimeric, heterologous dimeric with homologous trimeric, heterologous dimeric with heterologous trimeric, homologous dimeric with homologous multimeric, heterologous dimeric with homologous multimeric, homologous dimeric with heterologous multimeric, heterologous dimeric with heterologous multimeric, homologous trimeric with homologous multimeric, homologous trimeric with heterologous multimeric, heterologous trimeric with homologous multimeric and heterologous trimeric with heterologous multimeric immusuppressive peptides.

In certain embodiments of the present invention the immunosuppressive polypeptides are homologous dimers, such as homologous dimers formed by two of the peptides SEQ ID NO: 4, and/or two of the peptides with SEQ ID NO: 119, and/or two of the peptides with SEQ ID NO: 120, and/or two of the peptides with SEQ ID NO: 121, and/or two of the peptides with SEQ ID NO: 122, and/or two of the peptides with SEQ ID NO: 123, and/or two of the peptides with SEQ ID NO: 124, and/or two of the peptides with SEQ ID NO: 125, and/or two of the peptides with SEQ ID NO: 126. In one embodiment the monomeric peptides are cross-linked into a dimer by cross-linking the peptides N-terminal to N-terminal or C-terminal to C-terminal. I a preferred embodiment the peptides are cross-linked via a disulfide bond wherein the peptides are cross-linked C-terminal to C-terminal.

In other certain embodiments of the present invention the immunosuppressive polypeptides are heterologous dimers, such as heterologous dimers formed by two peptides in the following combinations: SEQ ID NO: 4 with SEQ ID NO: 119; and/or SEQ ID NO: 4 with SEQ ID NO: 120, and/or SEQ ID NO: 4 with SEQ ID NO: 121, and/or SEQ ID NO: 4 with SEQ ID NO:122, and/or SEQ ID NO: 4 with SEQ ID NO: 123, and/or SEQ ID NO: 4 with SEQ ID NO: 124, and/or SEQ ID NO: 4 with SEQ ID NO: 125, and/or SEQ ID NO: 4 with SEQ ID NO: 126 and/or with a sequence selected from SEQ ID NO: 119 to 126 with a sequence selected from SEQ ID NO: 119 to 126.

In one embodiment the monomeric peptides are cross-linked into a dimer by cross-linking the peptides N-terminal to N-terminal or C-terminal to C-terminal. I a preferred embodiment the peptides are cross-linked via a disulfide bond wherein the peptides are cross-linked C-terminal to C-terminal.

The immunosuppressive polypeptides of the present invention may be of different length. However, it is appreciated that the active component of the immunosuppressive peptides have a maximum length of about 100 amino acids, such as about 90 amino acids, for example about 80 amino acids, such as about 70 amino acids, such as about 60 amino acids, for example about 50 amino acids, such as 40 amino acids, for example about 35 amino acids.

In particular embodiments the length of the active component of the immunosuppressive peptides is 35 amino acids, or 34, or 33, or 32, or 31, or 30, or 29, or 28, or 27, or 26, or 25, or 24, or 23, or 22, or 21, or 20, or 19, or 18, or 17, or 16, or 15, or 14, or 13, or 12, or 11, or 10, or 9, or 8, or 7, or 6, or 5, or 4, or 3 amino acids long. Thus, the immunosuppressive peptides of the present invention have lengths and amino acid sequences corresponding to any of SEQ ID NO:1 to SEQ ID NO:287 as listed herein below. A special feature of the immunosuppressive peptides of the present invention is that they may contain an extra cysteine (Cys or C) residue, either in the N-terminal or C-terminal of the polypeptide. In a particular embodiment the cysteine residue is located in the C-terminal of the peptides. The presence and function of this cysteine residue is primarily so as to crosslink two or more polypeptides together, preferable via disulfide bonds, as described herein below. However, the function of the extra cysteine may be other than that of cross-linking. Thus, the immunosuppressive peptides of the present invention may have amino acid sequences corresponding to any of SEQ ID:1 to SEQ ID:287, and wherein the immunosuppressive peptides further contain an extra cysteine (Cys og C) residue at either the N-terminal or C-terminal of the peptide.

The immusuppressive peptides of the present invention may be a combination of the peptides corresponding to SEQ ID NO:1 to SEQ ID NO:287. Thus also comprise one part of one of the peptides Moreover, the present invention also encompasses polypeptides, wherein one or more amino acid residues are modified, wherein said one or more modification(s) are preferably selected from the group consisting of in vivo or in vitro chemical derivatization, such as but not limited to acetylation or carboxylation, glycosylation, such as glycosylation resulting from exposing the polypeptide to enzymes which affect glycosylation, for example mammalian glycosylating or deglycosylating enzymes, phosphorylation, such as modification of amino acid residues which results in phosphorylated amino acid residues, for example phosphotyrosine, phosphoserine and phosphothreonine. The polypeptide according to the invention can comprise one or more amino acids independently selected from the group consisting of naturally occurring L-amino acids, naturally occurring D-amino acids as well as non-naturally occurring, synthetic amino acids. One or more amino acid residues of the polypeptide of the present invention are modified so as to preferably improve the resistance to proteolytic degradation and stability or to optimize solubility properties or to render the polypeptide more suitable as a therapeutic agent. The invention also relates to polypeptides of the invention where blocking groups are introduced in order to protect and/or stabilize the N- and/or C-termini of the polypeptide from undesirable degradation. Such blocking groups may be selected from the group comprising but not limited to branched or non-branched alkyl groups and acyl groups, such as formyl and acetyl groups, as well substituted forms thereof, such as acetamidomethyl. The invention also relates to the following: The polypeptides according to present invention, wherein the one or more blocking groups are selected from N-terminal blocking groups comprising desamino analogs of amino acids, which are either coupled to the N-terminus of the peptide or used in place of the N-terminal amino acid residue. The polypeptide according to present invention, but not limited to wherein the one or more blocking groups are selected from C-terminal blocking groups wherein the carboxyl group of the C-terminus is either incorporated or not, such as esters, ketones, and amides, as well as descarboxylated amino acid analogues. The polypeptide according to present invention, wherein the one or more blocking groups are selected from C-terminal blocking groups comprising ester or ketoneforming alkyl groups, such as lower (C1 to C6) alkyl groups, for example methyl, ethyl and propyl, and amide-forming amino groups, such as primary amines (—NH2), and mono- and di-alkylamino groups, such as methylamino, ethylamino, dimethylamino, diethylamino, methylethylamino, and the like. The polypeptide according to present invention, wherein free amino group(s) at the N-terminal end and free carboxyl group(s) at the termini can be removed altogether from the polypeptide to yield desamino and descarboxylated forms thereof without significantly affecting the biological activity of the polypeptide. The increased properties may be achieved for example by chemical protection, i.e. by reacting the proteins and peptides of the present invention with protecting chemical groups, or by the incorporation of non-naturally occurring amino acids, e.g. D-amino acids, with the result of prolonging the half-life of the proteins and peptides of the present invention.

Cross-Linking

The immunosuppressive polypeptides of the present invention are suitably used alone, but is preferably coupled to another material or cross-linked to itself to increase its biological or immunological activity, particularly if the polypeptide is relatively short, or to achieve certain properties on the material being coupled. In a specific aspect of this invention, any or all of the immunosuppressive polypeptides may be cross-linked to increase its activity, to facilitate its delivery in vivo, and/or to render the polypeptides resistant towards hydrolysis and/or proteolysis. The cross-linked polypeptide may be formed in situ by allowing the monomers to oxidize (e.g., for disulfide bonds) or it may be synthesized by using a specific cross-linking agent.

The cross-linking between the polypeptide chains may occur at either end of the polypeptide, or in the middle of the polypeptide, depending on which end is most appropriate. For example, if the N-terminal or the C-terminal of the polypeptides comprises cysteine residues, these are preferably cross-linked by linking it to another cysteine residue on another homologous or heterologous polypeptide of the present invention, thereby forming a disulfide bond. Preferably the immunosuppressive polypeptides of the present invention are cross-linked by disulfide bonds at the C-terminal.

Polypeptide chains may be polymerized by cross-linking agents, either directly or indirectly through multifunctional polymers. Two polypeptides may be cross linked at their C- or N-termini using a multifunctional cross-linking agent. The agent is used to cross-link the terminal amino- or carboxyl groups. Generally, both terminal carboxyl groups or both terminal amino groups are crosslinked to one another, although by selection of the appropriate crosslinking agent the alpha amino group of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby cross-linking the polypeptide chains.

Additional cross-linking sites on the polypeptides, include epsilon amino groups found on lysine residues, as well as amino, imino, carboxyl, sulfhydryl and hydroxyl groups located on the side chains of internal residues of the peptides. Cross-linking through externally added cross-linking agents is obtained, e.g., using any of a number of reagents familiar to those skilled in the art, for example, via carbodiimide treatment of the polypeptides. Other non-limiting examples of suitable multifunctional cross-linking agents include 1,1-bis(diazoacetyl)-2-phenylethane; glutaraldehyde; Nhydroxysuccinimide esters such as esters with 4-azidosalicylic acid; homobifunctional imidoesters including disuccinimidyl esters such as 3,3'-dithiobis (succinimidylpropionate) and dimethyl adipimidate dihydrochloride, bifunctional maleimides such as bis-N-maleimido1,8-octane; disuccinimidyl suberate, and bis(sulfosuccinimidyl) suberate.

Heterobifunctional cross-linking reagents include those with an N-hydroxysuccinimide moiety at one end and a maleimido group on the other end; succinimidyl 4-(Nmaleimidomethyl)cyclohexane-1-carboxylate (SMCC), sulfo-SMCC, mmaleimidobenzoyl-N-hydroxysuccinimide ester (MBS); sulfo-MBS; suceinimidyl 4-(pmaleimidophenyl)butyrate (SMPB); sulfo-SMPB; N-succinimidyl(4-iodoacetyl) aminobenzoate (SIAB); sulfo-SIAB; 1-ethyl-3-(3dimethylaminopropyl)carbodiimide hydrochloride (EDC); and Nhydroxysulfosuccinimide. Cross-linking agents such as methyl-3-[(p-azido-phenyl)dithio) propioimidate yield photoactivatable intermediates which are capable of forming cross-links in the presence of light. If necessary, sensitive residues such as the side chains of the diargininyl group are protected during cross-linking and the protecting groups removed thereafter.

Polymers capable of multiple cross-linking serve as indirect cross-linking agents. For example, cyanogen bromide activated carbohydrates may be used for cross-linking the peptides herein. Cross-linking to amino groups of the peptides is accomplished by known chemistries based upon eyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde). Also useful are succinimidyl active esters, activated dithiocarbonate PEG, and 2,4,5-trichlorophenylchloroformate- or pnitrophenylchloroformate-activated PEG. Carboxyl groups are derivatized by coupling PEG-amine using carbodiimide.

Administration Forms, Formulations and Dosage Regimes

Pharmaceutical compositions containing a composition of the present invention may be prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example suspensions or topical applications such as a solution, gel, cream, lotion, shake lotion, ointment, foam, shampoo, mask or similar forms. But also patches, gazes and bandages and the like may be used for topical application of the composition of the present invention.

Whilst it is possible for the compositions or salts of the present invention to be administered as the raw chemical, it is preferred to present them in the form of a pharmaceutical formulation. Accordingly, the present invention further provides a pharmaceutical formulation, for medicinal application, which comprises a composition of the present invention or a pharmaceutically acceptable salt thereof, as herein defined, and a pharmaceutically acceptable carrier therefore.

The pharmaceutical compositions and dosage forms may comprise the compositions of the invention or its pharmaceutically acceptable salt or a crystal form thereof as the active component. The pharmaceutically acceptable carriers can be either solid, semisolid or liquid. Emulsions may be prepared in solutions in aqueous propylene glycol solutions or may contain emulsifying agents such as lecithin, sorbitan monooleate, or acacia. Aqueous solutions can be prepared by suspending or mixing the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include suspensions and emulsions, and may contain, in addition to the active component, colorants, stabilizers, buffers, artificial and natural dispersants, thickeners, and the like.

The compositions of the present invention may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkylimidazoline quaternary ammonium salts, and (e) mixtures thereof.

The formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, immediately prior to use.

Pharmaceutically Acceptable Salts

Pharmaceutically acceptable salts of the instant compositions, where they can be prepared, are also intended to be covered by this invention. These salts will be ones which are acceptable in their application to a pharmaceutical use. By that it is meant that the salt will retain the biological activity of the parent composition and the salt will not have untoward or deleterious effects in its application and use in treating diseases.

Pharmaceutically acceptable salts are prepared in a standard manner. If the parent composition is a base it is treated with an excess of an organic or inorganic acid in a suitable solvent. If the parent composition is an acid, it is treated with an inorganic or organic base in a suitable solvent.

The compositions of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Uses of Compositions Containing Said Immunosuppressive Peptides

The present invention comprises in one embodiment a pharmaceutical composition and/or compositions for the treatment and/or prevention and/or amelioration of inflammatory disorders. Below is a non-limiting list of the inflammatory disorders that the compositions of the present invention can be used to treat, prevent or ameliorate. The compositions of the present invention may be directed towards the treatment, prevention or amelioration of other inflammatory disorders than the ones listed herein below. The list below may thus be regarded as the inflammatory disorders that in preferred embodiments are target conditions for the compositions of the present invention.

We anticipate that the immunosuppressive peptides disclosed in this application will be advantageous for treatment of many other types of inflammatory disorders where a reduction of anti-inflammatory responses in the patient is desirable. This is especially valid for diseases/applications where a reduction in the level of cytokines like TNF-α, IL-17, IL-6. Especially for diseases/applications like Arthritis, Asthma, Autoimmune diseases, Sepsis, Inflammatory bowel disease, Coating of biomaterials and nanoparticles where a reduction of one or several of these cytokines has been reported as desirable.

Below a number of such inflammatory disorders where a decreased immunogenic response is required is described in more detail. The description of relevant diseases should only be considered as examples as many more diseases could be treated these immunosuppressive peptides. Also included is the usage of these immunosuppressive peptides for coating of nanoparticles and biomaterials as a decreased immunogenic response is also desired in these cases to prolong the half-life of these materials, increase biocompatibility or decrease foreign body reactions.

Sepsis

Sepsis is a potentially deadly medical condition characterized by a whole-body inflammatory state (called a systemic inflammatory response syndrome or SIRS) that is triggered by an infection. The body may develop this inflammatory response by the immune system to microbes in the blood, urine, lungs, skin, or other tissues. A lay term for sepsis is blood poisoning, also used to describe septicaemia. Severe sepsis is the systemic inflammatory response, infection and the presence of organ dysfunction.

Severe sepsis is usually treated in the intensive care unit with intravenous fluids and antibiotics. If fluid replacement isn't sufficient to maintain blood pressure, specific vasopressor medications can be used. Mechanical ventilation and dialysis may be needed to support the function of the lungs and kidneys, respectively. To guide therapy, a central venous catheter and an arterial catheter may be placed; measurement of other hemodynamic variables (such as cardiac output, mixed venous oxygen saturation, or stroke volume variation) may also be used. Sepsis patients require preventive measures for deep vein thrombosis, stress ulcers and pressure ulcers, unless other conditions prevent this. Some patients might benefit from tight control of blood sugar levels with insulin (targeting stress hyperglycemia). The use of corticosteroids (low dose or otherwise) is controversial. Activated drotrecogin alfa (recombinant protein C) has not been found to be helpful, and has recently been withdrawn from sale.

In addition to symptoms related to the provoking infection, sepsis is characterized by presence of acute inflammation present throughout the entire body, and is, therefore, frequently associated with fever and elevated white blood cell count (leukocytosis) or low white blood cell count (leukopenia) and lower-than-average temperature, and vomiting. The modern concept of sepsis is that the host's immune response to the infection causes most of the symptoms of sepsis, resulting in hemodynamic consequences and damage to organs. This host response has been termed systemic inflammatory response syndrome (SIRS) and is characterized by an elevated heart rate (above 90 beats per minute), high respiratory rate (above 20 breaths per minute or a partial pressure of carbon dioxide in the blood of less than 32), abnormal white blood cell count (above 12,000, lower than 4,000, or greater than 10% band forms) and elevated or lowered body temperature, i.e. under 36° C. (96.8° F.) or over 38° C. (100.4° F.). Sepsis is differentiated from SIRS by the presence of a known or suspected pathogen. For example SIRS and a positive blood culture for a pathogen indicates the presence of sepsis. However, in many cases of sepsis no specific pathogen is identified.

This immunological response causes widespread activation of acute-phase proteins, affecting the complement system and the coagulation pathways, which then cause damage to the vasculature as well as to the organs. Various neuroendocrine counter-regulatory systems are then activated as well, often compounding the problem. Even with immediate and aggressive treatment, this may progress to multiple organ dysfunction syndrome and eventually death.

The term "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule. Thus, the term "amino acid" comprises any synthetic or naturally occurring amino carboxylic acid, including any amino acid occurring in peptides and polypeptides including proteins and enzymes synthesized in vivo thus including modifications of the amino acids. The term amino acid is herein used synonymously with the term "amino acid residue" which is meant to encompass amino acids as stated which have been reacted with at least one other species, such as 2, for example 3, such as more than 3 other species. The generic term amino acid comprises both natural and non-natural amino acids any of which may be in the "D" or "L" isomeric form.

| One-letter symbol | Three-letter symbol | Amino acid (trivial name) |
|---|---|---|
| A | Ala | alanine |
| B | Asx | aspartic acid or asparagine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| U* | Sec | selenocysteine |
| V | Val | valine |
| W | Trp | tryptophan |
| X | Xaa | unknown or other amino acid, i.e. X can be any of the conventional amino acids. |
| Y | Tyr | Tyrosine |
| Z | Glx | glutamic acid or glutamine (or substances such as 4-carboxyglutamic acid and 5-oxoproline that yield glutamic acid on acid hydrolysis of peptides) |

The term "polypeptide" refers to a peptide having at least two, and preferably more than two amino acids. "Monomeric polypeptide" refers to a polypeptide that is a monomer as opposed to a dimer, trimer or polymer in the sense that the monomeric polypeptide is not crosslinked or otherwise bonded to another polypeptide chain. The term "dimer" thus refers to a moiety wherein two monomeric polypeptides are crosslinked to each other. In the same way, a trimeric polypeptide refers to a moiety wherein three monomeric polypeptides are crosslinked to each other, while the term "polymer" or "multimer" refers to a moiety wherein at least two polypeptides, and preferably more than three polypeptides are crosslinked to each other.

The expression "cross-linker" or "cross-linking moiety" refers to a linking moiety conferred by an external crosslinking agent used to crosslink one polypeptide with one or more polypeptides as described further in detail herein below.

The term “homology” refers to sequence similarity or, interchangeably, sequence identity, between two or more polynucleotide sequences or two or more polypeptide sequences.

The phrases “percent identity” and “% identity,” as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

“Percent identity” may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 6, at least 8, at least 10, at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The term “carrier” refers to a compound that is conjugated to the polypeptide(s) either to increase the number of polypeptides, for increasing activity or immunosuppressive effect of the polypeptide(s), to confer stability to the molecules, to increase the biological activity of the peptides, or to increase its serum half-life. The “carrier” may be a protein carrier or a non-protein carrier. Non-limiting examples of non-protein carriers include liposomes, micelles, polymeric nanoparticles and diaminoethane. The liposome may comprise glycosaminoglycan hyaluronan (HA) and/or PEG. In one embodiment, the carrier is an immunoliposome. Other carriers include protamines, or polysaccharides e.g. aminodextran or chitosan. Non-limiting examples of protein carriers include, keyhole limpet hemocyanin, serum proteins such as transferrin, bovine serum albumin, human serum albumin, whale myoglobin, ovalbumn, immunoglobulins, lysozyme, carbonic anhydrase, or hormones, such as insulin. In other embodiments of the present invention, the carrier may be a pharmaceutical acceptable carrier as described herein below. The immunosuppressive peptides of the present invention may be coupled to the carrier by means of cross-linking as further described herein below.

The terms “protein modification”, “protein stability” and “peptide stability” is used to describe the state of the immunosuppressive proteins and peptides, in particular the state wherein said proteins and/or peptides are more resistant to degradation and/or have increased properties towards hydrolysis and/or proteolysis. In particular, proteolytic stability refers to the resistance toward the action of proteolytic enzymes, also known as proteases, i.e. enzymes that catalyzes the hydrolysis of the amide/peptide-bond of the protein or peptide. Moreover, the present invention also encompasses polypeptides, wherein one or more amino acid residues are modified, wherein said one or more modification(s) are preferably selected from the group consisting of in vivo or in vitro chemical derivatization, such as but not limited to acetylation or carboxylation, glycosylation, such as glycosylation resulting from exposing the polypeptide to enzymes which affect glycosylation, for example mammalian glycosylating or deglycosylating enzymes, phosphorylation, such as modification of amino acid residues which results in phosphorylated amino acid residues, for example phosphotyrosine, phosphoserine and phosphothreonine. The polypeptide according to the invention can comprise one or more amino acids independently selected from the group consisting of naturally occurring L-amino acids, naturally occurring D-amino acids as well as non-naturally occurring, synthetic amino acids. One or more amino acid residues of the polypeptide of the present invention are modified so as to preferably improve the resistance to proteolytic degradation and stability or to optimize solubility properties or to render the polypeptide more suitable as a therapeutic agent. The invention also relates to polypeptides of the invention where blocking groups are introduced in order to protect and/or stabilize the N- and/or C-termini of the polypeptide from undesirable degradation. Such blocking groups may be selected from the group comprising but not limited to branched or non-branched alkyl groups and acyl groups, such as formyl and acetyl groups, as well substituted forms thereof, such as acetamidomethyl. The invention also relates to the following: The polypeptides according to present invention, wherein the one or more blocking groups are selected from N-terminal blocking groups comprising desamino analogs of amino acids, which are either coupled to the N-terminus of the peptide or used in place of the N-terminal amino acid residue. The polypeptide according to present invention, but not limited to wherein the one or more blocking groups are selected from C-terminal blocking groups wherein the carboxyl group of the C-terminus is either incorporated or not, such as esters, ketones, and amides, as well as descarboxylated amino acid analogues. The polypeptide according to present invention, wherein the one or more blocking groups are selected from C-terminal blocking groups comprising ester or ketoneforming alkyl groups, such as lower (C1 to C6) alkyl groups, for example methyl, ethyl and propyl, and amide-forming amino groups, such as primary amines (—NH2), and mono- and di-alkylamino groups, such as methylamino, ethylamino, dimethylamino, diethylamino, methylethylamino, and the like. The polypeptide according to present invention, wherein free amino group(s) at the N-terminal end and free carboxyl group(s) at the termini can be removed altogether from the polypeptide to yield desamino and descarboxylated forms thereof without significantly affecting the biological activity of the polypeptide. The increased properties may be achieved for example by chemical protection, i.e. by reacting the proteins and peptides of the present invention with protecting chemical groups, or by the incorporation of non-naturally occurring amino acids, e.g. D-amino acids, with the result of prolonging the half-life of the proteins and peptides of the present invention.

The term “penetration promoting” or “penetration enhancing” as used herein refers to compounds that facilitate the delivery of the immunosuppressive peptides of the present invention to the target site of action. In particular the term refers to the transcutaneous delivery of the immunosuppressive peptides. Simple topical application of the present invention may not always yield an adequate result, as the outermost layer of the skin provides an outstanding barrier against the external environment. While single penetration enhancers can aid topical delivery, combinations of several penetration enhancers may most effective. The amount of penetration enhancer which may be used in the invention varies from about 1 to 100 percent although adequate enhancement of penetration is generally found to occur in the range of about 1 to about 10 percent by weight of the formulation to be delivered. Non-limiting examples of penetration enhancers are entities that falls within liposomes, transfersomes niosomes and ethosomes, but may also be any of the many hundred known chemical prentration enhancers, of which sulfoxides, azones, pyrrolidones, fatty acids, terpenes and terpenoids, oxazolidinones and urea are non-limiting examples.

The term "immuno-modulation" as used herein refers to the process of where an immune response is either suppressed, partly or completely, or triggered or induced or enhanced. Likewise, the term "growth-modulation" as used herein refers to the process of were the cell proliferation is either suppressed, partly or completely, or where cell proliferation is induced or enhanced or promoted.

The term "substance" as used anywhere herein comprises any form of substance suitable for comprising the immunosuppressive polypeptides of the present invention.

Non-limiting examples of such substances are creams, lotions, shake lotions, ointments, gels, balms, salves, oils, foams, shampoos, sprays, aerosoloes as well as transdermal patches and bandages.

The term "treatment", as used anywhere herein comprises any type of therapy, which aims at terminating, preventing, ameliorating and/or reducing the susceptibility to a clinical condition as described herein. In a preferred embodiment, the term treatment relates to prophylactic treatment, i.e. a therapy to reduce the susceptibility of a clinical condition, a disorder or condition as defined herein.

Thus, "treatment," "treating," and the like, as used herein, refer to obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse affect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or immune deficiency.

The term "animal" as used herein may be defined to include humans, domestic or agricultural (cats, dogs, cows, sheep, horses, pigs, etc.) or test species such as mouse, rats, rabbits and the like. Thus the anamals may also be of bovine, equine, porcine, human, ovine, caprine or cervidae origin.

According to an embodiment, the present invention concerns an immune suppressive domain for use as a medicament.

According to an embodiment, the invention concerns the immune suppressive domain, wherein said domain is the fusion peptide of an envelope protein.

According to an embodiment, the invention concerns the immune suppressive domain, wherein said domain is the fusion peptide of a virus.

According to an embodiment, the invention concerns the immune suppressive domain, wherein said domain is the fusion peptide of an enveloped RNA virus.

According to an embodiment, the invention concerns the immune suppressive domain, wherein said domain is from a virus.

The inventors have inter alia identified three new groups of enveloped RNA viruses with immunosuppressive domains in their fusion protein:

1: The inventors have identified immunosuppressive domains among enveloped RNA viruses with type II fusion mechanism. Hitherto, immunosuppressive domains have not been described for any enveloped RNA viruses with a type II fusion mechanism. Immunosuppressive domains have been identified by the inventors at two positions in two different groups of viruses:

i. Co-localizing with the fusion peptide exemplified by the identification of an common immunosuppressive domain in the fusion peptide of Flavirius (Dengue virus, west Nile virus etc), and ii. In the hydrophobic alpha helix N-terminal of the transmembrane domain in the fusion protein exemplified by the finding of an immunosuppressive domain in said helixes of all flaviridae e.g. Hepatitis C virus, Dengue, west nile etc.

2: The inventors have identified immunosuppressive domains in the fusion protein among enveloped RNA viruses with type I fusion mechanism (excluding lentivirus, retrovirus and filovirus).

This position co-localizes with the fusion peptide of said fusion protein as demonstrated by the identification of a common immunosuppressive domain in the fusion peptide of all Influenza A and B types.

3: The inventors have identified potential immunosuppressive domains located at various positions of type I enveloped RNA viruses (excluding lentivirus, retrovirus and filovirus) as well as in enveloped RNA viruses featuring a fusion protein with neither a type I nor a type II fusion structure.

According to an embodiment, the invention concerns the immune suppressive domain, wherein said domain is from an influenza virus.

According to an embodiment, the invention concerns the immune suppressive domain, wherein said domain is derived from an enveloped RNA virus.

The expression "derived from a virus" means that the domain is substantially identical to the immune suppressive domain of the virus, optionally with mutations, insertions or deletions.

According to an embodiment, the invention concerns the immune suppressive domain, subject to the proviso that said immune suppressive domain is different from immunosuppressive domains obeying the conditions of:

i) being from a virus selected among the group consisting of gammaretrovirus, HIV and filovirus;
ii) being located in the linker between the two heptad repeat structures just N-terminal of the transmembrane domain in the fusion protein; and
iii) including at least some of the first 22 amino acids located N-terminal to the first cysteine residue of the two well conserved cysteine residues, located between 4 and 6 amino acid residues from one another and further located just N-terminal of the transmembrane spanning domain of the fusion protein.

The immunosuppressive domains of lentivirus, retroviruses and filoviruses show large structural similarity. Furthermore the immunosuppressive domain of these viruses are all located at the same position in the structure of the fusion protein, more precisely in the linker between the two heptad repeat structures just N-terminal of the transmembrane domain in the fusion protein. These heptad repeat regions constitute two alpha helices that play a critical role in the active mechanism of membrane fusion by these proteins. The immune suppressive domains can be located in relation to two well conserved cysteine residues that are found in these structures. These cysteine residues are between 4 and 6 amino acid residues from one another and in many cases are believed to form disulfide bridges that stabilize the fusion proteins. The immune suppressive domains in all three cases include at least some of the first 22 amino acids that are located N-terminal to the first cysteine residue.

According to an embodiment, the invention concerns the immune suppressive domain, subject to the proviso, that said immune suppressive domain is different from immunosuppressive domains obeying the conditions of:

i) being from a virus selected among the group consisting of gammaretrovirus, HIV and filovirus; and ii) being located in the linker between the two heptad repeat structures just N-terminal of the transmembrane domain in the fusion protein.

The in this context relevant immunosuppressive domains are all located at a very well-defined structure within their fusion proteins, at the bend in the heptad repeat just N-terminale of the transmembrane structure in the fusion protein.

According to an embodiment, the invention concerns the immune suppressive domain, wherein said immune suppressive domain is different from immunosuppressive domains from a virus selected among the group consisting of gammaretrovirus, HIV and filovirus.

According to an embodiment, the invention concerns the immune suppressive domain, wherein the domain is selected among the sequences of Table 1 or sequences seqid 1 to seqid 287.

According to an embodiment, the invention concerns the immune suppressive domain, wherein the domain is obtainable from the sequences of Table 1 or the sequences seqid 1 to seqid 287, by at least one mutation, deletion or insertion.

According to an embodiment, the invention concerns the immune suppressive domain, wherein the total number of mutations, deletions or insertions is selected among 1, 2, 3 and 4.

The term "mutation" is used with a number about this number of point mutation(s), i.e. 3 mutations mean 3 point mutations. The term "deletion" is used with a number about the deletion of this number of amino acid(s), i.e. 2 deletions means the deletion of 2 amino acids. The term "insertion" is used with a number about insertion of this number of amino acid(s), i.e. 1 insertion means the insertion of 1 amino acid.

According to an embodiment, the invention concerns the immune suppressive domain, wherein the total number of mutations, deletions or insertions is more than 4.

According to an embodiment, the invention concerns the immune suppressive domain, whereby the obtained immune suppressive domain have abrogated immunosuppressive properties for use in a vaccine against Porcine Reproductive and Respiratory Syndrome (PRRS).

According to an embodiment, the invention concerns the immune suppressive domain for use in surgery, prophylaxis, therapy, or a diagnostic method.

According to an embodiment, the invention concerns the immune suppressive domain, wherein the domain is selected among the group consisting of seqid 4 and seqid 119 to seqid 126.

According to an embodiment, the invention concerns the immune suppressive domain, wherein the domain is homologous to seqid 4.

According to an embodiment, the invention concerns the immune suppressive domain, which is a monomeric peptide.

According to an embodiment, the invention concerns the immune suppressive domain, cross-linked to at least one additional immunosuppressive peptide.

According to an embodiment, the invention concerns the immune suppressive domain, connected to at least one additional immunosuppressive peptide to form a dimer.

According to an embodiment, the invention concerns the immune suppressive domain, wherein said dimer is homologous and comprises at least two immunosuppressive peptides with SEQ ID NO. 4, which are cross-linked by a disulfide bond, N-terminal to N-terminal or C-terminal to C-terminal.

According to an embodiment, the invention concerns the immune suppressive domain, wherein said dimer is homologous and comprises at least two immunosuppressive peptides selected from SEQ ID NO. 119 to seqid 126, which are cross-linked by a disulfide bond, N-terminal to N-terminal or C-terminal to C-terminal.

According to an embodiment, the invention concerns the immune suppressive domain, connected to at least one additional immunosuppressive peptide to form a heterologous dimer.

According to an embodiment, the invention concerns the immune suppressive domain, connected to at least two additional immunosuppressive peptides to form a multimer.

According to an embodiment, the invention concerns the immune suppressive domain, wherein said immunosuppressive peptides comprises one or more modifications.

According to an embodiment, the invention concerns the immune suppressive domain, wherein said modifications are selected from the group consisting of chemical derivatizations, L-amino acid substitutions, D-amino acid substitutions, synthetic amino acid substitutions, deaminations and decarboxylations.

According to an embodiment, the invention concerns the immune suppressive domain, wherein the peptides or proteins have increased resistance against proteolysis compared to peptides or proteins not comprising said at least one modification.

According to an embodiment, the invention concerns the immune suppressive domain or an immune suppressive peptide according to the invention, for use in diagnostics and/or treatment and/or prevention and/or amelioration of disease.

According to an embodiment, the invention concerns the immune suppressive domain, wherein the subject is a human or an animal.

According to an embodiment, the invention concerns the immune suppressive domain, for use on an organ.

It is envisaged that an ISD may be used for treating an organ, e.g. before transplantation.

According to an embodiment, the invention concerns the immune suppressive domain for immune suppression.

According to an embodiment, the invention concerns the immune suppressive domain for the preparation or treatment of transplantation patients.

According to an embodiment, the invention concerns the immune suppressive domain for a use comprising treatment and/or prevention and/or amelioration of an autoimmune or inflammatory disease.

According to an embodiment, the invention concerns the immune suppressive domain for a use comprising prophylaxis or treatment of a condition selected among Acute disseminated encephalomyelitis (ADEM), Addison's disease, Agammaglobulinemia, Alopecia areata, Amyotrophic Lateral Sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaff's encephalitis, Blau syndrome, Bullous pemphigoid, Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis, Gastritis, Gastrointestinal pemphigoid, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura, IgA nephropathy, Inclusion body myositis, Chronic inflammatory demyelinating polyneuropathy, Interstitial cystitis, Juvenile idiopathic arthritis, Kawasaki's disease, Lambert-Eaton myasthenic syndrome, Leukocytoclastic vasculitis, Lichen planus, Lichen sclerosus, Linear IgA disease (LAD), Lou Gehrig's disease, Lupoid hepatitis, Lupus erythematosus, Majeed syndrome, Meniere's disease, Microscopic polyangiitis, Miller-Fisher syndrome, Mixed connective tissue disease, Morphea, Mucha-Habermann disease, Multiple sclerosis, Myasthenia gravis, Myositis, Narcolepsy, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome, Schnitzler syndrome, Scleritis, Scleroderma, Serum Sickness, Sjögren's syndrome, Spondyloarthropathy, Still's disease, Stiff person syndrome, Subacute bacterial endocarditis (SBE), Susac's syndrome, Sweet's syndrome, Sydenham chorea, Sympathetic ophthalmia, Systemic lupus erythematosis, Takayasu's arteritis, Temporal arteritis, Thrombocytopenia, Tolosa-Hunt syndrome, Transverse myelitis, Ulcerative colitis, Undifferentiated connective tissue disease, Undifferentiated spondyloarthropathy, Urticarial vasculitis, Vasculitis, Vitiligo, and Wegener's granulomatosis.

According to an embodiment, the invention concerns the immune suppressive domain for the treatment or prevention of acute or chronic inflammation.

According to an embodiment, the invention concerns the immune suppressive domain for the treatment or prevention of a disorder associated with inflammation.

According to an embodiment, the invention concerns the immune suppressive domain for the treatment or prevention of a disorder selected among Acne vulgaris, Allergy, Allergic rhinitis, Asthma, Atherosclerosis, Autoimmune disease, Celiac disease, Chronic prostatitis, Glomerulonephritis, Hypersensitivities, Inflammatory bowel diseases, Pelvic inflammatory disease, Reperfusion injury, Rheumatoid arthritis, Sarcoidosis, Transplant rejection, Vasculitis, interstitial cystitis, Cancer, Depression, Myopathies, and Leukocyte defects. These conditions are examples of diseases or conditions associated with inflammation.

According to an embodiment, the invention concerns the immune suppressive domain for a use comprising prophylaxis or treatment of sepsis.

According to an embodiment, the invention concerns the immune suppressive domain for a use comprising prophylaxis or treatment of asthma.

According to an embodiment, the invention concerns the immune suppressive domain for a use comprising prophylaxis or treatment of allergy.

According to an embodiment, the invention concerns the use of an immune suppressive domain for the manufacture of a medicament for immune suppression.

According to an embodiment, the invention concerns the use of an immune suppressive domain for the manufacture of a medicament for the preparation or treatment of transplantation patients.

According to an embodiment, the invention concerns the use of an immune suppressive domain for the manufacture of a medicament for prophylaxis or treatment of an autoimmune or inflammatory disease.

According to an embodiment, the invention concerns the use of an immune suppressive domain for the manufacture of a medicament for prophylaxis or treatment of a condition selected among Acute disseminated encephalomyelitis (ADEM), Addison's disease, Agammaglobulinemia, Alopecia areata, Amyotrophic Lateral Sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaff's encephalitis, Blau syndrome, Bullous pemphigoid, Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis, Gastritis, Gastrointestinal pemphigoid, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura, IgA nephropathy, Inclusion body myositis, Chronic inflammatory demyelinating polyneuropathy, Interstitial cystitis, Juvenile idiopathic arthritis, Kawasaki's disease, Lambert-Eaton myasthenic syndrome, Leukocytoclastic vasculitis, Lichen planus, Lichen sclerosus, Linear IgA disease (LAD), Lou Gehrig's disease, Lupoid hepatitis, Lupus erythematosus, Majeed syndrome, Meniere's disease, Microscopic polyangiitis, Miller-Fisher syndrome, Mixed connective tissue disease, Morphea, Mucha-Habermann disease, Multiple sclerosis, Myasthenia gravis, Myositis, Narcolepsy, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome, Schnitzler syndrome, Scleritis, Scleroderma, Serum Sickness, Sjögren's syndrome, Spondyloarthropathy, Still's disease, Stiff person syndrome, Subacute bacterial endocarditis (SBE), Susac's syndrome, Sweet's syndrome, Sydenham chorea, Sympathetic ophthalmia, Systemic lupus erythematosis, Takayasu's arteritis, Temporal arteritis, Thrombocytopenia, Tolosa-Hunt syndrome, Transverse myelitis, Ulcerative colitis, Undifferentiated connective tissue disease, Undifferentiated spondyloarthropathy, Urticarial vasculitis, Vasculitis, Vitiligo, and Wegener's granulomatosis.

According to an embodiment, the invention concerns the use of an immune suppressive domain for the manufacture of a medicament for prophylaxis or treatment of a condition selected among acute or chronic inflammation.

According to an embodiment, the invention concerns the use of an immune suppressive domain for the manufacture of a medicament for prophylaxis or treatment of a condition associated with inflammation.

According to an embodiment, the invention concerns the use of an immune suppressive domain for the manufacture of a medicament for prophylaxis or treatment of a condition selected among Acne vulgaris, Allergy, Allergic rhinitis, Asthma, Atherosclerosis, Autoimmune disease, Celiac disease, Chronic prostatitis, Glomerulonephritis, Hypersensitivities, Inflammatory bowel diseases, Pelvic inflammatory disease, Reperfusion injury, Rheumatoid arthritis, Sarcoidosis, Transplant rejection, Vasculitis, interstitial cystitis, Cancer, Depression, Myopathies, and Leukocyte defects.

According to an embodiment, the invention concerns the use of an immune suppressive domain for the manufacture of a medicament for prophylaxis or treatment of Sepsis.

According to an embodiment, the invention concerns the use of an immune suppressive domain for the manufacture of a medicament for prophylaxis or treatment of asthma.

According to an embodiment, the invention concerns the use of an immune suppressive domain for the manufacture of a medicament for prophylaxis or treatment of allergy.

According to an embodiment, the invention concerns a method for the preparation of a pharmaceutical composition comprising the steps of:

a. Providing one or more immunosuppressive peptides selected from Seqid 1 to Seqid 287, and optionally cross-linking said one or more immunosuppressive peptides;
b. Optionally providing a carrier;
c. Providing a substance;
d. Mixing the provided one or more peptides with any carrier of optional step b. and the substance of step d. to obtain the pharmaceutical composition.

According to an embodiment, the invention concerns the method, wherein said substance of step c. is selected from the group consisting of creams, lotions, shake lotions, ointments, gels, balms, salves, oils, foams, shampoos, sprays, aerosols, transdermal patches and bandages.

According to an embodiment, the invention concerns a pharmaceutical composition obtainable according to the invention.

According to an embodiment, the invention concerns a pharmaceutical composition comprising an immune suppressive domain as an active substance.

According to an embodiment, the invention concerns the pharmaceutical composition, wherein said immune suppressive domain is selected among the immune suppressive domains of the invention.

According to an embodiment, the invention concerns the pharmaceutical composition, further comprising at least one carrier.

According to an embodiment, the invention concerns the pharmaceutical composition, wherein said at least one carrier is a non-protein carrier and/or a protein carrier.

According to an embodiment, the invention concerns a use of the composition according to the invention, for treatment of a disease by IV injection.

According to an embodiment, the invention concerns the use of a composition of the invention for treatment of a disease by direct injection at a site of inflammation.

According to an embodiment, the invention concerns the use of a composition of the invention for treatment of a disease by inhalation.

According to an embodiment, the invention concerns the use of a composition of the invention for treatment of a disease by oral delivery.

According to an embodiment, the invention concerns the use of a composition of the invention for treatment of a disease by anal delivery.

According to an embodiment, the invention concerns the use of a composition of the invention for treatment of a condition selected among a skin disease, Psoriasis, Arthritis, Asthma, Sepsis and inflammatory bowel disease.

According to an embodiment, the invention concerns the use of a composition of the invention for administration in a way selected among IV, IP, and IM.

According to an embodiment, the invention concerns the use of a composition of the invention for treatment of Arthritis wherein the composition is injected directly at site of inflammation.

According to an embodiment, the invention concerns the use of a composition of the invention for treatment of a condition selected among Gastrointestinal hyperresponsiveness, Food Allergy, Food intolerance and inflammatory bowel disease, wherein the composition is delivered orally.

According to an embodiment, the invention concerns the use of a composition of the invention for treatment Asthma where the composition is delivered by inhalation.

According to an embodiment, the invention concerns the use of a composition of the invention for coating of nanoparticles and biomaterials. The immune suppressive domain may aid in suppressing any immune response e.g. from a patient treated with or subjected to nanoparticles, e.g. for drug delivery or diagnostics, or biomaterials.

According to an embodiment, the invention concerns the use of a composition of the invention to aid in suppressing any immune response to nanoparticles or biomaterials.

According to an embodiment, the invention concerns the use of a composition of the invention to increase the half-life of nanoparticles or biomaterials in vivo in a patient.

According to an embodiment, the invention concerns a vaccine comprising an immune suppressive domain, optionally mutated, for systemic immune suppression.

According to an embodiment, the invention concerns a vaccine comprising an immune suppressive domain selected among Seqid 275 to 287 against PRRS.

According to an embodiment, the invention concerns a vaccine comprising a peptide, obtained by performing at least one mutation, insertion or deletion of an immune suppressive domain selected among Seqid 275 to 287.

According to an embodiment, the invention concerns a vaccine against PRRS comprising a mutated immunosuppressive domain selected among seqid 275 to seqid 287, subject to the proviso that the immunosuppressive properties of said domain have been abrogated.

According to an embodiment, the invention concerns a peptide having the sequence of the Immune Suppressive Domain according to the invention.

According to an embodiment, the invention concerns the peptide having the sequence of the Immune Suppressive Domain according to the invention, modified by a number of point mutations selected among 1, 2, 3, 4, 5, 6, 7, 8, 9, and 10.

According to an embodiment, the invention concerns the peptide having the sequence of the Immune Suppressive Domain according to the invention, modified by a number of point deletions selected among 1, 2, 3, 4, 5, 6, 7, 8, 9, and 10.

According to an embodiment, the invention concerns the peptide having the sequence of the Immune Suppressive Domain according to the invention, modified by a number of point insertions selected among 1, 2, 3, 4, 5, 6, 7, 8, 9, and 10.

According to an embodiment, the invention concerns the peptide according to the invention, capable of an inhibition selected among at least 5% inhibition of T-lymphocyte proliferation, at least 10%, at least 20%, such as at least 30%, at least 40%, at least 50%, such as at least 60%, such as at least 70% inhibition of T-lymphocyte proliferation, at least 75% inhibition of T-lymphocyte proliferation, at least 80%, such as at least 85%, at least 90%, such as at least 95%, at least 97%, such as at least 99%, and at least 100% inhibition of T-lymphocyte proliferation.

According to an embodiment, the invention concerns a peptide according to the invention, capable of suppressing the immune response in an animal, preferably according to the TPA model.

According to an embodiment, the invention concerns the use of a peptide according to the invention, for a use selected among any of the uses of the invention.

According to an embodiment, the invention concerns a method of treatment of an indication selected among the indications of the present application and the viral infections of Table 1 comprising administration of an effective amount of an entity selected among the Immune Suppressive Domains of the invention, the compositions of the invention, and the peptides of the invention.

The co-pending patent application PCT/DK2012/050381 provides a number of immunosuppressive domains. Table 1 is provided below. Sequences of the table are applicable for the purposes of the present invention. Viral of the table provide examples of relevant indications for the present invention.

TABLE 1

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| Flavi-viridae | Flavi-virus | Aroa virus | Bussuquara virus<br>guape virus<br>Naranjal virus | seqid85<br>NRGWNNGCGLFGKG<br>**************<br>seqid7<br>GDAAWDFGSVGGVFNSLGK<br>**o****o*****oo*o** | | Envelope protein prME Fusion protein E | Group 1<br>Type II<br>Fusion mechanism |
| | | Dengue virus | Dengue 1 | seqid8<br>GGTAWDFGSIGGVFTSVGK<br>*o***************** | seqid2<br>DRGWGNGCGLFGKG<br>**************<br>seqid172<br>KGSSIGKMFESTYRGAKRMAILG | | |
| | | | Dengue 2 | seqid9<br>GDTAWDFGSLGGVFTSVGK<br>****************o**<br>seqid173<br>KGSSIGKMFEATARGARRMAILG | seqid2<br>DRGWGNGCGLFGKG<br>************** | | |
| | | | Dengue 3 | seqid174<br>KGSSIGQMFETTMRGAKRMAILG | seqid2<br>DRGWGNGCGLFGKG<br>**************<br>seqid204<br>GDTAWDFGSVGGVL<br>NSLGK<br>**************<br>***** | | |
| | | | Dengue 4 | seqid10<br>GETAWDFGSVGGLLTSLGK<br>************oo*****<br>seqid173<br>KGSSIGKMFEATARGARRMAILG | seqid2<br>DRGWGNGCGLFGKG<br>************** | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | Japanese encephalitis virus group | Japanese encephalitis virus | seqid11<br>LGDTAWDFGSIGGVFNSIG<br>***o*************** | seqid2<br>DRGWGNGCGLFGKG<br>************** | | |
| | | | Koutango virus | seqid12<br>LGDTAWDFGSVGGIFTSLG | seqid2<br>DRGWGNGCGLFGKG<br>************** | | |
| | | | Murray Valley encephalitis virus | seqid13<br>LGDTAWDFGSVGGVFNSIG | seqid2<br>DRGWGNGCGLFGKG<br>************** | | |
| | | | St. Louis encephalitis virus | seqid11<br>LGDTAWDFGSIGGVFNSIG<br>******************* | seqid2<br>DRGWGNGCGLFGKG<br>************** | | |
| | | | Usutu virus | seqid14<br>LGDTAWDFGSVGGIFNSVG<br>******************* | seqid2<br>DRGWGNGCGLFGKG<br>************** | | |
| | | | West Nile virus | seqid15<br>LGDTAWDFGSVGGVFTSVG<br>*********o********* | seqid2<br>DRGWGNGCGLFGKG<br>************** | | |
| | | Kokobera virus group | Kokobera virus unclassified Kokobera virus group | seqid16<br>IGDDAWDFGSVGGILNSVG | seqid2<br>DRGWGNGCGLFGKG | | |
| | | Modoc virus group | Modoc virus | seqid17<br>VGSAFWNSDQRFSAINLMD<br>seqid18<br>DRGWGNGCALFGKG | | | |
| | | | Cowbone Ridge virus<br>Jutiapa virus | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | Sal Vieja virus<br>San Perlita virus | | | | |
| | | mosquito-borne viruses | Ilheus virus | seqid84<br>LGDTAWDFGSVGGIFNSIG | seqid2<br>DRGWGNGCGLFGKG | | |
| | | | Sepik virus | seqid19<br>TGEHSWDFGSTGGFFASVG | seqid2<br>DRGWGNGCGLFGKG | | |
| | | Ntaya virus group | Bagaza virus | seqid20<br>LGDTAWDFGSVGGFFTSLG | seqid2<br>DRGWGNGCGLFGKG | | |
| | | | Tembusu virus | seqid83<br>LGDTAWDFGSVGGVLTSIG | seqid2<br>DRGWGNGCGLFGKG | | |
| | | | Yokose virus | seqid21<br>IGDDAWDFGSTGGIFNTIG | seqid2<br>DRGWGNGCGLFGKG | | |
| | | Rio Bravo virus group | Apoi virus | seqid22<br>SSAFWNSDEPFHFSNLISII | seqid2<br>DRGWGNGCGLFGKG | | |
| | | | Entebbe bat virus | seqid23<br>GDDAWDFGSTGGIFNTIGKA | seqid2<br>DRGWGNGCGLFGKG | | |
| | | | Rio Bravo virus | seqid24<br>SSAYWSSSEPFTSAGIMRIL | seqid2<br>DRGWGNGCGLFGKG | | |
| | | | Saboya virus | seqid18<br>DRGWGNGCALFGKG<br>seqid25<br>GSSSWDFSSAGGFFGSIGKA | | | |
| | | Seaborne tick-borne virus group | Meaban virus | seqid26<br>GDAAWDFGSVGGFMTSIGRA<br>seqid27<br>DRGWGNHCGLFGKG | | | |
| | | | Saumarez Reef virus | seqid28<br>GETAWDFGSAGGFFTSVGRG | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | seqid27<br>DRGWGNHCGLFGKG | | | |
| | | | Tyuleniy virus | seqid29<br>GEAAWDFGSAGGFFQSVGRG<br>seqid27<br>DRGWGNHCGLFGKG | | | |
| | | Spondweni virus group | Zika virus | seqid30<br>LGDTAWDFGSVGGVFNSLGK<br>*************oo**o** | seqid2<br>DRGWGNGCGLFGKG | | |
| | | | Kyasanur forest disease virus | seqid31<br>VGEHAWDFGSVGGMLSSVG<br>*************o*****<br>seqid27<br>DRGWGNHCGLFGKG | | | |
| | | | Langat virus | seqid32<br>VLGEHAWDFGSVGGVMTSIG<br>seqid27<br>DRGWGNHCGLFGKG | | | |
| | | | Louping ill virus | seqid33<br>IGEHAWDFGSAGGFFSSIG<br>**********o***oo*o*<br>seqid27<br>DRGWGNHCGLFGKG | | | |
| | | | Omsk hemorrhagic fever virus | seqid34<br>LGEHAWDFGSTGGFLSSIG<br>seqid27<br>DRGWGNHCGLFGKG | | | |
| | | | Powassan virus | seqid35<br>VGEHAWDFGSVGGILSSVG<br>*************o*****<br>seqid36<br>DRGWGNHCGFFGKG<br>************* | | | |
| | | | Royal Farm virus | seqid27<br>DRGWGNHCGLFGKG | | | |
| | | | Tick-borne encephalitis virus | seqid37<br>IGEHAWDFGSAGGFLSSIG<br>seqid38 | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | IGEHAWDFGSTGGFLTSVG<br>seqid39<br>IGEHAWDFGSTGGFLASVG<br>seqid27<br>DRGWGNHCGLFGKG | | | |
| | | Yaounde virus | | seqid40<br>LGDTAWDFGSIGGVFTSLG | seqid2<br>DRGWGNGCGLFGKG | | |
| | | Yellow fever virus group | Banzi virus | seqid41<br>VGSSSWDFSSTSGFFSSVG | seqid2<br>DRGWGNGCGLFGKG | | |
| | | | Bouboui virus | seqid42<br>VGRSSWDFSSAGGFFSSVG | seqid2<br>DRGWGNGCGLFGKG | | |
| | | | Edge Hill virus<br>Uganda S virus<br>Wesselsbron virus | | | | |
| | | | Yellow fever virus | seqid43<br>MGDTAWDFSSAGGFFTSVG<br>***o*************** | seqid2<br>DRGWGNGCGLFGKG | | |
| | | unclassified Flavivirus | Batu Cave virus<br>Cacipacore virus<br>Calbertado virus<br>Cell fusing agent virus<br>Chaoyang virus<br>Chimeric Tick-borne encephalitis virus/Dengue virus 4<br>Culex theileri flavivirus<br>Donggang virus<br>Duck hemorrhagic ovaritis virus<br>Flavivirus Aedes/ MO-Ac/ITA/2009<br>Flavivirus Anopheles/PV-Am/ ITA/2009<br>Flavivirus CbaAr4001<br>Flavivirus FSME<br>Flavivirus Phlebotomine/76/ | seqid44<br>NRGWGTGCFKWGIG<br>seqid45<br>NRGWGTGCFEWGLG | seqid2<br>DRGWGNGCGLFGKG | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | Arrabida/2007 | | | | |
| | | | Gadgets Gully virus | | | | |
| | | | Greek goat encephalitis virus | | | | |
| | | | Jugra virus | | | | |
| | | | Kadam virus | | | | |
| | | | Kamiti River virus | | | | |
| | | | Kedougou virus | | | | |
| | | | Montana myotis leukoencephalitis virus | | | | |
| | | | Mosquito flavivirus | | | | |
| | | | Ngoye virus | | | | |
| | | | Nounane virus | | | | |
| | | | Phlebotomus flavivirus Alg_F19 | | | | |
| | | | Phlebotomus flavivirus Alg_F8 | | | | |
| | | | Quang Binh virus | | | | |
| | | | Russian Spring-Summer encephalitis virus | | | | |
| | | | Sokoluk virus | | | | |
| | | | Spanish sheep encephalitis virus | | | | |
| | | | T'Ho virus | | | | |
| | | | Tai forest virus B31 | | | | |
| | | | Tamana bat virus | | | | |
| | | | Tick-borne flavivirus | | | | |
| | | | Wang Thong virus | | | | |
| | | | Flavivirus sp. | | | | |
| | | | Aedes flavivirus | seqid45 NRGWGTGCFEWGLG seqid46 HVAGRYSKHGMAGIGSVWEDLVR | | | |
| | | | Culex flavivirus | seqid44 NRGWGTGCFKWGIG seqid47 VDKYRRFGTAGVGG | | | |
| | Hepaci virus | Hepatitis C virus | Hepatitis C virus genotype 1a | | seqid3 GLIHLHQNIVDVQYLYG seqid175 PALSTGLIHLHQNIVDVQ | E1/E2 | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | Hepatitis C virus genotype 1b | seqid48 GLIHLHRNIVDVQYLYG seqid176 PALSTGLIHLHRNIVDVQ | | | |
| | | | Hepatitis C virus genotype 2 | seqid49 GLIHLHQNIVDVQYMYG seqid175 PALSTGLIHLHQNIVDVQ | | | |
| | | | Hepatitis C virus genotype 3 | seqid175 PALSTGLIHLHQNIVDVQ | seqid3 GLIHLHQNIVDVQYLYG | | |
| | | | Hepatitis C virus genotype 4 | seqid175 PALSTGLIHLHQNIVDVQ | seqid3 GLIHLHQNIVDVQYLYG | | |
| | | | Hepatitis C virus genotype 5 | seqid50 GLIHLHQNIVDTQYLYG seqid177 PALSTGLIHLHQNIVDTQ | | | |
| | | | Hepatitis C virus genotype 6 | seqid175 PALSTGLIHLHQNIVDVQ | seqid3 GLIHLHQNIVDVQYLYG | | |
| | | | All Hepatitis C virus | | seqid3 GLIHLHQNIVDVQYLYG | | |
| | Pesti virus | Border disease virus | Border disease virus - Border disease virus - X818 Border disease virus 1 Border disease virus 2 Border disease virus 3 Border disease virus isolates | seqid51 NTTLLNGSAFQLICPYGWVGRVEC seqid52 SYFQQYMLKGQYQYWFDLE | | E1/E2 | |
| | | Bovine viral diarrhea virus 1 | Bovine viral diarrhea virus 1-CP7 Bovine viral diarrhea virus 1-NADL Bovine viral | seqid53 NTTLLNGPAFQMVCPLGWTGTVSC seqid54 SYFQQYMLKGEYQYWFDLE | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | diarrhea virus 1-Osloss<br>Bovine viral diarrhea virus 1-SD1<br>Bovine viral diarrhea virus isolates and strains<br>Bovine viral diarrhea virus type 1a<br>Bovine viral diarrhea virus type 1b<br>Pestivirus isolate 97-360<br>Pestivirus isolate Hay 87/2210<br>Pestivirus strain mousedeer<br>Pestivirus type 1 isolates | | | | |
| | | Bovine viral diarrhea virus 2 (BVDV-2) | Bovine viral diarrhea virus 2<br>Pestivirus sp. strain 178003<br>Pestivirus sp. strain 5250Giessen-3<br>Bovine viral diarrhea virus-2 isolate SCP | seqid55<br>SLLNGPAFQMVCPQGWTGTIEC<br>seqid56<br>DRYFQQYMLKGKWQYWFDLD | | | |
| | | Classical swine fever virus | Classical swine fever virus<br>Hog cholera virus strain Zoelen | seqid57<br>TLLNGSAFYLVCPIGWTGVIEC<br>seqid58<br>SYFQQYMLKGEYQYWFDLD | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | unclassified Pestivirus | Bovine viral diarrhea virus 3 | seqid59<br>TLLNGPAFQLVCPYGWTGTIEC<br>seqid60<br>DNYFQQYMLKGKYQYWFDLEATD | | | |
| | | | Chamois pestivirus 1 | seqid61<br>TLLNGSAFQMVCPFGWTGQVEC<br>seqid62<br>DSYFQQYMLKGEYQYWFDLDAKD | | | |
| | | | Porcine pestivirus isolate Bungowannah | seqid205<br>TLLNGPAFQLVCPYGWTGTIECDSYYQQYIIK<br>SGYQYWFDLTAKD | | | |
| | Unnclassified Flaviviridae | | Barkedji virus<br>Canine hepacivirus AAK-2011<br>GB virus A<br>Douroucouli hepatitis GB virus A<br>GBV-A-like agents<br>GB virus D<br>GBV-C/HGV group<br>GB virus C<br>Hepatitis GB virus C-like virus<br>Hepatitis GB virus B<br>Lammi virus<br>Marmoset hepatitis GB virus A<br>Nakiwogo virus<br>Turkey meningoencephalitis virus | | | | |
| Togaviridae | Alpha-virus | Aura virus<br>Barmah Forest virus<br>Middelburg virus<br>Ndumu virus<br>Salmon pancreas disease virus<br>Getah virus | | seqid63<br>GVYPFMWGGAYCFCDTENTQVS<br>**********o****o**o*o*<br>seqid64<br>APFGCEIYTNPIRAENCAVGSIP<br>*****o*ooo*o**oo*oo*oo*<br>seqid65<br>SDFGGIATVKYSASKSGKCAVH<br>o***oooooo*ooooo*o*oo* | | | E2/E1 |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | Mayaro virus<br>Trocara virus<br>EEEV complex | | seqid66<br>FSTANIHPEFRLQICTSYVTCKGDCHPP<br>*oooooooo*oooo*ooooo*ooo*o** | | | |
| | | WEEV complex | Fort Morgan virus<br>Highlands J virus<br>Sindbis virus<br>Western equine encephalomyelitis virus<br>Whataroa virus | | | | |
| | | VEEV complex | Cabassou virus<br>Mucambo virus<br>Pixuna virus | | | | |
| | | | Venezuelan equine encephalitis virus | seqid67<br>GVYPFMWGGAYCFCD<br>***************<br>seqid68<br>GDCHPPKDHIVTHPQYHAQ<br>************o**o*o*<br>seqid69<br>AVSKTAWTWLTS<br>*********oo* | | | |
| | | SFV complex | Bebaru virus<br>O'nyong-nyong virus<br>Ross River virus<br>Semliki forest virus<br>Una virus | seqid63<br>GVYPFMWGGAYCFCDTENTQVS<br>**********o****o**o*o*<br>seqid64<br>APFGCEIYTNPIRAENCAVGSIP<br>*****o*ooo*o**oo*oo*oo*<br>seqid65<br>SDFGGIATVKYSASKSGKCAVH<br>o***oooooo*ooooo*o*oo*<br>seqid66<br>FSTANIHPEFRLQICTSYVTCKGDCHPP<br>*oooooooo*oooo*ooooo*ooo*o** | | | |
| | | | Chikungunya virus | seqid67<br>GVYPFMWGGAYCFCD<br>***************<br>seqid70<br>VHCAAECHPPKDHIVNY<br>oo*o*o**o******** | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | seqid71<br>PASHTTLGVQDISATAMSWV<br>o****oo******o****** | | | |
| | Rubivirus | Rubella virus | Rubella virus (strain BRD1)<br>Rubella virus (strain BRDII)<br>Rubella virus (strain Cendehill)<br>Rubella virus (strain M33)<br>Rubella virus (strain RN-UK86)<br>Rubella virus (strain THERIEN)<br>Rubella virus (strain TO-336 vaccine)<br>Rubella virus (strain TO-336)<br>Rubella virus (vaccine strain RA27/3) | seqid72<br>ACTFWAVNAYSSGGYAQLASYFNPGGSYYK<br>***o*o****o**oo****o**o******o<br>seqid73<br>QYHPTACEVEPAFGHSDAACWGEPTDT<br>***o*o*o*o****o********o***<br>seqid74<br>MSVFALASYVQHPHKTVRVKFHT<br>***oo*****o**o**o******<br>seqid159<br>ETRTVWQLSVAGVSC<br>o*o*********oo*<br>seqid76<br>NVTTEHPFCNMPHGQLEVQVPP<br>o*o*o**oo*o*o****o*oo*<br>seqid77<br>DPGDLVEYIMNYTGNQQSRW<br>****o******o*o******<br>seqid78<br>GSPNCHGPDWASPVCQRHSPDCS<br>****o***o**************<br>seqid79<br>RLVGATPERPRLRLV<br>o***o**o**o****<br>seqid80<br>DADDPLLRTAPGP<br>*oo**********<br>seqid81<br>GEVWVTPVIGSQARKCGL<br>oo*o**o**o*****o**<br>seqid86<br>HIRAGPYGHATVEM<br>oo***********o<br>seqid87<br>PEWIHAHTTSDPWHP<br>o**oooo*o***o*o<br>seqid88<br>PGPLGLKFKTVRPVALPR<br>****o***o**o*oo***<br>seqid89<br>ALAPPRNVRVTGCYQCGTPAL<br>oooo**o*o*o**o*******<br>seqid90 | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | EGLAPGGGNCHLTVNGEDVG<br>***o*****o**oo*o*oo*<br>seqid207<br>LLNTPPPYQVSCGG<br>******o*o*o***<br>seqid92<br>RASARVIDPAAQSFTGVVYGTHT<br>**o***oo*o*************<br>seqid93<br>TAVSETRQTWAEWAAAHWWQLTLG<br>o*******ooo*****o******* | | | |
| Bunya-viridae | Hanta-virus (continued on next page) | Amur virus<br>Bayou virus<br>Black Creek<br>Canal virus<br>Cano Delgadito virus<br>Calabazo virus<br>Catacamas virus<br>Choclo virus<br>Dobrava-Belgrade virus<br>El Moro Canyon virus<br>Hantaan virus<br>Isla Vista virus<br>Khabarovsk virus<br>Laguna Negra virus<br>Limestone Canyon virus<br>Monongahela virus<br>Muleshoe virus<br>Muju virus<br>New York virus<br>Oran virus<br>Playa de Oro virus<br>Prospect Hill virus<br>Puumala virus<br>Rio Mamore virus<br>Rio Segundo virus<br>Saaremaa virus | | seqid94<br>NPPDCPGVGTGCTACGVYLD<br>**o****o********o***<br>seqid95<br>RKVCIQLGTEQTCKTIDSNDC<br>*oo*o*o*o*oo**oo*o***<br>seqid96<br>DTLLFLGPLEEGGMIFKQWCTTTCQ<br>FGDPGDIM<br>seqid97<br>GSFRKKCSFATLPSCQYDGNTVSG<br>*o***o*o***o*o*ooo**oo**<br>seqid98<br>ATKDSFQSFNITEPH<br>**o****o**oooo*<br>seqid99<br>GSGVGFNLVCSVSLTEC<br>******o*o*ooo****<br>seqid100<br>KACDSAMCYGSSTANLVRGQNT<br>****o*o***ooooo*o**o**<br>seqid101<br>GKGGHSGSKFMCCHDKKCSATGLVAAAPHL<br>********o*o***ooo*ooo**o*oo***<br>seqid102<br>DDGAPQCGVHCWFKKSGEW<br>***o*o*ooo***oo**** | | | Gn(G2)/<br>Gc(G1) |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | Seoul virus<br>Sin Nombre virus<br>Soochong virus<br>Thailand virus<br>Thottapalayam virus<br>Topografov virus<br>Tula virus | | | | | |
| | Ortho-bunya-virus | Anopheles A virus<br>Anopheles B virus<br>Bakau virus<br>Batama virus<br>Bwamba virus<br>Caraparu virus<br>Kaeng Khoi virus<br>Kairi virus<br>Madrid virus<br>Main Drain virus<br>Marituba virus<br>Nyando virus<br>Oriboca virus<br>Oropouche virus<br>Sathuperi virus<br>Shamonda virus<br>Shuni virus<br>Simbu virus<br>Tacaiuma virus<br>Tete virus<br>Turlock virus<br>unclassified Orthobunyavirus | | seqid103<br>KHDELCTGPCPVNINHQTGWLT<br>*o*o***o**oooooooo*o*o<br>seqid104<br>WGCEEFGCLAVSDGCVFGSCQD<br>**o*oo**o*000**oo*****<br>seqid105<br>GNGVPRFDYLCHLASRKEVIVRKC<br>*o*ooo*ooo*oooo*ooooo*o*<br>seqid106<br>SCAGCINCFQNIHC<br>*o**ooooooooo* | | | |
| | | Akabane virus | Sabo virus<br>Tinaroo virus<br>Yaba-7 virus | | | | |
| | | Bunyamwera virus | Batai virus<br>Birao virus<br>Bozo virus<br>Cache Valley virus<br>Fort Sherman virus<br>Germiston virus<br>Guaroa virus<br>Iaco virus | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/fusion protein | IU group and fusion type |
|---|---|---|---|---|---|---|---|
| | | | Ilesha virus | | | | |
| | | | Lokern virus | | | | |
| | | | Maguari virus | | | | |
| | | | Mboke virus | | | | |
| | | | Ngari virus | | | | |
| | | | Northway virus | | | | |
| | | | Playas virus | | | | |
| | | | Potosi virus | | | | |
| | | | Shokwe virus | | | | |
| | | | Tensaw virus | | | | |
| | | | Tlacotalpan virus | | | | |
| | | | Xingu virus | | | | |
| | | California Encephalitis virus | California encephalitis serogroup virus LEIV | | | | |
| | | | California encephalitis virus - BFS-283 | | | | |
| | | | Chatanga virus | | | | |
| | | | Inkoo virus | | | | |
| | | | Jamestown Canyon virus | | | | |
| | | | Jamestown Canyon-like virus | | | | |
| | | | Jerry Slough virus | | | | |
| | | | Keystone virus | | | | |
| | | | La Crosse virus | | | | |
| | | | Lumbo virus | | | | |
| | | | Melao virus | | | | |
| | | | Morro Bay virus | | | | |
| | | | San Angelo virus | | | | |
| | | | Serra do Navio virus | | | | |
| | | | Snowshoe hare virus | | | | |
| | | | South River virus | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | Tahyna virus<br>Trivittatus virus | | | | |
| | | Caraparu virus | Apeu virus<br>Bruconha virus<br>Ossa virus<br>Vinces virus | | | | |
| | | Manzanilla virus | Buttonwillow virus<br>Ingwavuma virus<br>Mermet virus | | | | |
| | | Marituba virus | Gumbo<br>Limbo virus<br>Murutucu virus<br>Nepuyo virus<br>Restan virus | | | | |
| | | Wyeomyia virus | Anhembi virus<br>BeAr328208 virus<br>Macaua virus<br>Sororoca virus<br>Taiassui virus | | | | |
| | Phlebovirus | Bujaru virus<br>Candiruvirus<br>Chilibre virus<br>Frijoles virus<br>Punta Tor/Salehabad virus<br>Sandflyfever Naples virus<br>Uukuniemi viruso virus | | | | | |
| | | Rift Valley fever virus | | seqid107<br>KTVSSELSCREGQSYWT | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | **oo**oo*o**o*o**<br>seqid108<br>GSFSPKCLSSRRC<br>*******oooooo<br>seqid109<br>ENKCFEQCGGWGCGCFNVNPSCLFVHT<br>**o*o**o*oo*oo***ooo***o**o<br>seqid110<br>WGSVSLSLDAEGISGSNSFSF<br>**ooo*o**o*o*o*o*oo**<br>seqid111<br>RQGFLGEIRCNSE<br>*o*****o**oo*<br>seqid112<br>AHESCLRAPNLVSYKPMIDQLEC<br>*oo**oo**oooo*o*oo*ooo*<br>seqid113<br>DPFVVFERGSLPQTR<br>**ooo*oo*o***o*<br>seqid114<br>QAFSKGSVQADLTLMFD<br>**ooo*ooo*oooooo*<br>seqid115<br>CDAAFLNLTGCYSCNAG<br>*o*o*o*oo*****oo*<br>seqid116<br>CQILHFTVPEVEEEEMYSC<br>*ooo*ooo*ooooooo*o*<br>seqid117<br>STVVNPKSGSWN<br>*o*o**oooooo<br>seqid118<br>FFDWFSGLMSWFGGPLK<br>*o***oo*o**oooooo | | | |
| | | unclassified Phlebovirus (continued on next page) | Anhanga virus<br>Arumowot virus<br>Chagres virus<br>Corfou virus<br>Gabek Forest virus<br>Itaporanga virus<br>Phlebovirus Adria/ALB1/2005<br>Phlebovirus Adria/ALB5/2005 | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | Phlebovirus AH12 | | | | |
| | | | Phlebovirus AH12/China/2010 | | | | |
| | | | Phlebovirus AH15/China/2010 | | | | |
| | | | Phlebovirus B105-05 | | | | |
| | | | Phlebovirus B151-04 | | | | |
| | | | Phlebovirus B43-02 | | | | |
| | | | Phlebovirus B68-03 | | | | |
| | | | Phlebovirus B79-02 | | | | |
| | | | Phlebovirus Chios-A | | | | |
| | | | Phlebovirus Cyprus | | | | |
| | | | Phlebovirus HB29/China/2010 | | | | |
| | | | Phlebovirus HN13/China/2010 | | | | |
| | | | Phlebovirus HN6/China/2010 | | | | |
| | | | Phlebovirus Hu/Xinyang1/ China/2010 | | | | |
| | | | Phlebovirus Hu/Xinyang2/ China/2010 | | | | |
| | | | Phlebovirus IB13-04 | | | | |
| | | | Phlebovirus JS2007-01 | | | | |
| | | | Phlebovirus JS24 | | | | |
| | | | Phlebovirus JS26 | | | | |
| | | | Phlebovirus JS3/China/2010 | | | | |
| | | | Phlebovirus JS4/China/2010 | | | | |
| | | | Phlebovirus JS6 | | | | |
| | | | Phlebovirus | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/fusion protein | IU group and fusion type |
|---|---|---|---|---|---|---|---|
| | | | JSD1 | | | | |
| | | | Phlebovirus LN2/China/2010 | | | | |
| | | | Phlebovirus LN3/China/2010 | | | | |
| | | | Phlebovirus sandflies/Gr29/Spain/2004 | | | | |
| | | | Phlebovirus sandflies/Gr36/Spain/2004 | | | | |
| | | | Phlebovirus sandflies/Gr44/Spain/2004 | | | | |
| | | | Phlebovirus sandflies/Gr49/Spain/2004 | | | | |
| | | | Phlebovirus sandflies/Gr52/Spain/2004 | | | | |
| | | | Phlebovirus sandflies/Gr65/Spain/2004 | | | | |
| | | | Phlebovirus sandflies/Gr98/Spain/2004 | | | | |
| | | | Phlebovirus SD24/China/2010 | | | | |
| | | | Phlebovirus SD4/China/2010 | | | | |
| | | | Phlebovirus tick/XCQ-2011 | | | | |
| | | | Phlebovirus XLL/China/2009 | | | | |
| | | | Rio Grande virus | | | | |
| | | | Salobo virus | | | | |
| | | | Sandfly fever sicilian virus | | | | |
| | | | Sandfly Sicilian Turkey virus | | | | |
| | | | Utique virus | | | | |
| | | | Phlebovirus sp. | | | | |
| | | | Phlebovirus sp. Be An 24262 | | | | |
| | | | Phlebovirus sp. Be An 356637 | | | | |
| | | | Phlebovirus sp. | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | Be An 416992<br>Phlebovirus sp.<br>Be An 578142<br>Phlebovirus sp.<br>Be Ar 371637<br>Phlebovirus sp.<br>Co Ar 170255<br>Phlebovirus sp.<br>Co Ar 171616<br>Phlebovirus sp.<br>GML 902878<br>Phlebovirus sp.<br>Pa Ar 2381<br>Phlebovirus sp.<br>PAN 479603<br>Phlebovirus sp.<br>PAN 483391<br>Phlebovirus sp.<br>VP-161A<br>Phlebovirus sp.<br>VP-334K<br>Phlebovirus sp.<br>VP-366G | | | | |
| Orthomyxo-viridae | Influenza-virus A | Influenza A virus | INFA H1 | seqid119<br>GLFGAIAGFIEGGWTG<br>seqid178<br>WTYNAELLVLLENERTLD<br>seqid179<br>NAELLVLLENERTLDYHD | | INF F/2<br>DELTA6:<br>seqid201<br>GLFGAAGF<br>IENGWEG<br>InFAH1-3: | HA<br>(HA1/HA2) |
| | | | INFA H2 | seqid120<br>GLFGAIAGFIEGGWQG<br>seqid180<br>WTYNAELLVLMENERTLD<br>seqid181<br>NAELLVLMENERTLDYHD | | seqid203 | |
| | | | INFA H3 | seqid121<br>GIFGAIAGFIENGWEG<br>seqid182<br>WSYNAELLVALENQHTID<br>seqid183<br>NAELLVALENQHTIDLTD | seqid4<br>GLFGAIAGFIENGWEG | | |
| | | | INFA H4 | seqid122<br>GLFGAIAGFIENGWQG | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | seqid182 WSYNAELLVALENQHTID seqid184 NAELLVALENQHTIDVTD | | | |
| | | | INFA H5 | seqid120 GLFGAIAGFIEGGWQG seqid180 WTYNAELLVLMENERTLD seqid185 NAELLVLMENERTLDFHD | | | |
| | | | INFA H6 | seqid123 GIFGAIAGFIEGGWTG seqid119 GLFGAIAGFIEGGWTG seqid178 WTYNAELLVLLENERTLD seqid186 NAELLVLLENERTLDMHD | | | |
| | | | INFA H7 | seqid187 WSYNAELLVAMENQHTID seqid208 WSYNAELLVAMENQHLAD | seqid4 GLFGAIAGFI ENGWEG | | |
| | | | INFA H8 | seqid124 GLFGAIAGFIEGGWSG seqid189 WAYNAELLVLLENQKTLD seqid190 NAELLVLLENQKTLDEHD | | | |
| | | | INFA H9 | seqid125 GLFGAIAGFIEGGWPG seqid124 GLFGAIAGFIEGGWSG seqid189 WAYNAELLVLLENQKTLD seqid190 NAELLVLLENQKTLDEHD | | | |
| | | | INFA H10 | seqid191 WTYQAELLVAMENQHTID seqid192 QAELLVAMENQHTIDMAD | seqid4 GLFGAIAGFI ENGWEG | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | INFA H11 | seqid125<br>GLFGAIAGFIEGGWPG<br>seqid193<br>WSYNAQLLVLLENEKTLD<br>seqid194<br>NAQLLVLLENEKTLDLHD | | | |
| | | | INFA H12 | seqid125<br>GLFGAIAGFIEGGWPG<br>seqid189<br>WAYNAELLVLLENQKTLD<br>seqid190<br>NAELLVLLENQKTLDEHD | | | |
| | | | INFA H13 | seqid125<br>GLFGAIAGFIEGGWPG<br>seqid195<br>WSYNAKLLVLLENDKTLD<br>seqid196<br>NAKLLVLLENDKTLDMHD | | | |
| | | | INFA H14 | seqid122<br>GLFGAIAGFIENGWQG<br>seqid182<br>WSYNAELLVALENQHTID<br>seqid104<br>NAELLVALENQHTIDVTD | | | |
| | | | INFA H15 | seqid187<br>WSYNAELLVAMENQHTID<br>seqid188<br>NAELLVAMENQHTIDLAD | seqid4<br>GLFGAIAGFIENGWEG | | |
| | | | INFA H16 | seqid125<br>GLFGAIAGFIEGGWPG<br>seqid197<br>WSYNAKLLVLIENDRTLD<br>seqid198<br>NAKLLVLIENDRTLDLHD | | | |
| | Influenza-virus B | Influenza B virus | All strains | seqid126<br>GFFGAIAGFLEGGWEG<br>seqid199<br>ISSQIELAVLLSNEGIIN | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | seqid200 QIELAVLLSNEGIINSED | | | |
| | Influenza-virus C | Influenza C virus | | | | | |
| Paramyxo-virinae | Paramyxo-virinae | Avulavirus | Avian paramyxovirus 2 Yucaipa virus Avian paramyxovirus 3 Avian paramyxovirus 3b Avian paramyxovirus 4 Avian paramyxovirus 5 Avian paramyxovirus 6 Avian paramyxovirus 7 Avian paramyxovirus 8 Avian paramyxovirus 9 Newcastle disease virus Pigeon paramyxovirus 1 unclassified Avulavirus Avian paramyxovirus 10_Avian paramyxovirus duck/Miyagi/ 885/05 Avian paramyxovirus penguin/Falkland Islands/324/2007 Goosramyxovirus HZ Goose paramyxovirus JS/1/97/Go Goose | seqid127 GAIALGVATAAAVTAG oooo*o*oo*o*oo** | | | F0 (F2/F1) |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | paramyxovirus SF02 | | | | |
| | | Henipavirus | Hendra virus | | | | |
| | | | Hendra virus horse/Australia/ Hendra/1994 | | | | |
| | | | Nipah virus | | | | |
| | | | unclassified Henipavirus | | | | |
| | | | Bat paramyxovirus Eid.hel/GH45/ 2008 | | | | |
| | | Morbillivirus | Canine distemper virus | | | | |
| | | | Cetacean morbillivirus_ | | | | |
| | | | Dolphin morbillivirus_ | | | | |
| | | | Pilot whale morbillivirus | | | | |
| | | | Porpoise morbillivirus | | | | |
| | | | Measles virus | | | | |
| | | | Peste-des- petits-ruminants virus | | | | |
| | | | Phocine distemper virus | | | | |
| | | | Phocine distemper virus 1 | | | | |
| | | | Phocine distemper virus-2 | | | | |
| | | | Rinderpest virus | | | | |
| | | Respirovirus | Bovine parainfluenza virus 3 | | | | |
| | | | Porcine paramyxovirus strain Frost | | | | |
| | | | Porcine paramyxovirus strain Texas | | | | |
| | | | Human | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | parainfluenza virus 1 | | | | |
| | | | Human parainfluenza virus 3 | | | | |
| | | | Simian Agent 10 | | | | |
| | | | Sendai virus | | | | |
| | | | unclassified Respirovirus | | | | |
| | | | Atlantic salmon respirovirus | | | | |
| | | | Guinea pig parainfluenza virus TS-9 | | | | |
| | | | Pacific salmon paramyxovirus | | | | |
| | | | Trask River | | | | |
| | | | 1983 Swine parainfluenza virus 3 | | | | |
| | | | Tursiops truncatus parainfluenza virus 1 | | | | |
| | | Rubulavirus | Human parainfluenza virus 2 | | | | |
| | | | Human parainfluenza virus 2 (strain Greer) | | | | |
| | | | Human parainfluenza virus 2 (strain Toshiba) | | | | |
| | | | Human parainfluenza virus 4 | | | | |
| | | | Human parainfluenza virus 4a | | | | |
| | | | Human parainfluenza virus 4b | | | | |
| | | | Mapuera virus | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/fusion protein | IU group and fusion type |
|---|---|---|---|---|---|---|---|
| | | | Mumps virus | | | | |
| | | | Parainfluenza virus 5 | | | | |
| | | | Porcine rubulavirus | | | | |
| | | | Simian virus 41 | | | | |
| | | | unclassified Rubulavirus | | | | |
| | | | Porcine parainfluenza virus | | | | |
| | | | Tuhoko virus 1 | | | | |
| | | | Tuhoko virus 2 | | | | |
| | | | Tuhoko virus 3 | | | | |
| | | unclassified Paramyxovirinae | Atlantic salmon paramyxovirus | | | | |
| | | | Beilong virus | | | | |
| | | | Canine parainfluenza virus | | | | |
| | | | Chimeric human parainfluenza virus rPIV3-2 | | | | |
| | | | Fer-de-lance virus | | | | |
| | | | J-virus | | | | |
| | | | Menangle virus | | | | |
| | | | Mossman virus | | | | |
| | | | Murayama virus | | | | |
| | | | Ovine parainfluenza virus 3 | | | | |
| | | | Pacific salmon paramyxovirus | | | | |
| | | | Paramyxovirus GonoGER85 | | | | |
| | | | Recombinant PIV3/PIV1 virus | | | | |
| | | | Reptilian paramyxovirus | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/fusion protein | IU group and fusion type |
|---|---|---|---|---|---|---|---|
| | | | Salem virus | | | | |
| | | | Salmo salar paramyxovirus | | | | |
| | | | Snake ATCC-VR-1408 paramyxovirus | | | | |
| | | | Snake ATCC-VR-1409 paramyxovirus | | | | |
| | | | Tioman virus | | | | |
| | | | Tupaia paramyxovirus | | | | |
| | Pneumovirus | Human respiratory syncytial virus | Human respiratory syncytial virus A | seqid128<br>FLGLILGLGAAVTAGVA<br>***oo**o*o*ooo*o*<br>seqid129 | | | |
| | | | Human respiratory syncytial virus (strain RSB1734) | TNEAVVSLTNGMSVL<br>**o*****o**o***<br>seqid130<br>VIRFQQLNKRLLE | | | |
| | | | Human respiratory syncytial virus (strain RSB5857) | **o***o*o****<br>seqid131<br>REFSSNAGLT<br>****o***o* | | | |
| | | | Human respiratory syncytial virus (strain RSB6190) | seqid132<br>MLTDRELTSIVGGM<br>***oo**o*oooo*<br>seqid133 | | | |
| | | | Human respiratory syncytial virus (strain RSB6256) | YVIQLPLFGVMDTDCW<br>*oo***oo**o**o**<br>seqid134<br>CLARADNGWYCHNAGSLSYFP | | | |
| | | | Human respiratory syncytial virus (strain RSB642) | **ooo*o**o*o****o*o**<br>seqid135<br>DTLKSLTVPVTSRECN<br>**oo***o*ooooo** | | | |
| | | | Human respiratory syncytial virus (strain RSB6614) | seqid136<br>YDCKISTSKTYVSTAVLTTMG<br>*o*o*o***ooo*oo*o*oo*<br>seqid137 | | | |
| | | | Human respiratory syncytial virus A strain Long | VSCYGHNSCTVIN<br>*****ooo**oo*<br>Seqid75<br>GIIRTLPDGCHYIS-NKGVDRVQVGNTVYYLSKEVGK | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | LinkOut | ***o*ooo**o*o**o*o*o*o****o**oo* oo** | | | |
| | | | Human respiratory syncytial virus A2 | seqid139 PLSFPDDKFDVAIRDVEHSINQTRTFLK-ASDQ LL **o**o*o*ooo*oo*ooo***ooo*ooo**o ** | | | |
| | | | Human respiratory syncytial virus B | seqid140 KIMTSKTDISSSVITSIGAIVSCYG o*o***ooo*oo*o*oo*oo***** | | | |
| | | | Human respiratory syncytial virus (subgroup B/ strain 18537) | | | | |
| | | | Human respiratory syncytial virus (subgroup B/ strain 8/60) | | | | |
| | | | Human Respiratory syncytial virus 9320 | | | | |
| | | | Human respiratory syncytial virus B1 | | | | |
| | | | Human respiratory syncytial virus S2 | | | | |
| | | | Human respiratory syncytial virus strain RSS-2 | | | | |
| | | | unclassified Human respiratory syncytial virus | | | | |
| | | Bovine respiratory syncytial virus | All strains | seqid128 FLGLILGLGAAVTAGVA ***oo**o*o*ooo*o* | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | Metapneum ovirus | Avian metapneumo-virus | All strains | seqid134<br>CLARADNGWYCHNAGSLSYFP<br>**ooo*o**o*o****o*o** | | | |
| | | Human metapneumo-virus | All strains | seqid133<br>YVIQLPLFGVMDTDCW<br>*oo***oo**o**o**<br>seqid141 | | | |
| Corona-viridae | Corona-virinae | Alphacorona-virus | Alphacoronavirus 1<br>Coronavirus group 1b<br>Human coronavirus 229E<br>Human coronavirus NL63<br>Miniopterus bat coronavirus 1<br>Miniopterus bat coronavirus HKU8<br>Porcine epidemic diarrhea virus<br>Rhinolophus bat coronavirus HKU2<br>Scotophilus bat coronavirus 512<br>unclassified Alphacoronavirus | RSAIEDLLFDKVKLSDVG<br>**oo****oo**ooo*o*<br>seqid142<br>VPFYLNVQYRINGLGVT<br>o**ooooo**o**o***<br>seqid143<br>VLSQNQKLIANAFNNALHAIQ<br>**oo***o*ooo*oo*ooo**<br>seqid144<br>TNSALVKIQAVVNANA<br>*oo**o*o*o***oo*<br>seqid145<br>AEAQIDRLINGRLTALNAYVSQQL<br>*oo******o***oo*oo*oo***<br>seqid146<br>SAAQAMEKVNECVKSQSSRINFCGNGNHIIS<br>o*oo*oo*oo***oo*oo*oo***o*o*oo*<br>seqid147<br>APYGLYFIHFNYVP<br>**o*oo*o*oo*o*<br>seqid148<br>LQEAIKVLNHSYINLKDIGTY-EYYVKWPWYVW<br>oo*oo*o**o*ooo*ooo*oo*o*o*****o*<br>seqid209 | | | S (S1/S2) |
| | | Betacorona-virus | Betacoronavirus 1<br>Coronavirus group 2b<br>Coronavirus group 2c<br>Human coronavirus HKU1<br>Murine coronavirus<br>Pipistrellus bat | EVFAQVKQMYKTPTLKYFGGFNFSQIL<br>seqid210<br>EVFAQVKQMYKTPAIKDFGGFNFSQIL<br>Seqid211<br>SFIEDLLFNKVTLADAGF<br>Seqid212<br>SAIEDLLFNKVRLSDVGF<br>Seqid213<br>SLLEDLLFNKVKLSDVGF<br>Seqid214<br>SAIEDLLFSKVKLADVGF | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | coronavirus HKU5 | Seqid215 SAIEDLLFDKVKLSDVGF | | | |
| | | | Rousettus bat coronavirus HKU9 | | | | |
| | | | Severe acute respiratory syndrome-related coronavirus recombinant | | | | |
| | | | SARSr-CoV | | | | |
| | | | SARS coronavirus | | | | |
| | | | Tylonycteris bat coronavirus HKU4 | | | | |
| | | | unclassified Betacoronavirus | | | | |
| | | Gammacorona-virus | Avian coronavirus | | | | |
| | | | Beluga Whale coronavirus SW1 | | | | |
| | | unclassified coronaviruses | Alpaca coronavirus CA08-1/2008 | | | | |
| | | | Bat coronavirus | | | | |
| | | | Bird droppings coronavirus | | | | |
| | | | Bovine respiratory coronavirus | | | | |
| | | | Chicken enteric coronavirus | | | | |
| | | | Coronavirus Anas | | | | |
| | | | Coronavirus oystercatcher/ p17/2006/GBR | | | | |
| | | | Coronavirus red knot/p60/2006/GBR | | | | |
| | | | Ferret enteric coronavirus 1202 | | | | |
| | | | Ferret systemic coronavirus MSU-S | | | | |
| | | | Ferret systemic coronavirus WADL | | | | |
| | | | Guangxi coronaviridae | | | | |
| | | | Human coronavirus NO | | | | |
| | | | Human enteric coronavirus strain 4408 | | | | |
| | | | Kenya bat coronavirus | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | Mink coronavirus strain WD1133<br>Parrot coronavirus AV71/99<br>Quail coronavirus Italy/Elvia/2005<br>Tai Forest coronavirus<br>unidentified coronavirus<br>unidentified human coronavirus | | | | |
| Arena-viridae | Arena-virus | LCMV-Lassa virus (Old World) complex | Ippy virus<br>Lassa virus<br>Lujo virus<br>Lymphocytic choriomeningitis virus<br>Mobala virus<br>Mopeia virus | seqid149<br>NALINDQLIMKNHLRDIMGIPYC<br>*o**o***o*o***o*o**o***<br>seqid150<br>FTWTLSDSEGKDTPGGYCLT<br>oo*ooo*oo*ooo***o**o<br>seqid151<br>KCFGNTAIAKCNQKHDEEFCDMLRLFDFN<br>***o*ooo****oo*oo****ooo*ooo*<br>seqid152<br>MLQKEYMERQGKTPLGLVDLFVFS<br>*ooo*oo**oo**oo*o*oooo*o | | | GpC (Gp1/ Gp2) |
| | | Tacaribe virus (New World) complex | Amapari virus<br>Chapare virus<br>Flexal virus<br>Guanarito virus<br>Junin virus<br>Latino virus<br>Machupo virus<br>Oliveros virus<br>Paran/ virus<br>Pichinde virus<br>Pirital virus<br>Sabi/ virus<br>Tacaribe virus<br>Tamiami virus<br>Whitewater<br>Arroyo virus | seqid150<br>FTWTLSDSEGKDTPGGYCLT<br>oo*ooo*oo*ooo***o**o<br>seqid151<br>KCFGNTAIAKCNQKHDEEFCDMLRLFDFN<br>***o*ooo****oo*oo****ooo*ooo*<br>seqid152<br>MLQKEYMERQGKTPLGLVDLFVFS<br>*ooo*oo**oo**oo*o*oooo*o | | | |
| Hepadna-viridae | Genus Orthohepadna-virus | Hepatitis B virus | HBV genotype A<br>HBV genotype B<br>HBV genotype C<br>HBV genotype D | seqid153<br>FNPLGFFPSHQLDPLF<br>o***o*o*o*o*o*o*<br>seqid154 | | | L and M and S Where S mediates |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | HBV genotype E<br>HBV genotype F<br>HBV genotype G<br>HBV genotype H<br>Hepatitis B virus alpha1<br>Hepatitis B virus LSH/chimpanzee<br>Hepatitis B virus strain cpz<br>Hepatitis B virus subtype adr<br>Hepatitis B virus subtype adw<br>Hepatitis B virus subtype adyw<br>Hepatitis B virus subtype ayw | ADWDKNPNKDPWP<br>o*o*o*oo*oooo<br>seqid155<br>MESITSGFLGPLLVLQAVFF<br>oooooooo*ooooo**oooo<br>seqid156<br>LLTRILTIPQSLDSWWTSLNFLGGA<br>oooooo*oooo*oooo***o*o*oo<br>seqid157<br>CPPTCPGYRWMC<br>oo*o*****o*o<br>seqid158<br>LFILLLCLIFLLVLLDYQ<br>*oo*ooo*oo*oo*oooo | | | fusion |
| Rhabdo-viridae | Dimarhabdo-virus | Ephemerovirus | Bovine ephemeral fever virus | seqid160<br>LDGYLCRKQKWEVTCTETWYFVTD<br>*o*oo****o*ooo*o*****o*o<br>seqid161<br>KYQIIEVIPTENEC<br>o***o**o*oooo*<br>seqid162<br>LKGEYIPPYYPPTNCVWNAIDTQE<br>oo*oo*******oo*o**oooo**<br>seqid163<br>IEDPVTMTLMDSKFTKPC<br>ooo*oooooo**o*oo**<br>seqid164<br>LHCQIKSWECIPV<br>o**oo*o****o*<br>seqid165<br>SHRNMMEALYLESPD<br>*oo*oo*o*oo*o**<br>seqid166<br>LTFCGYNGILLDNGEWWSIY<br>o****oo**oooo******<br>seqid167<br>ELEHEKCLGTLEKLQNGE<br>*****o**o*oo*oo*o*<br>seqid168<br>LDLSYLSPSNPGKHYAY<br>**o***o*oo**oo***<br>seqid169 | | | Glyco-protein G |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/fusion protein | IU group and fusion type |
|---|---|---|---|---|---|---|---|
| | | | | IRAVCYYHTFSMNLD<br>o**o*o*oo*oooo* | | | |
| | | Vesiculovirus | Carajas virus<br>Chandipura virus<br>Cocal virus<br>Isfahan virus<br>Maraba virus<br>Piry virus<br>recombinant<br>Vesiculovirus<br>Spring viraemia<br>of carp virus<br>Vesicular<br>stomatitis<br>Alagoas virus<br>Vesicular<br>stomatitis<br>Indiana virus<br>Vesicular<br>stomatitis<br>New Jersey virus | seqid170<br>EWKTTCDYRWYGPQYITHSI<br>o*o****o*****o*o*o*<br>seqid171<br>LGFPPQSCGWASVTT<br>o****oo**oooooo<br>seqid1<br>VQVTPHHVLVDEYTGEWVDSQFINGKC<br>ooooo*o*oooo*o*o*o*oooooooo | | | |
| | Lyssavirus | Aravan virus<br>Australian bat<br>lyssavirus<br>Duvenhage virus<br>European bat<br>lyssavirus 1<br>European bat<br>lyssavirus 2<br>Irkut virus<br>Khujand virus<br>Lagos bat virus<br>Mokola virus<br>West Caucasian<br>bat virus | | | | | |
| | | Rabies virus | Rabies virus AB21<br>Rabies virus AB22<br>Rabies virus AVO1<br>Rabies virus BNG4<br>Rabies virus BNG5<br>Rabies virus<br>China/DRV | seqid5<br>GFTCTGVVTEAETYTNFVGYVT<br>*o****o**o*oo*oooo***<br>seqid6<br>SLHNPYPDYRWLRTVKTT<br>*ooooooooooo***o*<br>Seqid138 | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | Rabies virus China/MRV | ESLVIISPSVADLDPYDRSLHS *ooo***oooo*o**ooo | | | |
| | | | Rabies virus CVS-11 | Seqid91 CKLKLCGVLGLRLMDGT | | | |
| | | | Rabies virus ERA | *ooo****oooo*ooo* Seqid206 | | | |
| | | | Rabies virus Eth2003 | ILGPDGNVLIPEMQSS o**o*ooo*******o | | | |
| | | | Rabies virus HEP-FLURY | seqid82 QHMELLESSVIPLVHPL | | | |
| | | | Rabies virus India | *ooo**o*ooo**oo** | | | |
| | | | Rabies virus Nishigahara RCEH | | | | |
| | | | Rabies virus Ontario fox | | | | |
| | | | Rabies virus Ontario skunk | | | | |
| | | | Rabies virus PM | | | | |
| | | | Rabies virus red fox/08RS-1981/Udine/2008 | | | | |
| | | | Rabies virus SAD B19 | | | | |
| | | | Rabies virus silver-haired bat-associated SHBRV | | | | |
| | | | Rabies virus strain Pasteur vaccin | | | | |
| | | | Rabies virus strain Street | | | | |
| | | | Rabies virus vnukovo-32 | | | | |
| | | | Thailand genotype 1 dog lyssavirus | | | | |
| | | unclassified Lyssavirus | Bokeloh bat lyssavirus | | | | |
| | | | European bat lyssavirus | | | | |
| | | | Lyssavirus Ozernoe | | | | |
| | | | Shimoni bat virus | | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | Novirhabdo-virus | Hirame rhabdovirus<br>Infectious hematopoietic necrosis virus<br>Snakehead rhabdovirus<br>Viral hemorrhagic septicemia virus | | | | | |
| | unassigned Rhabdo-viridae | Bangoran virus<br>Bimbo virus<br>Bivens Arm virus<br>Flanders virus<br>Garba virus<br>Klamath virus<br>Malpais Spring virus<br>Nasoule virus<br>Ngaingan virus<br>Ouango virus<br>Sigma virus<br>Tupaia virus<br>Wongabel virus | | | | | |
| Filo-viridae | | | Lloviu virus (LLOV)<br>Bundibugyo virus (BDBV; previously BEBOV)<br>Reston virus (RESTV; previously REBOV)<br>Sudan virus (SUDV; previously SEBOV)<br>Tai Forest virus (TAFV; previously CIEBOV)<br>Ebola virus (EBOV; previously ZEBOV)<br>Marburg virus (MARV)<br>Ravn virus (RAVV) | Seqid216<br>GAAIGLAWIPYFGPAAE<br>oo*o*oo***o***ooo<br>seqid217<br>GAAVGLAWIPYFGPAAE<br>Seqid218<br>GAAAGLAWIPYFGPAAE<br>Seqid219<br>DLAAGLSWIPFFGPGIE<br>Seqid220<br>HNAAGIAWIPYFGPGAE | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| Lenti-virisae | | Hiv1 | | Seqid221<br>AVGLGALFLGFLGAAGSTMGAAS<br>oooo**ooo*o*oo*****o**o<br>seqid222<br>LTLTGQARQLLS<br>o***o*o*o*oo<br>seqid223<br>GIVQQQSNLLQAIEAQQ<br>o*****o***o*****o<br>seqid224<br>GLGAMFLGFLGAAGSTMGAASLTLTWARQLL<br>S<br>Seqid225<br>GIGAMFLGLLSAAGSTM-<br>SAAAITLTVQTRQLL<br>S<br>Seqid226<br>GIGAMFLGLL-<br>SAAGSTMGAAAITLTVQTRQLL<br>S<br>Seqid227<br>GIGAVFLGFLGAAGSTMGAASITLTVQAR-<br>QLL<br>S<br>Seqid228<br>GVGALFLGFLSAAGSTMGAASITLTVQAR-<br>QLL<br>S<br>Seqid229<br>GIGAMILGFLGAAGSTMGAASITLTVQAR-<br>QLL<br>S<br>Seqid230<br>GLGAMFLGFLGAAGSTMGAASITLTVQAR-<br>QLL<br>S<br>Seqid231<br>GEGAMFLGFLGAAGSTMGAASITLTVQAR-<br>QLL<br>S<br>Seqid232<br>TLGAMFLGFLGAAGSTMGAASMTLTWARQLL<br>S<br>Seqid233<br>GLGAVFLGFLGAAGSTMGAASITLTVQAR-<br>QLL<br>S<br>Seqid234 | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | TIGAMFLGFLGAAGSTMGAA-<br>SITLTVQARRLL<br>S<br>Seqid235 | | | |
| | | | | TIGAMFLGFL-<br>GAAGSTMGAASMTLTVQARLLL<br>S<br>Seqid236 | | | |
| | | | | TLGAMFLGFL-<br>GAAGSTMGAASMTLTVQARLLF<br>S<br>Seqid237 | | | |
| | | | | TLGAMFLGFL-<br>GAAGSTMGAASLTLTVQARLLL<br>S<br>Seqid238 | | | |
| | | | | GVGAMFLGFLGAAGSTMGAASLTLTVQAR-<br>QLL<br>S<br>Seqid239 | | | |
| | | | | GLGAMFLGFLGAAGSTMGAA-<br>SITLTVQARLLL<br>S<br>Seqid240 | | | |
| | | | | TLGAVFLGFL-<br>GAAGSTMGAASLTLTVQARLLL<br>S<br>Seqid241 | | | |
| | | | | GIGAVFLGFLGAAGSTMGAA-<br>SITLTVQARKLL<br>S<br>Seqid242 | | | |
| | | | | GIGALFLGFLGAAGSTMGAASVTLTVQAR-<br>QLL<br>S<br>Seqid243 | | | |
| | | | | GLGALFLGFLGAAGSTMGAASVTLTVQAR-<br>QLL<br>S<br>Seqid244 | | | |
| | | | | GIGAMFLGFLGAAGSTMGAA-<br>SITLTVQARLLL<br>S<br>Seqid245 | | | |
| | | | | GIGAMFLGFL-<br>GAAGSTMGAASVTLTVQARLLL<br>S<br>Seqid246 | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | AIGALFLGFL-GAAGSTMGAASVTLTVQARLLLS Seqid247 | | | |
| | | | | TLGAMFLGFLGAAGSTMGAASLTLTVQAR-QLLS Seqid248 | | | |
| | | | | GIGALFLGFLGAAGSTMGAASMTLTVQAR-QLLS Seqid249 | | | |
| | | | | GIGAMFLGFLGAAGSTMGAASLTLTVQAR-QLLS Seqid250 | | | |
| | | | | GIGAVFLGFL-GAAGSTMGAASMTLTVQARLLLS Seqid251 | | | |
| | | | | GIGALFLGFLGAAGSTMGAASLTLTVQAR-QLLS Seqid252 | | | |
| | | | | GIGAVFLGILGAAGSTMGAASITLTVQAR-QLLS Seqid253 | | | |
| | | | | GIGAVFLGFLGAAGSTMGAASVTLTVQAR-QLLF Seqid254 | | | |
| | | | | GLGAMFFGFLGAAGSTMGAASVTLTVQAR-QLLS Seqid255 | | | |
| | | | | GIGALFLGFLGAAGSTMGAA-SITLTVQARLLLS Seqid256 | | | |
| | | | | GLGALFVGFLGAAGSTMGAASITLTVQAR-QLLS Seqid257 | | | |
| | | | | GIGALFLGFLGTAGSTMGAASVTLTVQAR-QLLS Seqid258 | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | | GIGAMIFGFLGAAGSTMGAASITLTVQAR-<br>QLL<br>S<br>Seqid259<br>GLGAVLLGFLGTAG-<br>STMGAASLTLTVQVRQLL<br>S<br>Seqid260<br>GIGAVLFGFLGAAGSTMGAA-<br>SITLTVQVRQLL<br>S<br>Seqid261<br>GLGALFLGFLGAAGSTMGAASLTLTGQAR-<br>QLL<br>S<br>oo**ooo*o*oo*****o**oo***o*o*o*o<br>o<br>Seqid262<br>GTLGAMFLGFL-<br>GAAGSTMGAASMTLTVQARQL<br>L<br>Seqid263<br>GTIGAMFLGFLGAAGSTMGAA-<br>SITLTVQARRL<br>L<br>Seqid264<br>GTIGAMFLGFL-<br>GAAGSTMGAASMTLTVQARLL<br>L<br>Seqid265<br>IGALFLGFL-<br>GAAGSTMGAASVTLTVQARLLLS<br>G | | | |
| | | | Bovine<br>lentivirus group | Seqid266<br>AVGMVIFLLVLAIMAMTASVTAA<br>***oo**********o*o*oo**<br>Seqid267 | | | |
| | | | Equine<br>lentivirus group | FGISAIVAAIVAATAIAASA<br>**o*ooo**********o*o<br>Seqid268 | | | |
| | | | Feline<br>lentivirus group | TLALVTATTAGLIGTTTGTSA<br>Seqid269<br>HVMLALATVLSMAGAGTGATA<br>Seqid270 | | | |
| | | | Ovine/caprine<br>lentivirus group | GIGLVIMLVTMAIVAAAGAS<br>*o***oo*oo***o*o***o | | | |
| | | | Human | Seqid271 | | | |

TABLE 1-continued

| Family | Genus | Species (group) | Species (Strain) | Putative ISU as identified using the criteria described in this application for identification of immuno-suppressive domains | Peptides from domains from fusion proteins exhibiting immunosuppressive activity (ISU) | Name of envelope attachment/ fusion protein | IU group and fusion type |
|---|---|---|---|---|---|---|---|
| | | | immunodefi-<br>ciency virus 2 | GVMVLGFLGFLAMAGSAMGA | | | |
| | | | Simian immunodefi-<br>ciency<br>virus | ooo***o**oooo*oooooo<br>Seqid272<br>GVFVLGFLGFLATAGSAMGA | | | |
| | | | Simian immunodefi-<br>ciency<br>virus others | oooo**oo*o*oo**ooooo<br>Seqid273 | | | |
| | | | Ovine lentivirus | GAIVLGLLGFLGLAGSAMG<br>*ooooooo*o*ooo**ooo<br>Seqid274<br>GIGLVIVLAIMAIIAAAGAGLGVANAVQ | | | |
| | Arteri-<br>viridae | Porcint<br>Reproductions<br>og<br>Respirations<br>Syndrome<br>(PRRS) | PRRS Type I | seqid275<br>SRKLGRSLIPHSCFWWLFLLC<br>seqid276<br>GNGNSSTYQYIYNLTIC<br>seqid277<br>GTAWLSTHFSWAVETFVLYHILSL<br>seqid278<br>GFLTTSHFFDTLGLGAVSITGFC<br>seqid279<br>RYAHTRFTNFIVDDRGRIHRW | | | |
| | | | PRRS Type II | seqid280<br>SNNNSSHIQLIYNLTLC<br>seqid281<br>GTDWLAQKFDWAVETFVIFPVLTH<br>seqid282<br>GALTTSHFLDTVGLATVSTAGYY<br>seqid283<br>IYAVCALAALICFVIRLAKNC<br>seqid284<br>VSTAGYYHGRYVLSSIYAVCALA<br>ALICFVIRL | | | |

All cited references are incorporated by reference.

The accompanying Figures and Examples are provided to explain rather than limit the present invention. It will be clear to the person skilled in the art that aspects, embodiments and claims of the present invention may be combined.

FIGURES

INF ISD peptide is identical to INF-F#2 and are dimeric form of the peptide with the sequence [Seq id 287] GLFGAIAGFIENGWEGCGGEKEKEK FIG. 1 shows the effect of the INF ISD peptide on TNF-alpha mRNA levels.

BMDCs were treated with LPS for 16 hours. Cell supernatants were then collected and analyzed for type I IFN using bioassay. Before LPS treatment cells were either pretreated with INF F#2, with the deletion mutant D16 or not pretreated with any peptide.

Figure 10:
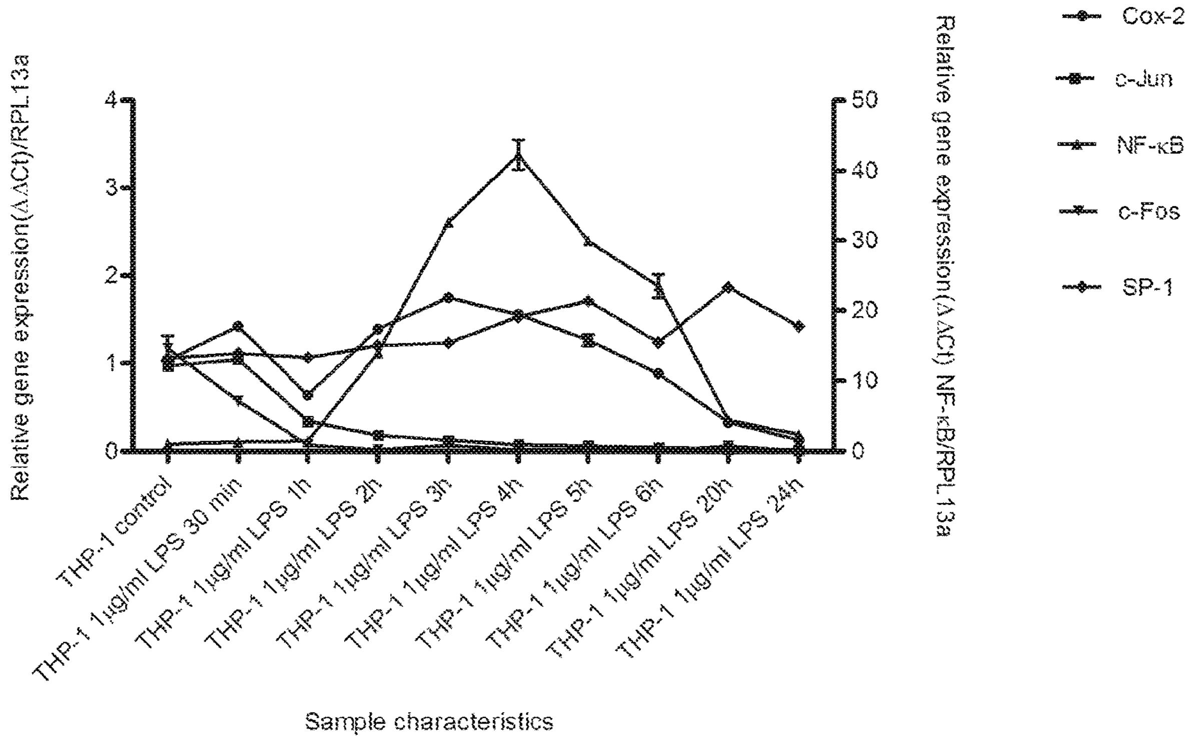

FIG. 10 shows inflammation-related enzyme and transcription factor gene expression kinetics of THP-1 monocytes stimulated with 1 μg/ml LPS. Gene expression was expressed as relative gene expression towards RPL13a-expression and non-stimulated cells at time zero (AACt). Data shown are means+standard deviation from two independent biological replications.

Figure 11:
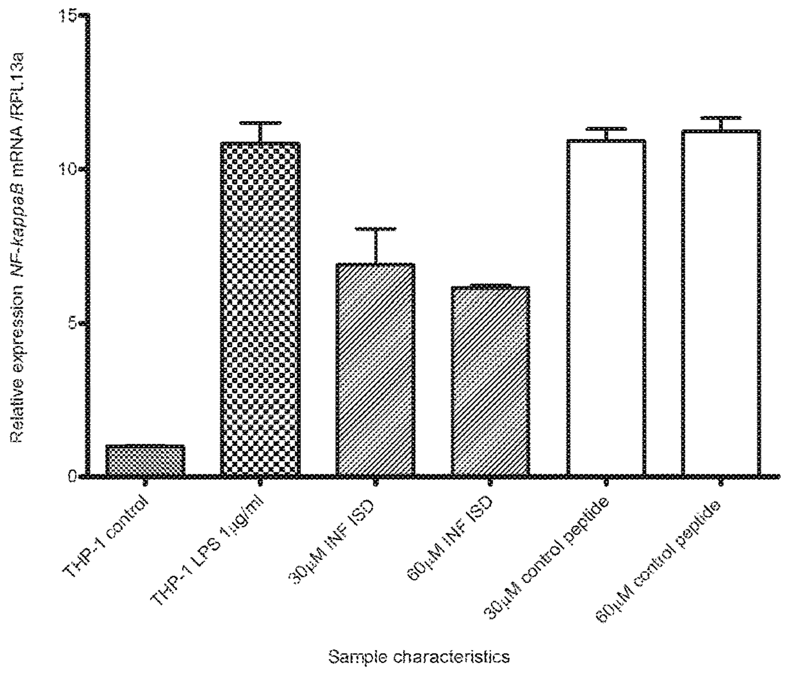

FIG. 11 shows effects of INF ISD peptide on expression of NF-kappaB mRNA in LPS-stimulated THP-1 cells. THP-1 cells were incubated with either medium alone, 30 μM, 60 μM INF ISD peptide or 30 μM, 60 μM control peptide, and stimulated with 1 μg/ml LPS. Data shown are the medians±standard deviation from two independent biological replications.

Figure 12:
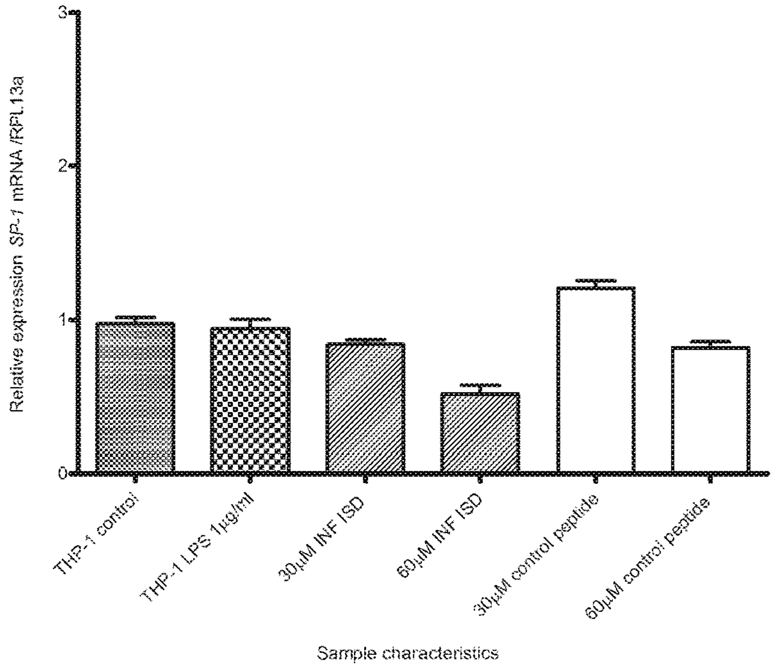

FIG. 12 shows effects of INF ISD peptide on expression of SP-1 mRNA in LPS-stimulated THP-1 cells. THP-1 cells were incubated with either medium alone, 30 μM, 60 μM INF ISD peptide or 30 μM, 60 μM control peptide, and stimulated with 1 μg/ml LPS. Data shown are the medians±standard deviation from two independent biological replications.

Figure 13:
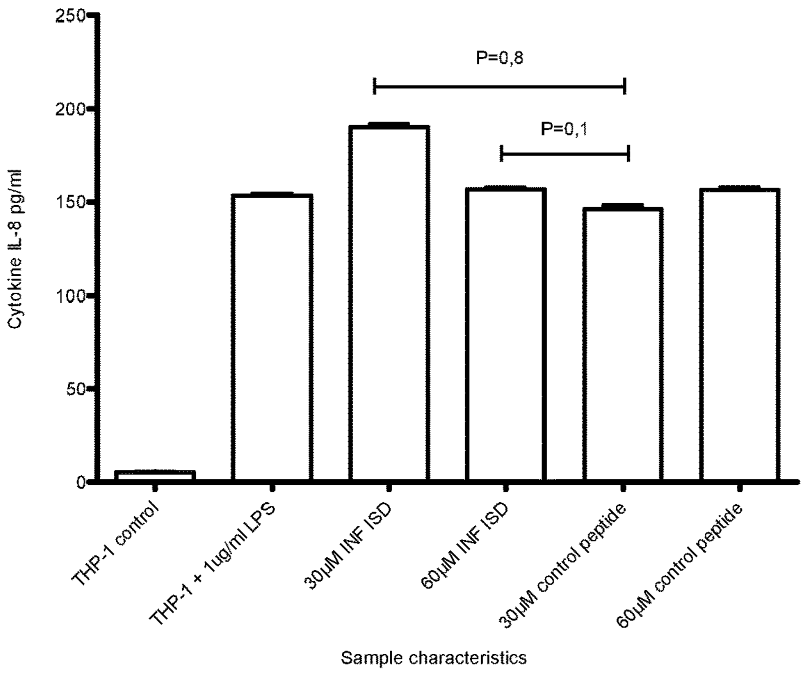

FIG. 13 shows effects of INF ISD peptide on protein secretion of IL-8 in LPS-stimulated THP-1 cells. THP-1 cells were incubated with either medium alone, 30 μM or 60 μM INF ISD peptide or 30 μM, 60 μM control peptide, and stimulated with 1 μg/ml LPS. Data shown are the median±standard deviation from three independent experiments performed in duplicates.

Figure 14:
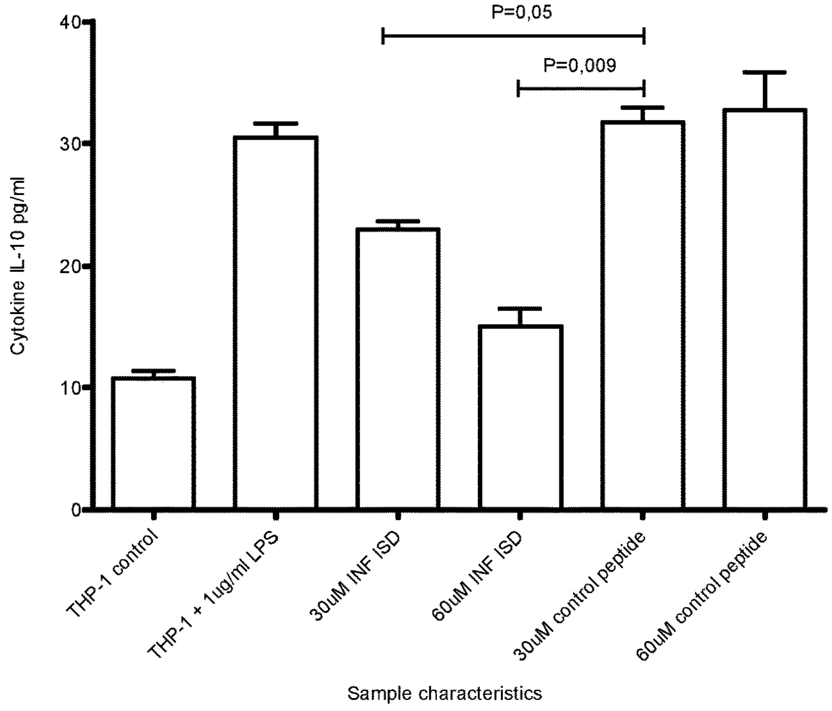

FIG. 14 shows effects of INF ISD peptide on protein secretion of IL-10 in LPS-stimulated THP-1 cells. THP-1 cells were incubated with either medium alone, 30 μM or 60 μM INF ISD peptide or 30 μM, 60 μM control peptide, and stimulated with 1 μg/ml LPS. Data shown are the median±standard deviation from three independent experiments performed in duplicates.

Figure 15:
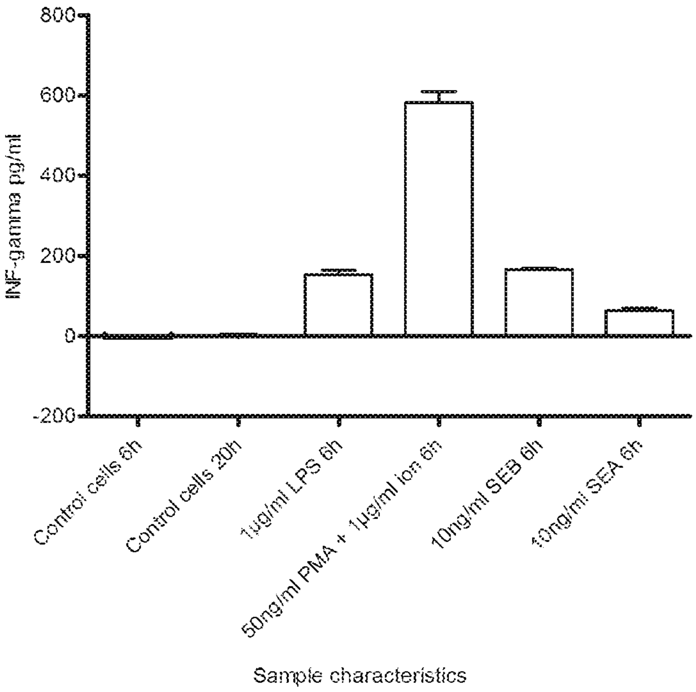

FIG. 15 shows effect of different stimulus on the secretion of IFN-gamma in PBMCs. PBMCs were incubated either with 1 μg/ml or 50 ng/ml PMA and 1 μg/ml ionomycin or 10 ng/ml SEB for indicated time periods. Data shown are the medians±standard deviation from three independent technical replicates.

Figure 16:
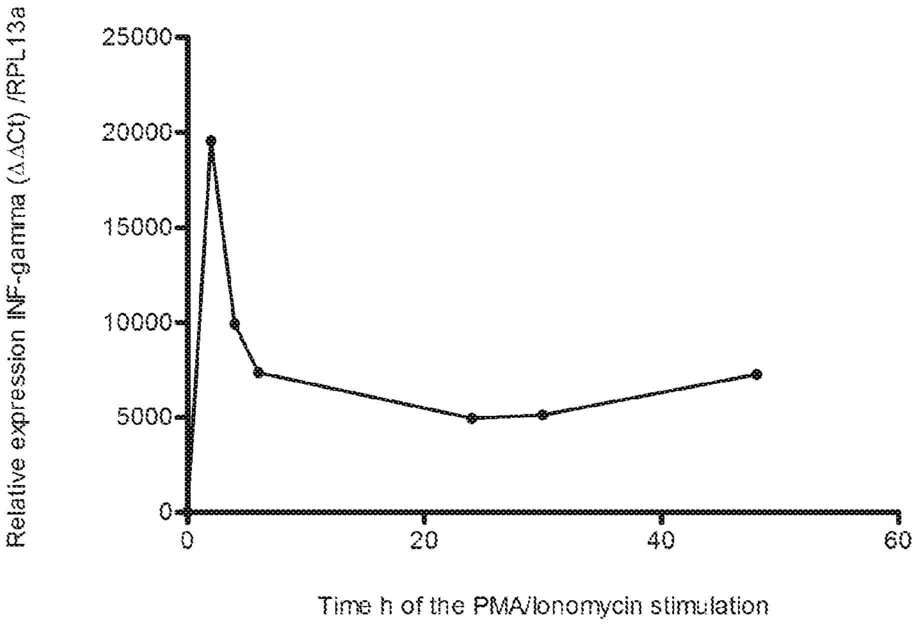

FIG. 16 shows expression kinetics of IFN gamma expression in response to PMA/ionomycin treatment. Gene expression was expressed as relative gene expression towards RPL13a expression and non-stimulated cells at time zero (ΔΔ Ct). Data shown are the medians±standard deviation from three independent technical replicates.

Figure 17:
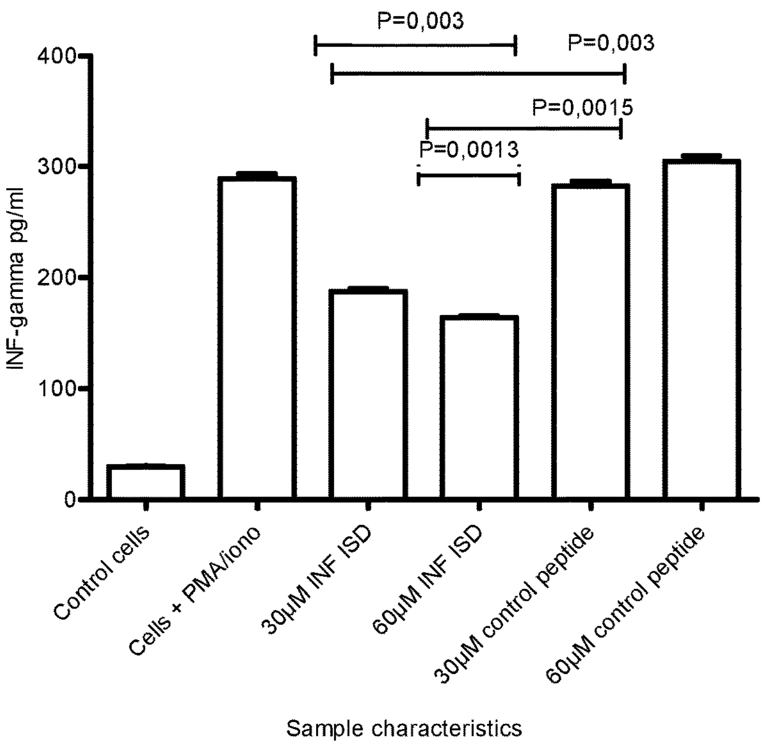

FIG. 17 shows effect of INF ISD on secretion of protein of IFN-gamma in PMA/ionomycin stimulated PBMCs. PBMCs were incubated with either medium alone, 30 μM or 60 μM Flu ISU or 30 μM or 60 μM control peptide, and stimulated with 50 ng/ml PMA and 1 μg/ml ionomycin. Data shown are the medians±standard deviation from three independent experiments performed in duplicates.

Figure 18:
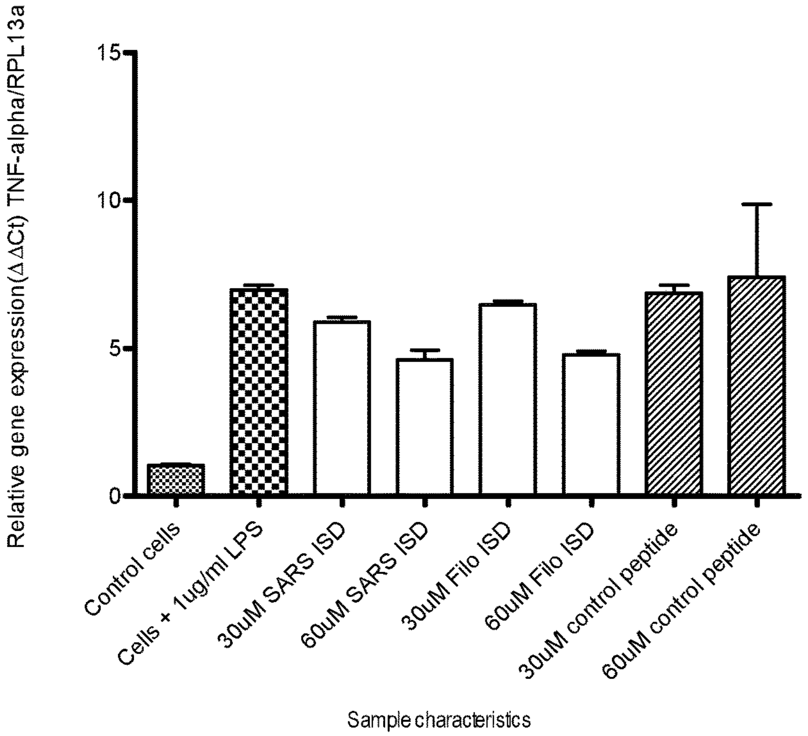

FIG. 18 shows effects of SARS ([Seq id 285] AEVQIDRLITGRLQSLQTYVCGGEKEKEK) or Filo ISD ([Seq id 286] GAAIGLAWIPYFGPAAECGGEKEKEK) on expression of TNF-alpha mRNA in LPS-stimulated THP-1 cells. THP-1 cells were incubated with either medium alone, 30 μM, 60 μM SARS or Filo ISD peptide or 30 μM, 60 μM control peptide, and stimulated with 1 μg/ml LPS. Data shown are the medians±standard deviation from two independent biological replications.

Figure 19:
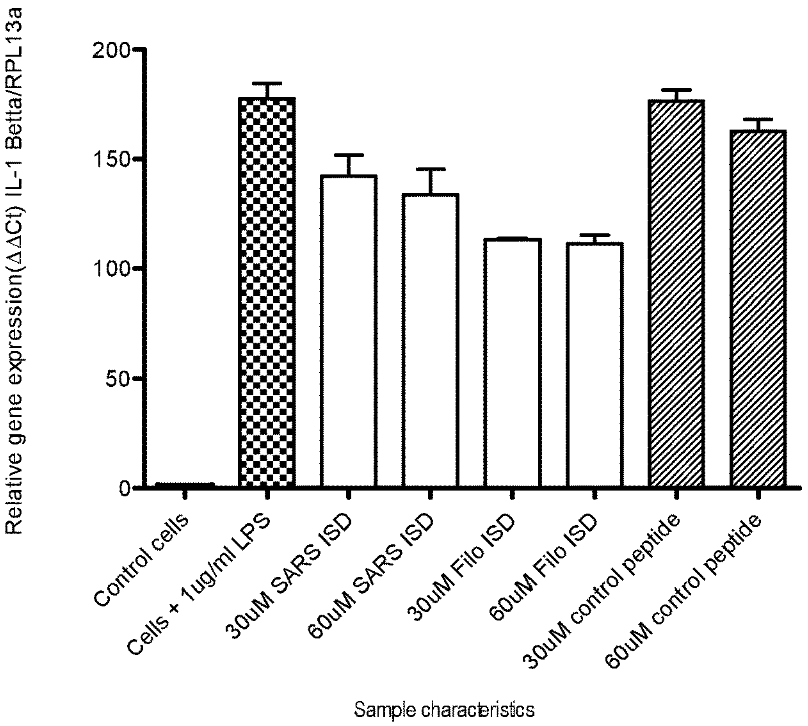

FIG. 19 shows effects of SARS or Filo ISD on expression of IL-113 mRNA in LPS-stimulated THP-1 cells. THP-1 cells were incubated with either medium alone, 30 μM, 60 μM SARS or Filo ISD peptide or 30 μM, 60 μM control peptide, and stimulated with 1 μg/ml LPS. Data shown are the medians±standard deviation from two independent biological replications.

Figure 20:
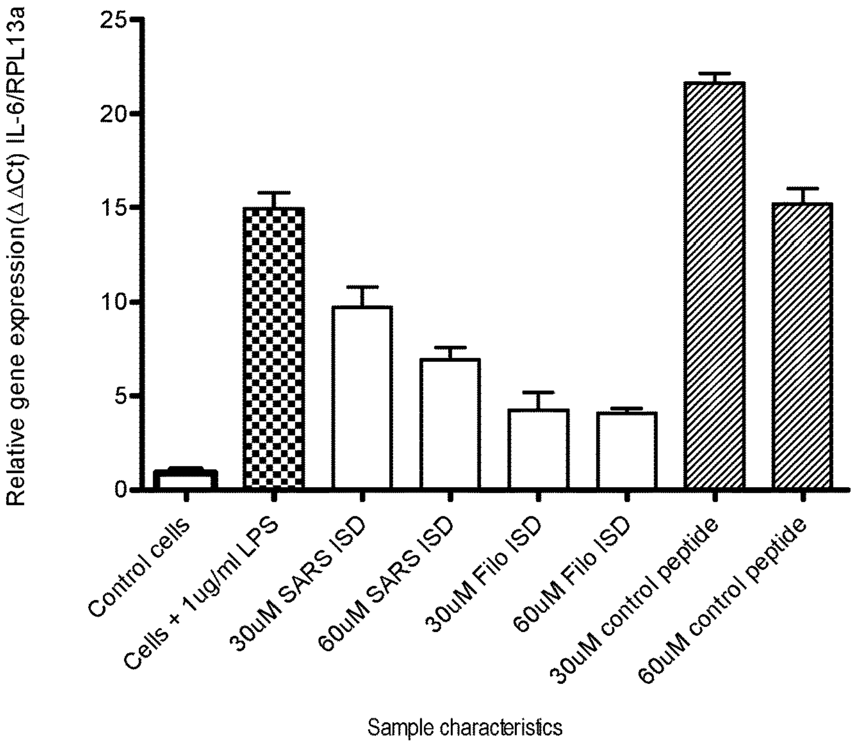

FIG. 20 shows effects of SARS or Filo ISD on expression of IL-113 mRNA in LPS-stimulated THP-1 cells. THP-1 cells were incubated with either medium alone, 30 μM, 60 μM SARS or Filo ISD peptide or 30 μM, 60 μM control peptide, and stimulated with 1 μg/ml LPS. Data shown are the medians±standard deviation from two independent biological replications.

Figure 21:
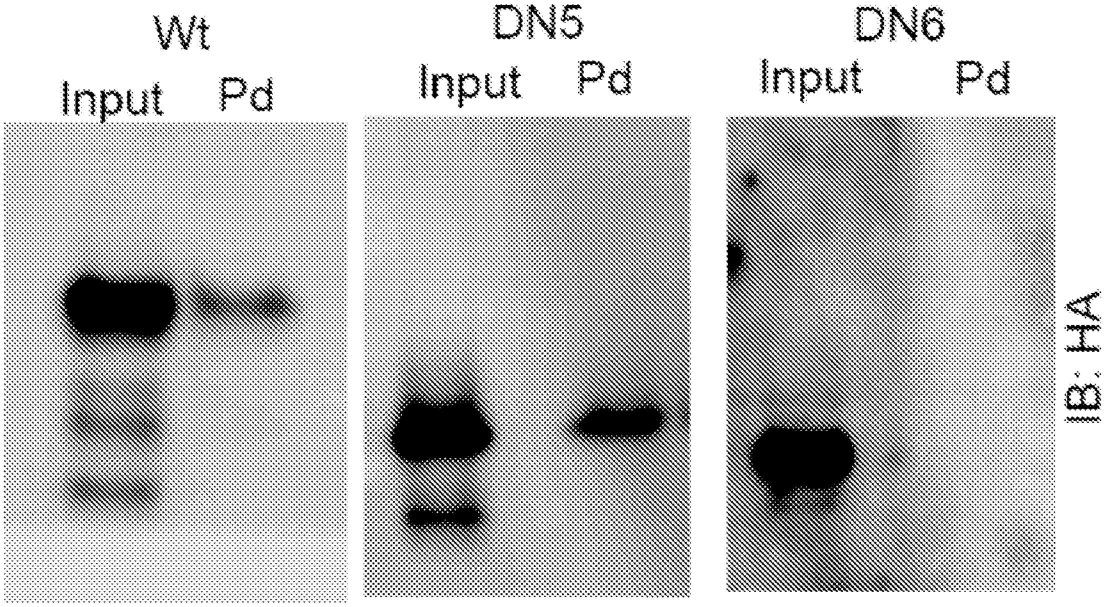

FIG. 21 shows interactions between INF ISD peptide (pFlu) and STING depends on distinct STING domains. To investigate further the interaction between STING and INF ISD peptide (pFlu) the C-terminal domain of STING was expressed with a HA-tag in HEK293 cells. STING was either in a wt form or with deletions. Lysates from tansfected cells were used for pulldown using biotinylated INF ISD peptide (pFlu) and streptavidin coated beads. The bead eluate was then immunoblotted using antibodies against HA-tag. As seen in the figure wt STING and the deletion mutant DN5 (162-N) was readily pulled down using INF ISD peptide (pFLu) whereas the deletion mutants DN6 (172-N) was not. These data indicate that amino acids 162-172 are necessary for interactions between pFlu and STING.

EXAMPLES

Example 1: ELISA

TNF-α ELISA Assay

The supernatant from THP-1 cells treated with peptides was assayed on human TNF-α ELISA Max™ Deluxe Set (Biolegend, #430205). ELISA assay was performed according to the manufacturer's protocol, as follows. Each incubation step was followed by sealing and shaking on the rotating table at 150-200 rpm, except the overnight incubation with the Capture Antibody, where plates were not shaken. One day prior running ELISA the 96-well assay plates were covered with the Capture Antibody, diluted 1:200 in 1× Coating Buffer (5× Coating Buffer diluted in $ddH_2O$). 100 μL of this Capture Antibody solution was added into all wells, sealed and incubated overnight (16-18 hrs) at 4° C. The next day all reagents from the set were brought to the room temperature (RT) before use. The plate was washed 4 times with minimum 300 μL Wash Buffer (1×PBS, 0.05% Tween 20) per well. The residual buffer in the following washing was removed by blotting the plates against the absorbent paper. Next 200 μL of the 1× Assay Diluent A (5× Assay Diluent A diluted in PBS pH=7.4) was added for 1 h to block non-specific binding. While the plate was being blocked, all samples and standards (mandatory for each plate) were prepared. Standards and samples were run in triplicates. 1 mL of the top standard 250 pg/mL was prepared in 1× Assay Diluent A (1× AD) from the TNF-α stock solution (55 ng/mL). The six two-fold serial dilutions of the 250 pg/mL top standard were performed, with the human TNF-α standard concentration: 250 pg/mL, 125 pg/mL, 62.5 pg/mL, 31.2 pg/mL, 15.6 pg/mL, 7.8 pg/mL and 3.9 pg/mL, respectively. 1× AD serves as the zero standard (0 pg/mL). After blocking the plate, washing was performed and 100 μL standards and samples were assayed in triplicates and incubated for 2 h in RT. Samples were not diluted, the whole supernatant from the THP-1 cells was assayed. After washing, 100 μl of the Detection Antibody was applied to each well, diluted 1:200 in 1× AD, and incubated for 1 hour. Plate was washed and followed by 30 minutes incubation with 100 μL of Avidin-HRP solution per well, diluted 1:1000 in 1× AD. The final washing was performed 5 times with at least 30 seconds interval between the washings, to decrease the background. Next 100 μL of the freshly mixed TMB Substrate Solution (10 mL per plate, 5 mL of each from 2 substrates provided in the set) was applied and left in the dark for 15 min. It needs to be observed to prevent signal saturation, positive wells turned blue. After incubation in the dark the reaction was stopped with 100 μL of 2N $H_2SO_4$ per well. Positive wells turned yellow. Absorbance was read at 450 nm and 570 nm (background) within 30 minutes. The data were analyzed in the Microsoft Excel 2010 program.

Example 2: Effect of Peptides on Cytokine and Transcription Factor mRNA Level Measurements by QPCT Cell Culture THP-1 cells were cultured in RPMI medium supplemented with 10% fetal bovine serum 2 mM glutamine, 100 U/ml penicillin, 100 μg/ml streptomycin and used before passage 10. Cells were cultured in a humidified atmosphere in 95% air, 5% $CO_2$ at 37° C.

RNA Isolation

RNAs from THP-1 cells were isolated using RNeasy® Plus Mini Kit (Qiagen, DK) according to the manufacturer's protocol. Quality and integrity of isolated RNA samples was controlled by determining $A_{260}/A_{280}$, $A_{260}/A_{230}$ absorbance ratios and 28S/18S rRNA ratios followed by rigorous DNase I (Ambion® TURBO DNA-Free™) treatments.

Quantitative Real-Time RT-PCR 500 ng total RNA was used for cDNA synthesis using iScript™ cDNA synthesis kit (Bio-Rad, CA USA) according to the instructions of the manufacturers. Real-time Q-PCR analysis was performed using a LightCycler 480 cycler (Roche Diagnostics, DK). 2 μl of cDNA (from a total 20 μl reaction volume) was used in a 20 μl reaction. The real-time Q-PCR reactions contained 10 μl SybrGreen 2× Master Mix (Roche Diagnostics, DK), 2 μl forward primer (5 pmol/μl), 2 μl reverse primer (5 pmol/μl) and 4 μl water. After initial denaturation at 95° C. for 10 minutes, PCR amplifications were performed for 45 cycles. The primer sequences used in this study are shown in Table 1. The crossing point (CP) for each transcript was measured and defined at constant fluorescence level in Light Cycler 480 software. The mRNA levels for the test gene were normalized to the RPL13a or RPL37A value and relative quantification was determined using the ΔCt model presented by PE Applied Biosystems (Perkins Elmer, Foster City, Calif. USA). For quantitative real-time RT-PCR analysis, standard deviations were calculated and a T-test was employed to compare expression levels. P-values 0.05 were considered statistically significant.

| Target gene/ primer name | Primer sequence 5'-3' |
|---|---|
| IL-2 β forward | GTGGCAATGAGGATGACTTGTTC |
| IL-2 β reverse | TAGTGGTGGTCGGAGATTCGTA |
| IL-6 forward | AGCCACTCACCTCTTCAGAAC |
| IL-6 reverse | GCCTCTTTGCTGCTTTCACAC |
| IL-10 forward | GTGATGCCCCAAGCTGAGA |
| IL-10 reverse | CACGGCCTTGCTCTTGTTTT |
| TNF-alpha forward | CTGCTGCACTTTGGAGTGAT |
| TNF-alpha reverse | AGATGATCTGACTGCCTGGG |
| NF-κB forward | TGAGTCCTGCTCCTTCCA |
| NF-κB reverse | GCTTCGGTGTAGCCCATT |
| RPL13a forward | CATCGTGGCTAAACAGGTACTG |
| RPL13a reverse | GCACGACCTTGAGGGCAGCA |
| RPL37A forward | ATTGAAATCAGCCAGCACGC |
| RPL37A reverse | AGGAACCACAGTGCCAGATCC |

Treatment of Cells/Induction of Cytokines

Pro- and anti-inflammatory cytokine gene expression was analyzed in un-differentiated THP-1 cells, designed as THP-1 monocytes. LPS is widely used as a potent and prototypical inducer of cytokine production in innate immunity which begins with the orchestration of monocytes. Pathogen associated molecular patterns (PAMPs), like lipopolysaccharide (LPS), play a pivotal role in initiation of variety of host responses caused by infection with Gram-negative bacteria. Such action leads to systemic inflammatory response, for instance up-regulation of pro- and anti-inflammatory cytokines, resulting in secretion of cytokine proteins into the blood stream.

THP-1 cells ($1.0\times10^6$) were cultured in a 24-well tissue culture plate (Corning). Cells were cultured with stimulant LPS at 1 μg/ml with or without indicated peptides (at the indicated concentrations) for 4 h. LPS and peptides concentrations were chosen according to our preliminary optimization studies. RPMI 1640 medium containing 10% fetal bovine serum, 2 mM glutamine, 100 U/ml penicillin, 100 μg/ml streptomycin was used as a control. To investigate gene expression and cytokine secretion cells were harvested at 4 h time point, while cell-free culture supernatants were collected and stored at −80° C. The time point of 4 h has been chosen based on the previously published gene expression and cytokine secretion kinetics of THP-1 monocytes stimulated with LPS[1]. The experiments were performed by two independent biological replications, started from a new batch of cells.

1. Wasaporn Chanput, Jurriaan Mes, Robert A. M. Vreeburg, Huub F. J. Savelkoul and Harry J. Wichers. Transcriptional profiles of LPS-stimulated THP-1 monocytes and macrophages: a tool to study inflammation modulating effects of food-derived compounds. *Food Funct.,* 2010, 1, 254-261.

Example 3

Figure 1:
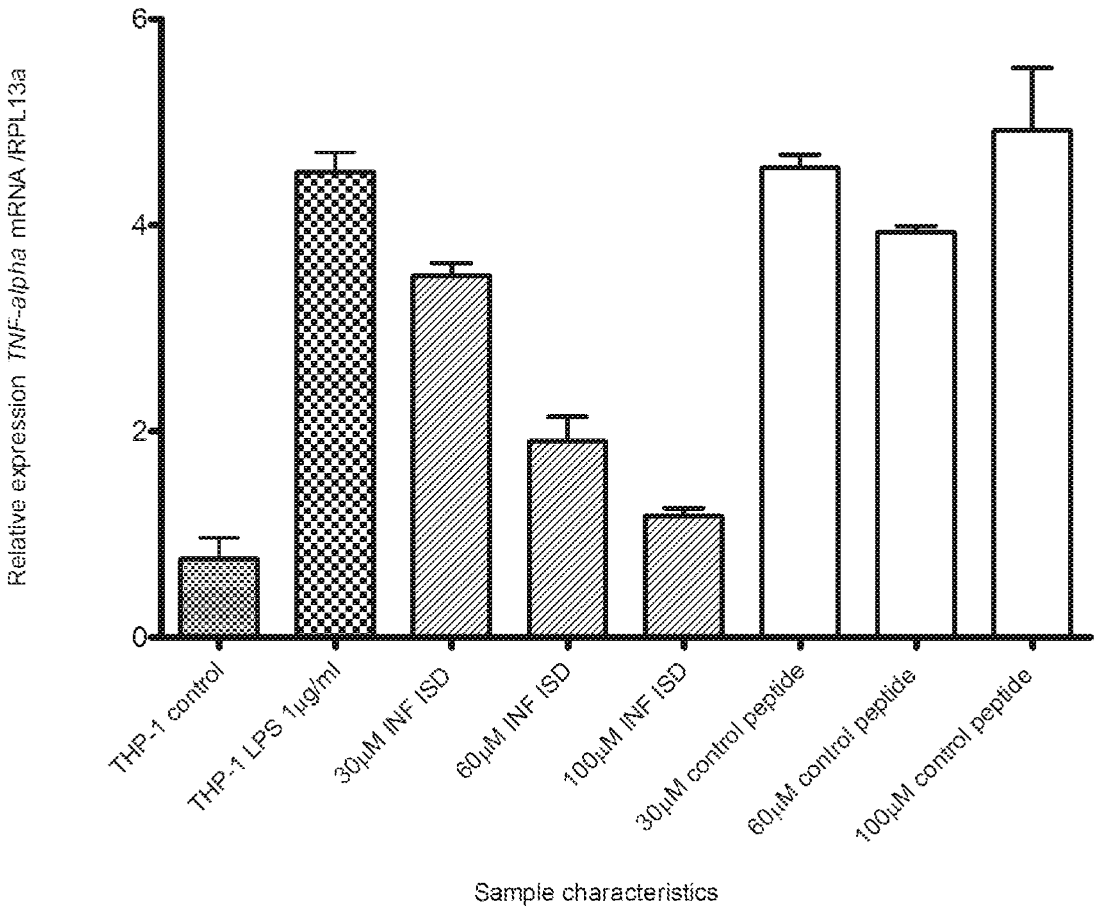
Figure 2:
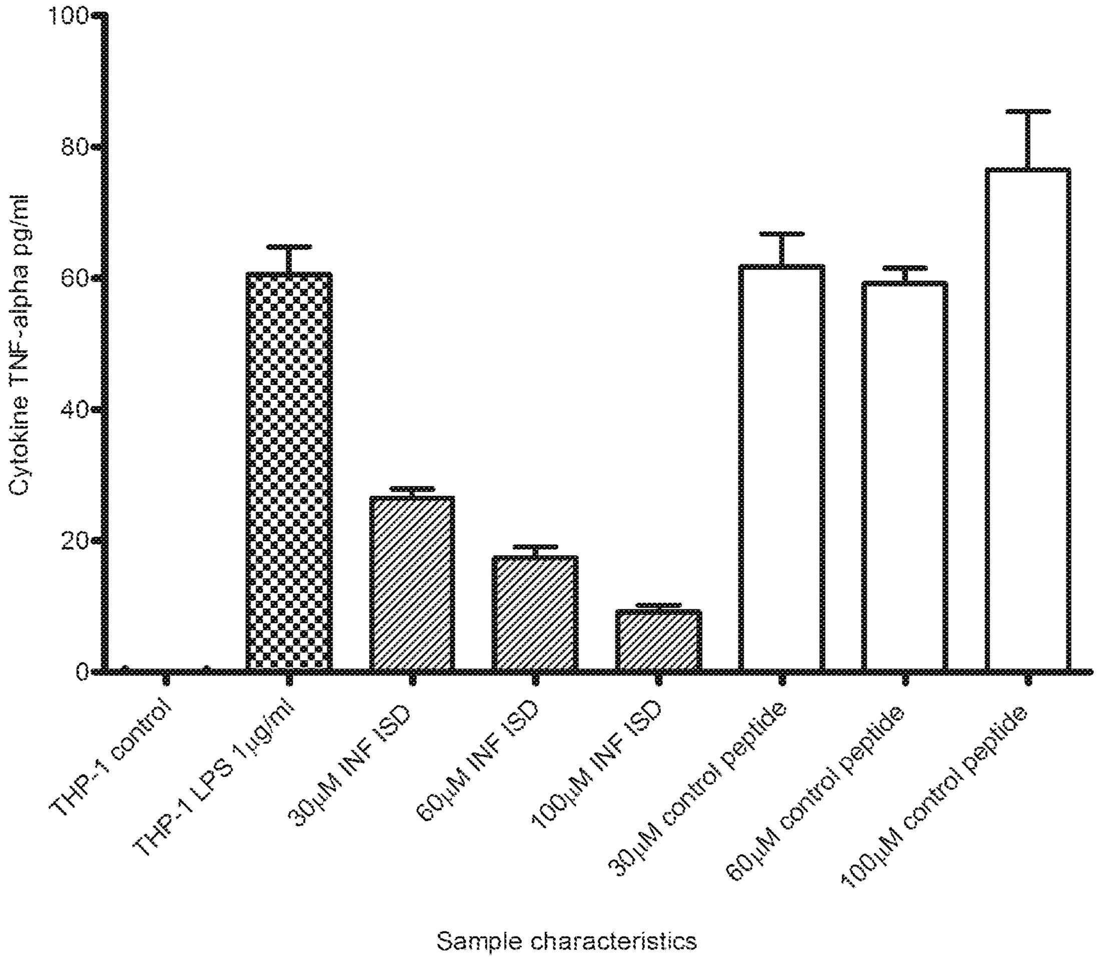
FIG. 2 shows the effect of peptide incubation on secreted TNF-alpha levels in the supernatant of THP-1 cells.
Figure 3:
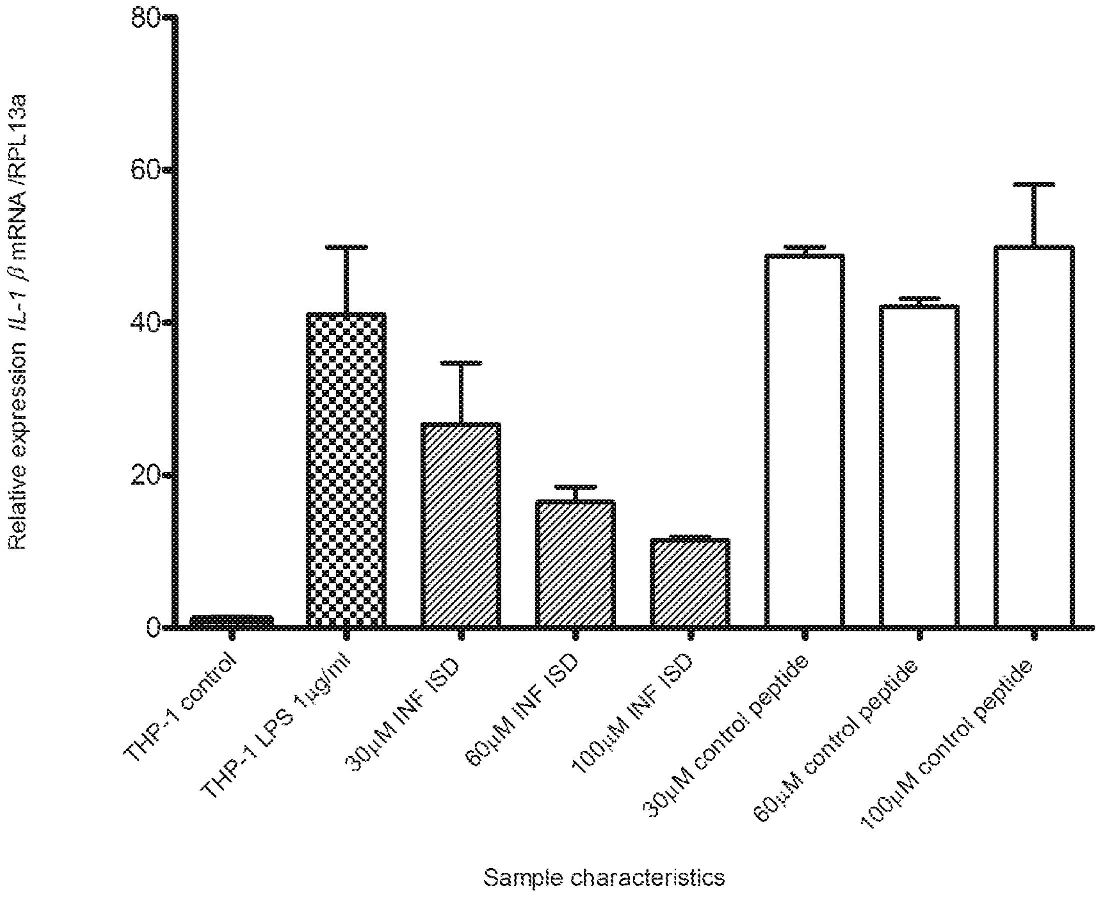
FIG. 3 shows the effect of the INF ISD peptide on IL-1 beta mRNA levels in THP-1 cells.
Figure 4:
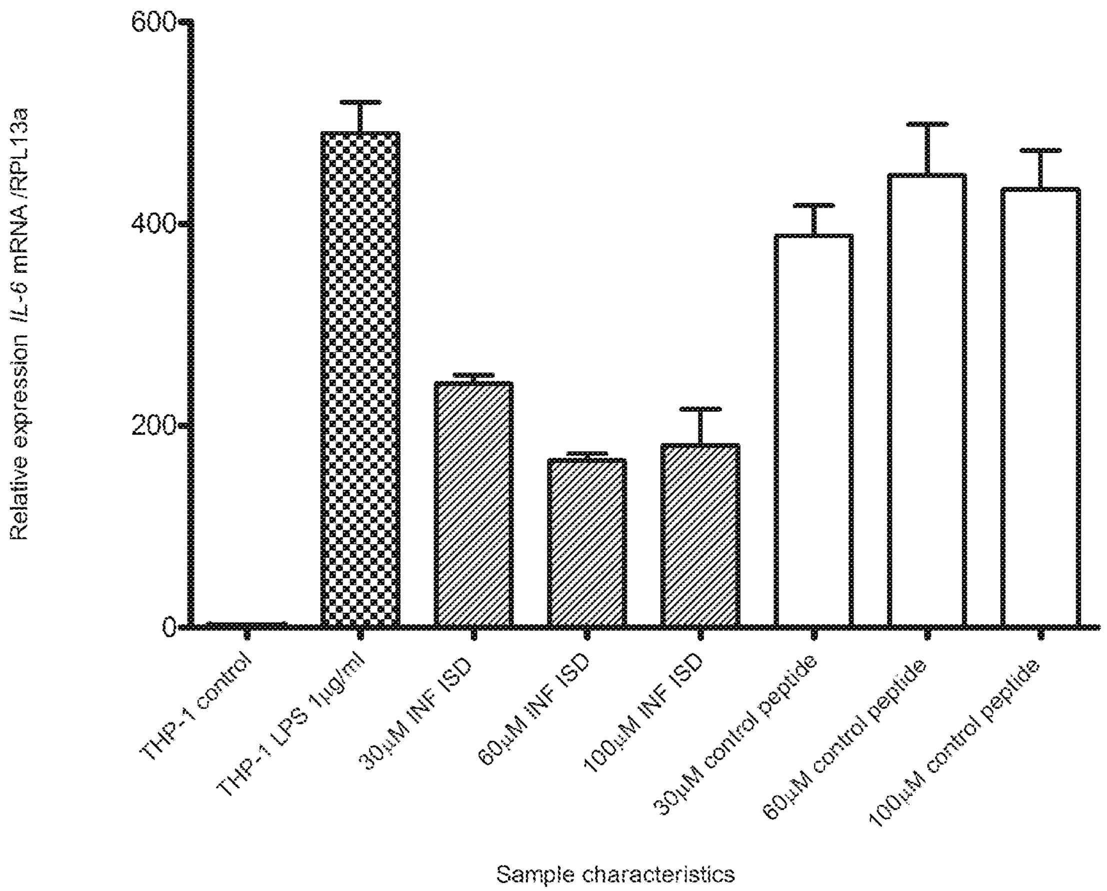
FIG. 4 shows the effect of the INF ISD peptide on IL-6 mRNA levels in THP-1 cells.
Figure 5:
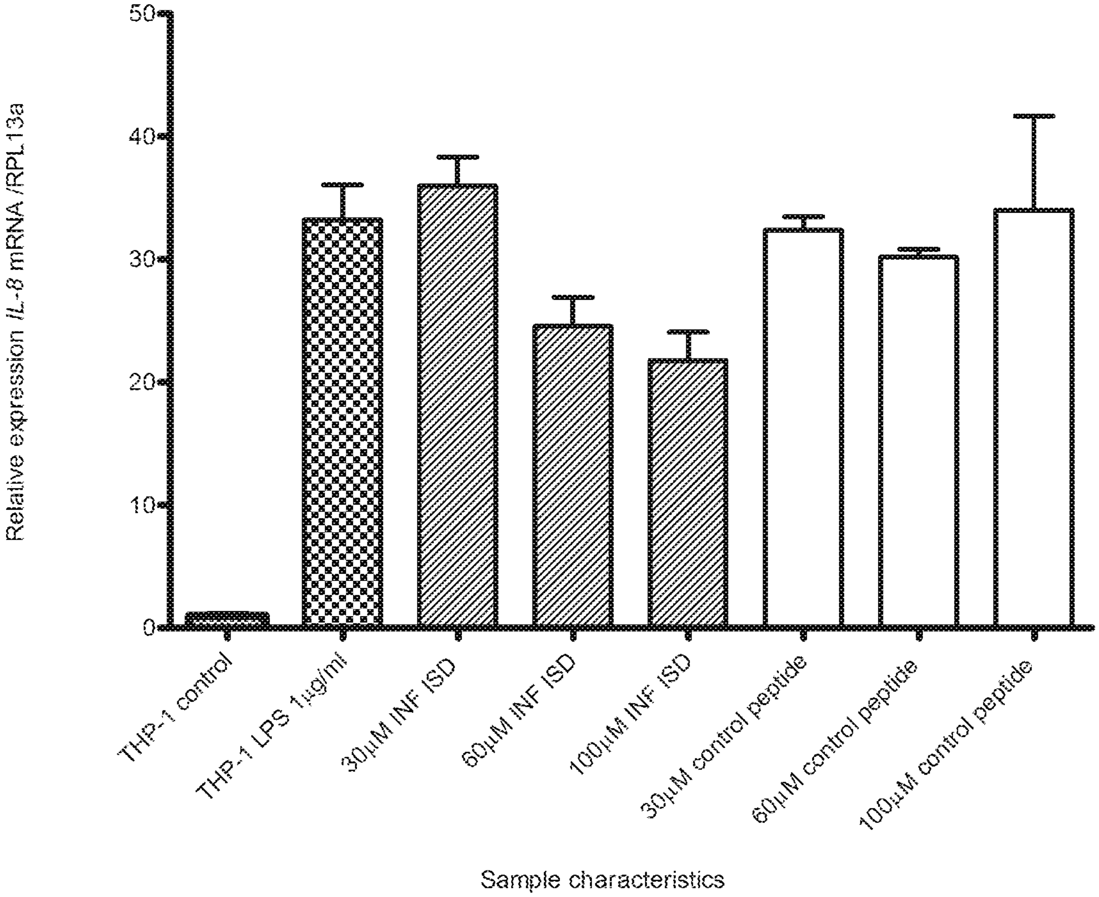
FIG. 5 shows the effect of the INF ISD peptide on IL-8 mRNA levels in THP-1 cells.
Figure 6:
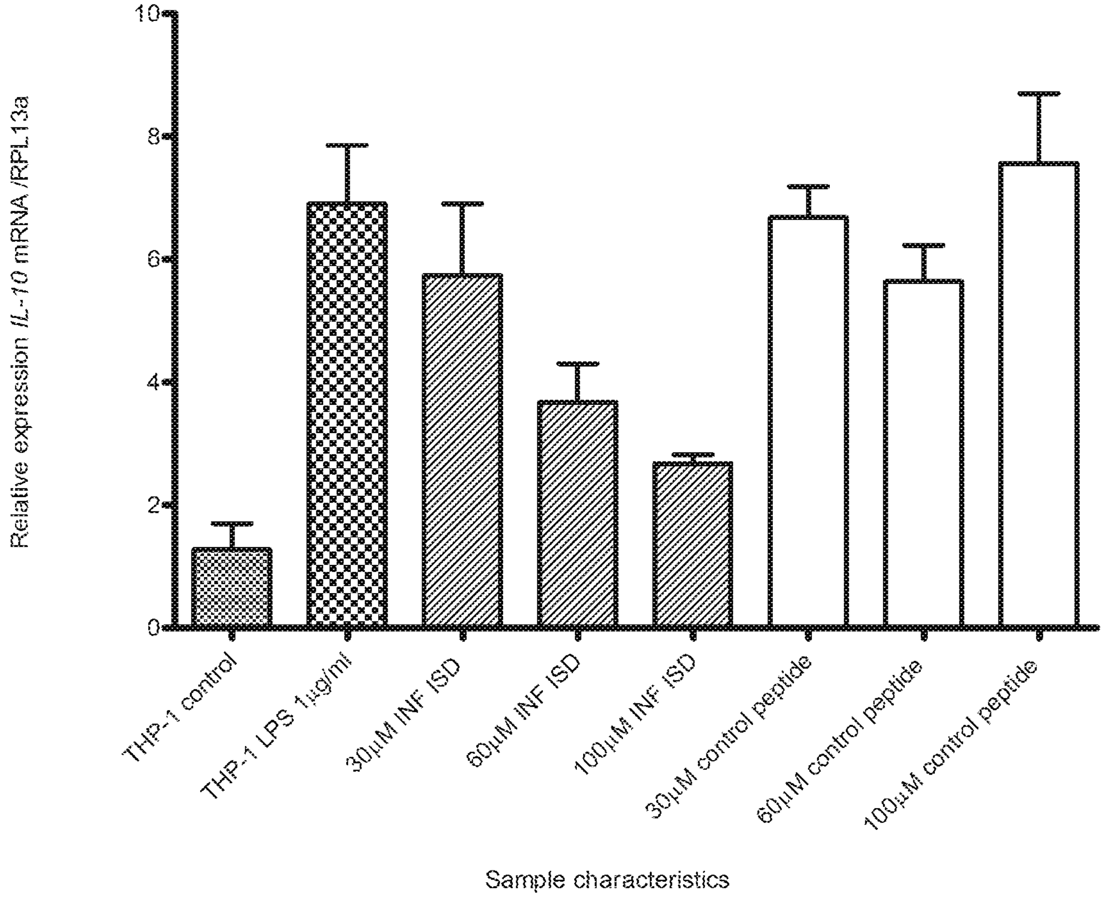
FIG. 6 shows the effect of the INF ISD peptide on IL-10 mRNA levels in THP-1 cells.
Figure 7:
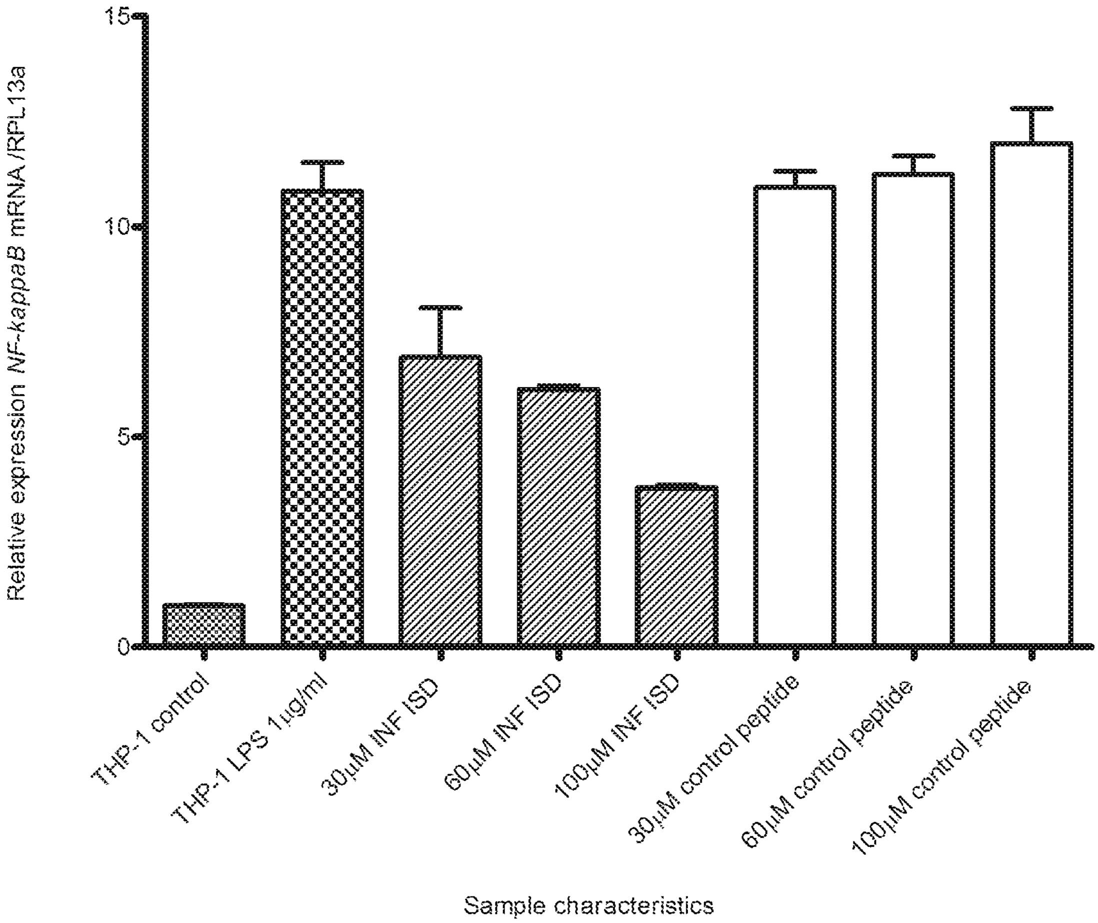
FIG. 7 shows the effect of the INF ISD peptide on NF-kappa B mRNA levels in THP-1 cells.
Figure 8:
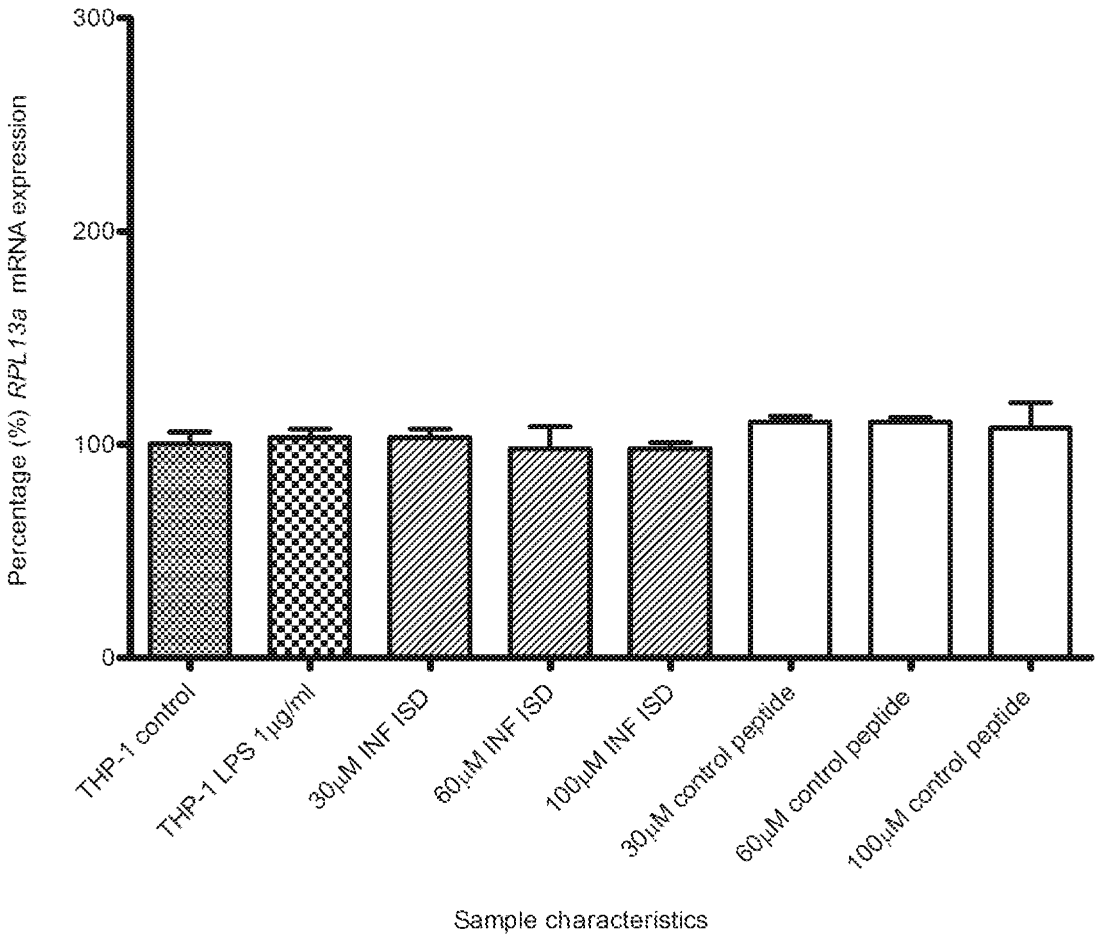
FIG. 8 shows the effect of the INF ISD peptide on the house holding gene RPL13a mRNA levels in THP-1 cells.
Figure 9:
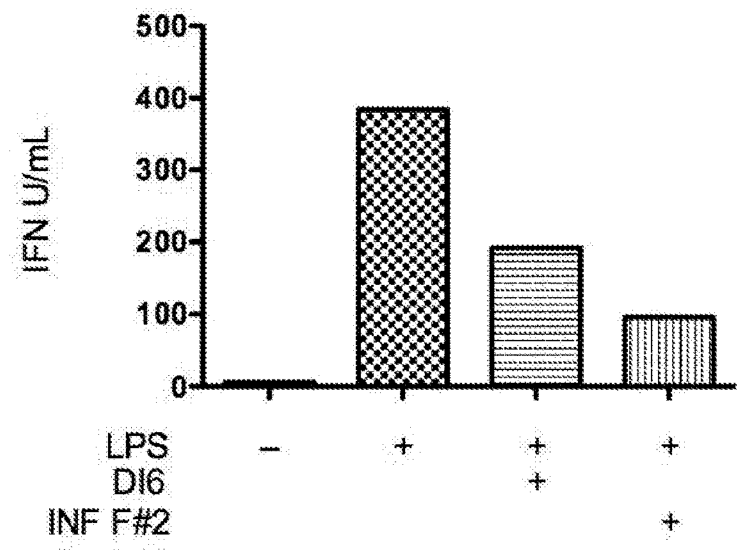
FIG. 9 shows that in the presence of INF F#2, cells treated with LPS release significantly lower amounts of cytokines.

Inflammatory shock as a consequence of LPS release remains a serious clinical concern. In humans, inflammatory responses to LPS result in the release of cytokines and other cell mediators from monocytes and macrophages, which can cause fever, shock, organ failure and death. Here we present data that show that pretreatment of cells with INF F#2 results in a decrease in the release of cytokines including pro-inflammatory cytokines such as TNFalpha and IL-6. Therefore, treatment of patients, in the risk of developing sepsis, with INF F#2 could act beneficially to decrease production of proinflammatory cytokines and hereby lessen the risk of developing shock, organ failure and death. See FIG. 8.

The content of the ASCII text file of the sequence listing named "Third-Substitute-Sequence-Listing-12397-0801-31May2022", having a size of 76.3 kb and a creation date of 31 May 2022, and electronically submitted via EFS-Web on 31 May 2022, is incorporated herein by reference in its entirety.

REFERENCES

Cianciolo 1985: Cianciolo G J, Bogerd H, Snyderman R. Human retrovirus-related synthetic peptides inhibit T lymphocyte proliferation. Immunol Lett. 1988 September; 19(1):713.

Denner 1994: Denner J, Norley S, Kurth R. The immunosuppressive peptide of HIV-1: functional domains and immune response in AIDS patients. AIDS. 1994 August; 8(8):1063 72.

Harrell 1986: Harrell R A, Cianciolo G J, Copeland T D, Oroszlan S, Snyderman R. Suppression of the respiratory burst of human monocytes by a synthetic peptide homologous to envelope proteins of human and animal retroviruses. J Immunol. 1986 May 15; 136(10):3517-20.

Kleinerman 1987: Kleinerman E S, Lachman L B, Knowles R D, Snyderman R, Cianciolo G J. A synthetic peptide homologous to the envelope proteins of retroviruses inhibits monocyte-mediated killing by inactivating interleukin 1. J Immunol. 1987 Oct. 1; 139(7):2329-37.

Mangeney 1998: Mangeney M, Heidmann T. Tumor cells expressing a retroviral envelope escape immune rejection in vivo. Proc Natl Acad Sci USA. 1998 Dec. 8; 95(25): 14920-5.

[Haraguchi 1995: Haraguchi S, Good R A, James-Yarish M, Cianciolo G J, Day N K. Induction of intracellular cAMP by a synthetic retroviral envelope peptide: a possible mechanism of immunopathogenesis in retroviral infections. Proc Natl Acad Sci USA. 1995 Jun. 6; 92(12):5568-71.

Haraguchi 1995a: Haraguchi S, Good R A, James-Yarish M, Cianciolo G J, Day N K. Differential modulation of Th1- and Th2-related cytokine mRNA expression by a synthetic peptide homologous to a conserved domain within retroviral envelope protein. Proc Natl Acad Sci USA. 1995 Apr. 11; 92(8):3611-5. Erratum in: Proc Natl Acad Sci USA 1995 Sep. 12; 92(19):9009

Haraguchi 2008: Haraguchi S, Good R A, Day-Good N K. A potent immunosuppressive retroviral peptide: cytokine patterns and signaling pathways. Immunol Res. 2008; 41(1):46-55. Review.

Mangeney 2007: Mangeney M, Renard M, Schlecht-Louf G, Bouallaga I, Heidmann O, Letzelter C, Richaud A, Ducos B, Heidmann T. Placental syncytins: Genetic disjunction between the fusogenic and immunosuppressive activity of retroviral envelope proteins. Proc Natl Acad Sci USA. 2007 Dec. 18; 104(51):20534-9.

Sander 1993: Sander H M, Morris L F, and Menter A. J Am Acad Dermatol. The annual cost of psoriasis. 1993. vol 28 (3) p 422-5

Funding et al., J Invest. Dermatol. 2008; in press: Funding A T, Johansen C, Gaestel M, Bibby B M, Lilleholt L L, Kragballe K, Iversen L. Reduced oxazolone-induced skin inflammation in MAPKAP kinase 2 knockout mice. J Invest Dermatol. 2009 April; 129(4):891-8.

Kim S D, Kim Y K, Lee H Y, Kim Y S, Jeon S G, Baek S H, Song D K, Ryu S H, Bae Y S. The agonists of formyl peptide receptors prevent development of severe sepsis after microbial infection. J Immunol. 2010 Oct. 1; 185 (7):4302-10. Epub 2010 Sep. 3. PubMed PMID: 20817875

Hillenbrand A, Knippschild U, Weiss M, Schrezenmeier H, Henne-Bruns D, Huber-Lang M, Wolf A M. Sepsis induced changes of adipokines and cytokines—septic patients compared to morbidly obese patients. BMC Surg. 2010 Sep. 9; 10:26. PubMed PMID: 20825686; PubMed Central PMCID: PMC2944119

Hamishehkar H, Beigmohammadi M T, Abdollahi M, Ahmadi A, Mahmoodpour A, Mirjalili M R, Abrishami R, Khoshayand M R, Eslami K, Kanani M, Baeeri M, Mojtahedzadeh M. Identification of enhanced cytokine generation following sepsis. Dream of magic bullet for mortality prediction and therapeutic evaluation. Daru. 2010; 18(3):155-62. PubMed PMID: 22615611; PubMed Central PMCID: PMC3304360.

Delavallée L, Duvallet E, Semerano L, Assier E, Boissier M C. Anti-cytokine vaccination in autoimmune diseases. Swiss Med Wkly. 2010 Nov. 1; 140:w13108. doi: 10.4414/smw.2010.13108. Review. PubMed PMID: 21043003.

Finkelman F D, Hogan S P, Hershey G K, Rothenberg M E, Wills-Karp M. Importance of cytokines in murine allergic airway disease and human asthma. J Immunol. 2010 Feb. 15; 184(4):1663-74. Review. PubMed PMID: 20130218.

Corren J. Cytokine inhibition in severe asthma: current knowledge and future directions. Curr Opin Pulm Med. 2011 January; 17(1):29-33. Review. PubMed PMID: 21330823.

de Paz B, Alperi-López M, Ballina-García F J, Prado C, Gutiérrez C, Suárez A. Cytokines and regulatory T cells in rheumatoid arthritis and their relationship with response to corticosteroids. J Rheumatol. 2010 December; 37(12):2502-10. Epub 010 Oct. 15. PubMed PMID: 20952465.

Malaviya A M. Cytokine network and its manipulation in rheumatoid arthritis. J Assoc Physicians India. 2006 June; 54 Suppl:15-8. Review. PubMed PMID: 16909710.

Broos S, Lundberg K, Akagi T, Kadowaki K, Akashi M, Greiff L, Borrebaeck C A, Lindstedt M. Immunomodulatory nanoparticles as adjuvants and allergen-delivery system to human dendritic cells: Implications for specific immunotherapy. Vaccine. 2010 Jul. 12; 28(31):5075-85. Epub 2010 May 15. PubMed PMID: 20478343.

Morimoto Y, Ogami A, Todoroki M, Yamamoto M, Murakami M, Hirohashi M, Oyabu T,

Myojo T, Nishi K, Kadoya C, Yamasaki S, Nagatomo H, Fujita K, Endoh S, Uchida K, Yamamoto K, Kobayashi N, Nakanishi J, Tanaka I. Expression of inflammation-related cytokines following intratracheal instillation of nickel oxide nanoparticles. Nanotoxicology. 2010 June; 4(2): 161-76. PubMed PMID: 20795893

Summer B, Paul C, Mazoochian F, Rau C, Thomsen M, Banke I, Gollwitzer H, Dietrich K A, Mayer-Wagner S, Ruzicka T, Thomas P. Nickel (Ni) allergic patients with complications to Ni containing joint replacement show preferential IL-17 type reactivity to Ni. Contact Dermatitis. 2010 July; 63(1):15-22. PubMed PMID: 20597929.

Schutte R J, Xie L, Klitzman B, Reichert W M. In vivo cytokine-associated responses to biomaterials. Biomaterials. 2009 January; 30(2):160-8. Epub 2008 Oct. 11. PubMed PMID: 18849070; PubMed Central PMCID: PMC2621303.

Rodriguez A, Meyerson H, Anderson J M. Quantitative in vivo cytokine analysis at synthetic biomaterial implant sites. J Biomed Mater Res A. 2009 April; 89(1):152-9. PubMed PMID: 18431759.

Roberts-Thomson I C, Fon J, Uylaki W, Cummins A G, Barry S. Cells, cytokines and inflammatory bowel disease: a clinical perspective. Expert Rev Gastroenterol Hepatol. 2011 December; 5(6):703-16. Review. PubMed PMID: 22017698.

Rogler G, Andus T. Cytokines in inflammatory bowel disease. World J Surg. 1998 April; 22(4):382-9. Review. PubMed PMID: 9523521.

The invention claimed is:

1. A method for relieving, alleviating, ameliorating, and/or reducing the susceptibility of an autoimmune disease, the method comprising the step of administering to a subject in need thereof a pharmaceutical composition comprising an immune suppressive domain from a virus fusion protein as an active substance, wherein said immune suppressive domain is from a virus of the Orthomyxoviridae family, and wherein said autoimmune disease is selected from the group consisting of acute disseminated encephalomyelitis (ADEM), Addison's disease, amyotrophic lateral sclerosis, ankylosing spondylodiscitis, antiphospholipid syndrome, autoimmune uveitis, celiac disease, chronic obstructive pulmonary disease, Churg-Strauss syndrome, Crohn's disease, Cushing's Syndrome, diabetes mellitus type 1, drug-induced lupus, discoid lupus erythematosus, glomerulonephritis, Goodpasture's syndrome, Graves' disease, Guillain-Barré syndrome (GBS), Hashimoto's encephalopathy, Hashimoto's thyroiditis, Henoch-Schonlein purpura, idiopathic thrombocytopenic purpura, IgA nephropathy, juvenile idiopathic arthritis, Kawasaki's disease, linear IgA disease (LAD), lupoid hepatitis, lupus erythematosus, Miller-Fisher syndrome, mixed connective tissue disease, multiple sclerosis, Myasthenia gravis, myositis, narcolepsy, neuromyelitis optica, neuromyotonia, paroxysmal nocturnal hemoglobinuria (PNH), pemphigus vulgaris, pernicious anaemia, polyarteritis nodosa, polymyalgia rheumatica, polymyositis, primary biliary cirrhosis, primary sclerosing cholangitis, psoriasis, psoriatic arthritis, pyoderma gangrenosum, pure red cell aplasia, Raynaud phenomenon, relapsing polychondritis, Reiter's syndrome, restless leg syndrome, retroperitoneal fibrosis, rheumatoid arthritis, rheumatic fever, sarcoidosis, schizophrenia, scleritis, scleroderma, serum sickness, Sjögren's syndrome, spondyloarthropathy, Still's disease, Sweet's syndrome, systemic lupus erythematosus, Takayasu's arteritis, temporal arteritis, thrombocytopenia, transverse myelitis, ulcerative colitis, vasculitis, vitiligo, and Wegener's granulomatosis.

2. The method according to claim 1, wherein said autoimmune disease is selected from the group consisting of drug-induced lupus, discoid lupus erythematosus, lupus erythematosus, rheumatoid arthritis, scleroderma, Sjögren's syndrome, and systemic lupus erythematosus.

3. The method according to claim 1, wherein said autoimmune disease is systemic lupus erythematosus.

4. The method according to claim 1, wherein said pharmaceutical composition further comprises at least one carrier.

5. The method according to claim 1, wherein said pharmaceutical composition is administered subcutaneously or parenterally.

6. The method according to claim 1, wherein said immune suppressive domain is from a virus of the Influenza virus A genus.

7. The method according to claim 1, wherein said immune suppressive domain comprises SEQ ID NO: 4.

8. The method according to claim 1, wherein said immune suppressive domain comprises SEQ ID NO: 287.

9. The method according to claim 1, wherein said immune suppressive domain is connected to at least one additional immune suppressive domain to form a dimer.

10. The method according to claim 9, wherein said dimer is homologous and comprises at least two immune suppressive domains with SEQ ID NO. 4, wherein said immune suppressive domains are cross-linked by a disulfide bond at the N-terminal or the C-terminal.

11. The method according to claim 7, wherein said autoimmune disease is selected from the group consisting of drug-induced lupus, discoid lupus erythematosus, lupus erythematosus, rheumatoid arthritis, scleroderma, Sjögren's syndrome, and systemic lupus erythematosus.

12. The method according to claim 7, wherein said autoimmune disease is systemic lupus erythematosus.

13. The method according to claim 7, wherein said pharmaceutical composition further comprises at least one carrier.

14. The method according to claim 7, wherein said pharmaceutical composition is administered subcutaneously or parenterally.

15. The method according to claim 7, wherein said immune suppressive domain is connected to at least one additional immune suppressive domain to form a dimer.

16. The method according to claim 15, wherein said dimer is homologous and comprises at least two immune suppressive domains with SEQ ID NO. 4, wherein said immune suppressive domains are cross-linked by a disulfide bond at the N-terminal or the C-terminal.

17. The method according to claim 8, wherein said autoimmune disease is selected from the group consisting of drug-induced lupus, discoid lupus erythematosus, lupus erythematosus, rheumatoid arthritis, scleroderma, Sjögren's syndrome, and systemic lupus erythematosus.

18. The method according to claim 8, wherein said autoimmune disease is systemic lupus erythematosus.

19. The method according to claim 8, wherein said pharmaceutical composition further comprises at least one carrier.

20. The method according to claim 8, wherein said pharmaceutical composition is administered subcutaneously or parenterally.

21. The method according to claim 8, wherein said immune suppressive domain is connected to at least one additional immune suppressive domain to form a dimer.

22. The method according to claim 21, wherein said dimer is homologous and comprises at least two immune suppressive domains with SEQ ID NO. 4, wherein said immune suppressive domains are cross-linked by a disulfide bond at the N-terminal or the C-terminal.

* * * * *

SEQUENCE LISTING

```
<160> NUMBER OF SEQ ID NOS: 301

<210> SEQ ID NO 1
<211> LENGTH: 27
<212> TYPE: PRT
<213> ORGANISM: Vesiculovirus

<400> SEQUENCE: 1

Val Gln Val Thr Pro His His Val Leu Val Asp Glu Tyr Thr Gly Glu
1               5                   10                  15

Trp Val Asp Ser Gln Phe Ile Asn Gly Lys Cys
            20                  25


<210> SEQ ID NO 2
<211> LENGTH: 14
<212> TYPE: PRT
<213> ORGANISM: flavivirus

<400> SEQUENCE: 2

Asp Arg Gly Trp Gly Asn Gly Cys Gly Leu Phe Gly Lys Gly
1               5                   10


<210> SEQ ID NO 3
<211> LENGTH: 17
<212> TYPE: PRT
<213> ORGANISM: Hepatitis C virus

<400> SEQUENCE: 3

Gly Leu Ile His Leu His Gln Asn Ile Val Asp Val Gln Tyr Leu Tyr
1               5                   10                  15

Gly


<210> SEQ ID NO 4
<211> LENGTH: 16
<212> TYPE: PRT
<213> ORGANISM: Influenza A and B virus

<400> SEQUENCE: 4

Gly Leu Phe Gly Ala Ile Ala Gly Phe Ile Glu Asn Gly Trp Glu Gly
1               5                   10                  15


<210> SEQ ID NO 5
```

<211> LENGTH: 22
<212> TYPE: PRT
<213> ORGANISM: Rabies virus

<400> SEQUENCE: 5

Gly Phe Thr Cys Thr Gly Val Val Thr Glu Ala Glu Thr Tyr Thr Asn
1 5 10 15

Phe Val Gly Tyr Val Thr
20

<210> SEQ ID NO 6
<211> LENGTH: 18
<212> TYPE: PRT
<213> ORGANISM: Rabies virus

<400> SEQUENCE: 6

Ser Leu His Asn Pro Tyr Pro Asp Tyr Arg Trp Leu Arg Thr Val Lys
1 5 10 15

Thr Thr

<210> SEQ ID NO 7
<211> LENGTH: 19
<212> TYPE: PRT
<213> ORGANISM: Aroa virus

<400> SEQUENCE: 7

Gly Asp Ala Ala Trp Asp Phe Gly Ser Val Gly Gly Val Phe Asn Ser
1 5 10 15

Leu Gly Lys

<210> SEQ ID NO 8
<211> LENGTH: 19
<212> TYPE: PRT
<213> ORGANISM: Dengue

<400> SEQUENCE: 8

Gly Gly Thr Ala Trp Asp Phe Gly Ser Ile Gly Gly Val Phe Thr Ser
1 5 10 15

Val Gly Lys

<210> SEQ ID NO 9
<211> LENGTH: 19
<212> TYPE: PRT
<213> ORGANISM: Dengue

<400> SEQUENCE: 9

Gly Asp Thr Ala Trp Asp Phe Gly Ser Leu Gly Gly Val Phe Thr Ser
1 5 10 15

Val Gly Lys

<210> SEQ ID NO 10
<211> LENGTH: 19
<212> TYPE: PRT
<213> ORGANISM: Dengue

<400> SEQUENCE: 10

Gly Glu Thr Ala Trp Asp Phe Gly Ser Val Gly Gly Leu Leu Thr Ser
1 5 10 15

Leu Gly Lys

<210> SEQ ID NO 11

-continued

<211> LENGTH: 19
<212> TYPE: PRT
<213> ORGANISM: Japanese encephalitis virus

<400> SEQUENCE: 11

Leu Gly Asp Thr Ala Trp Asp Phe Gly Ser Ile Gly Gly Val Phe Asn
1 5 10 15

Ser Ile Gly

<210> SEQ ID NO 12
<211> LENGTH: 19
<212> TYPE: PRT
<213> ORGANISM: Koutango virus

<400> SEQUENCE: 12

Leu Gly Asp Thr Ala Trp Asp Phe Gly Ser Val Gly Gly Ile Phe Thr
1 5 10 15

Ser Leu Gly

<210> SEQ ID NO 13
<211> LENGTH: 19
<212> TYPE: PRT
<213> ORGANISM: Murray Valley encephalitis virus

<400> SEQUENCE: 13

Leu Gly Asp Thr Ala Trp Asp Phe Gly Ser Val Gly Gly Val Phe Asn
1 5 10 15

Ser Ile Gly

<210> SEQ ID NO 14
<211> LENGTH: 19
<212> TYPE: PRT
<213> ORGANISM: Usutu virus

<400> SEQUENCE: 14

Leu Gly Asp Thr Ala Trp Asp Phe Gly Ser Val Gly Gly Ile Phe Asn
1 5 10 15

Ser Val Gly

<210> SEQ ID NO 15
<211> LENGTH: 19
<212> TYPE: PRT
<213> ORGANISM: West Nile virus

<400> SEQUENCE: 15

Leu Gly Asp Thr Ala Trp Asp Phe Gly Ser Val Gly Gly Val Phe Thr
1 5 10 15

Ser Val Gly

<210> SEQ ID NO 16
<211> LENGTH: 19
<212> TYPE: PRT
<213> ORGANISM: Kokobera virus

<400> SEQUENCE: 16

Ile Gly Asp Asp Ala Trp Asp Phe Gly Ser Val Gly Gly Ile Leu Asn
1 5 10 15

Ser Val Gly

<210> SEQ ID NO 17
<211> LENGTH: 19

<212> TYPE: PRT
<213> ORGANISM: Modoc virus

<400> SEQUENCE: 17

Val Gly Ser Ala Phe Trp Asn Ser Asp Gln Arg Phe Ser Ala Ile Asn
1 5 10 15

Leu Met Asp

<210> SEQ ID NO 18
<211> LENGTH: 14
<212> TYPE: PRT
<213> ORGANISM: Modoc virus

<400> SEQUENCE: 18

Asp Arg Gly Trp Gly Asn Gly Cys Ala Leu Phe Gly Lys Gly
1 5 10

<210> SEQ ID NO 19
<211> LENGTH: 19
<212> TYPE: PRT
<213> ORGANISM: Sepik virus

<400> SEQUENCE: 19

Thr Gly Glu His Ser Trp Asp Phe Gly Ser Thr Gly Gly Phe Phe Ala
1 5 10 15

Ser Val Gly

<210> SEQ ID NO 20
<211> LENGTH: 19
<212> TYPE: PRT
<213> ORGANISM: Bagaza virus

<400> SEQUENCE: 20

Leu Gly Asp Thr Ala Trp Asp Phe Gly Ser Val Gly Gly Phe Phe Thr
1 5 10 15

Ser Leu Gly

<210> SEQ ID NO 21
<211> LENGTH: 19
<212> TYPE: PRT
<213> ORGANISM: Yokose virus

<400> SEQUENCE: 21

Ile Gly Asp Asp Ala Trp Asp Phe Gly Ser Thr Gly Gly Ile Phe Asn
1 5 10 15

Thr Ile Gly

<210> SEQ ID NO 22
<211> LENGTH: 20
<212> TYPE: PRT
<213> ORGANISM: Apoi virus

<400> SEQUENCE: 22

Ser Ser Ala Phe Trp Asn Ser Asp Glu Pro Phe His Phe Ser Asn Leu
1 5 10 15

Ile Ser Ile Ile
20

<210> SEQ ID NO 23
<211> LENGTH: 20
<212> TYPE: PRT
<213> ORGANISM: Entebbe bat virus

<400> SEQUENCE: 23

Gly Asp Asp Ala Trp Asp Phe Gly Ser Thr Gly Gly Ile Phe Asn Thr
1               5                   10                  15

Ile Gly Lys Ala
            20

<210> SEQ ID NO 24
<211> LENGTH: 20
<212> TYPE: PRT
<213> ORGANISM: Rio Bravo virus

<400> SEQUENCE: 24

Ser Ser Ala Tyr Trp Ser Ser Ser Glu Pro Phe Thr Ser Ala Gly Ile
1               5                   10                  15

Met Arg Ile Leu
            20

<210> SEQ ID NO 25
<211> LENGTH: 20
<212> TYPE: PRT
<213> ORGANISM: Saboya virus

<400> SEQUENCE: 25

Gly Ser Ser Ser Trp Asp Phe Ser Ser Ala Gly Gly Phe Phe Gly Ser
1               5                   10                  15

Ile Gly Lys Ala
            20

<210> SEQ ID NO 26
<211> LENGTH: 20
<212> TYPE: PRT
<213> ORGANISM: Meaban virus

<400> SEQUENCE: 26

Gly Asp Ala Ala Trp Asp Phe Gly Ser Val Gly Gly Phe Met Thr Ser
1               5                   10                  15

Ile Gly Arg Ala
            20

<210> SEQ ID NO 27
<211> LENGTH: 14
<212> TYPE: PRT
<213> ORGANISM: Meaban virus

<400> SEQUENCE: 27

Asp Arg Gly Trp Gly Asn His Cys Gly Leu Phe Gly Lys Gly
1               5                   10

<210> SEQ ID NO 28
<211> LENGTH: 20
<212> TYPE: PRT
<213> ORGANISM: Saumarez Reef virus

<400> SEQUENCE: 28

Gly Glu Thr Ala Trp Asp Phe Gly Ser Ala Gly Gly Phe Phe Thr Ser
1               5                   10                  15

Val Gly Arg Gly
            20

<210> SEQ ID NO 29
<211> LENGTH: 20

<212> TYPE: PRT
<213> ORGANISM: Tyuleniy virus

<400> SEQUENCE: 29

```
Gly Glu Ala Ala Trp Asp Phe Gly Ser Ala Gly Gly Phe Phe Gln Ser
1               5                   10                  15

Val Gly Arg Gly
            20
```

<210> SEQ ID NO 30
<211> LENGTH: 20
<212> TYPE: PRT
<213> ORGANISM: Zika virus

<400> SEQUENCE: 30

```
Leu Gly Asp Thr Ala Trp Asp Phe Gly Ser Val Gly Gly Val Phe Asn
1               5                   10                  15

Ser Leu Gly Lys
            20
```

<210> SEQ ID NO 31
<211> LENGTH: 19
<212> TYPE: PRT
<213> ORGANISM: Kyasanur forest disease virus

<400> SEQUENCE: 31

```
Val Gly Glu His Ala Trp Asp Phe Gly Ser Val Gly Gly Met Leu Ser
1               5                   10                  15

Ser Val Gly
```

<210> SEQ ID NO 32
<211> LENGTH: 20
<212> TYPE: PRT
<213> ORGANISM: Langat virus

<400> SEQUENCE: 32

```
Val Leu Gly Glu His Ala Trp Asp Phe Gly Ser Val Gly Gly Val Met
1               5                   10                  15

Thr Ser Ile Gly
            20
```

<210> SEQ ID NO 33
<211> LENGTH: 19
<212> TYPE: PRT
<213> ORGANISM: Louping ill virus

<400> SEQUENCE: 33

```
Ile Gly Glu His Ala Trp Asp Phe Gly Ser Ala Gly Gly Phe Phe Ser
1               5                   10                  15

Ser Ile Gly
```

<210> SEQ ID NO 34
<211> LENGTH: 19
<212> TYPE: PRT
<213> ORGANISM: Omsk hemorrhagic fever virus

<400> SEQUENCE: 34

```
Leu Gly Glu His Ala Trp Asp Phe Gly Ser Thr Gly Gly Phe Leu Ser
1               5                   10                  15

Ser Ile Gly
```

<210> SEQ ID NO 35
<211> LENGTH: 19
<212> TYPE: PRT
<213> ORGANISM: Powassan virus

<400> SEQUENCE: 35

Val Gly Glu His Ala Trp Asp Phe Gly Ser Val Gly Gly Ile Leu Ser
1               5                   10                  15

Ser Val Gly

<210> SEQ ID NO 36
<211> LENGTH: 14
<212> TYPE: PRT
<213> ORGANISM: Powassan virus

<400> SEQUENCE: 36

Asp Arg Gly Trp Gly Asn His Cys Gly Phe Phe Gly Lys Gly
1               5                   10

<210> SEQ ID NO 37
<211> LENGTH: 19
<212> TYPE: PRT
<213> ORGANISM: Tick-borne encephalitis virus

<400> SEQUENCE: 37

Ile Gly Glu His Ala Trp Asp Phe Gly Ser Ala Gly Gly Phe Leu Ser
1               5                   10                  15

Ser Ile Gly

<210> SEQ ID NO 38
<211> LENGTH: 19
<212> TYPE: PRT
<213> ORGANISM: Tick-borne encephalitis virus

<400> SEQUENCE: 38

Ile Gly Glu His Ala Trp Asp Phe Gly Ser Thr Gly Gly Phe Leu Thr
1               5                   10                  15

Ser Val Gly

<210> SEQ ID NO 39
<211> LENGTH: 19
<212> TYPE: PRT
<213> ORGANISM: Tick-borne encephalitis virus

<400> SEQUENCE: 39

Ile Gly Glu His Ala Trp Asp Phe Gly Ser Thr Gly Gly Phe Leu Ala
1               5                   10                  15

Ser Val Gly

<210> SEQ ID NO 40
<211> LENGTH: 19
<212> TYPE: PRT
<213> ORGANISM: Yaounde virus

<400> SEQUENCE: 40

Leu Gly Asp Thr Ala Trp Asp Phe Gly Ser Ile Gly Gly Val Phe Thr
1               5                   10                  15

Ser Leu Gly

<210> SEQ ID NO 41
<211> LENGTH: 19
<212> TYPE: PRT

-continued

<213> ORGANISM: Banzi virus

<400> SEQUENCE: 41

Val Gly Ser Ser Ser Trp Asp Phe Ser Ser Thr Ser Gly Phe Phe Ser
1 5 10 15

Ser Val Gly

<210> SEQ ID NO 42
<211> LENGTH: 19
<212> TYPE: PRT
<213> ORGANISM: Bouboui virus

<400> SEQUENCE: 42

Val Gly Arg Ser Ser Trp Asp Phe Ser Ser Ala Gly Gly Phe Phe Ser
1 5 10 15

Ser Val Gly

<210> SEQ ID NO 43
<211> LENGTH: 19
<212> TYPE: PRT
<213> ORGANISM: Yellow fever virus

<400> SEQUENCE: 43

Met Gly Asp Thr Ala Trp Asp Phe Ser Ser Ala Gly Gly Phe Phe Thr
1 5 10 15

Ser Val Gly

<210> SEQ ID NO 44
<211> LENGTH: 14
<212> TYPE: PRT
<213> ORGANISM: Unclassified Flavivirus and culex flavivirus

<400> SEQUENCE: 44

Asn Arg Gly Trp Gly Thr Gly Cys Phe Lys Trp Gly Ile Gly
1 5 10

<210> SEQ ID NO 45
<211> LENGTH: 14
<212> TYPE: PRT
<213> ORGANISM: Unclassified Flavivirus and aedes flavirus

<400> SEQUENCE: 45

Asn Arg Gly Trp Gly Thr Gly Cys Phe Glu Trp Gly Leu Gly
1 5 10

<210> SEQ ID NO 46
<211> LENGTH: 23
<212> TYPE: PRT
<213> ORGANISM: Aedes flavivirus

<400> SEQUENCE: 46

His Val Ala Gly Arg Tyr Ser Lys His Gly Met Ala Gly Ile Gly Ser
1 5 10 15

Val Trp Glu Asp Leu Val Arg
20

<210> SEQ ID NO 47
<211> LENGTH: 14
<212> TYPE: PRT
<213> ORGANISM: Culex flavivirus

<400> SEQUENCE: 47

```
Val Asp Lys Tyr Arg Arg Phe Gly Thr Ala Gly Val Gly Gly
1               5                   10


<210> SEQ ID NO 48
<211> LENGTH: 17
<212> TYPE: PRT
<213> ORGANISM: Hepatitis C virus

<400> SEQUENCE: 48

Gly Leu Ile His Leu His Arg Asn Ile Val Asp Val Gln Tyr Leu Tyr
1               5                   10                  15

Gly


<210> SEQ ID NO 49
<211> LENGTH: 17
<212> TYPE: PRT
<213> ORGANISM: Hepatitis C virus

<400> SEQUENCE: 49

Gly Leu Ile His Leu His Gln Asn Ile Val Asp Val Gln Tyr Met Tyr
1               5                   10                  15

Gly


<210> SEQ ID NO 50
<211> LENGTH: 17
<212> TYPE: PRT
<213> ORGANISM: Hepatitis C virus

<400> SEQUENCE: 50

Gly Leu Ile His Leu His Gln Asn Ile Val Asp Thr Gln Tyr Leu Tyr
1               5                   10                  15

Gly


<210> SEQ ID NO 51
<211> LENGTH: 24
<212> TYPE: PRT
<213> ORGANISM: Border disease virus

<400> SEQUENCE: 51

Asn Thr Thr Leu Leu Asn Gly Ser Ala Phe Gln Leu Ile Cys Pro Tyr
1               5                   10                  15

Gly Trp Val Gly Arg Val Glu Cys
            20


<210> SEQ ID NO 52
<211> LENGTH: 19
<212> TYPE: PRT
<213> ORGANISM: Border disease virus

<400> SEQUENCE: 52

Ser Tyr Phe Gln Gln Tyr Met Leu Lys Gly Gln Tyr Gln Tyr Trp Phe
1               5                   10                  15

Asp Leu Glu


<210> SEQ ID NO 53
<211> LENGTH: 24
<212> TYPE: PRT
<213> ORGANISM: Bovine viral diarrhea virus

<400> SEQUENCE: 53

Asn Thr Thr Leu Leu Asn Gly Pro Ala Phe Gln Met Val Cys Pro Leu
1               5                   10                  15
```

Gly Trp Thr Gly Thr Val Ser Cys
            20

<210> SEQ ID NO 54
<211> LENGTH: 19
<212> TYPE: PRT
<213> ORGANISM: Bovine viral diarrhea virus

<400> SEQUENCE: 54

Ser Tyr Phe Gln Gln Tyr Met Leu Lys Gly Glu Tyr Gln Tyr Trp Phe
1               5                   10                  15

Asp Leu Glu

<210> SEQ ID NO 55
<211> LENGTH: 22
<212> TYPE: PRT
<213> ORGANISM: Bovine viral diarrhea virus

<400> SEQUENCE: 55

Ser Leu Leu Asn Gly Pro Ala Phe Gln Met Val Cys Pro Gln Gly Trp
1               5                   10                  15

Thr Gly Thr Ile Glu Cys
            20

<210> SEQ ID NO 56
<211> LENGTH: 20
<212> TYPE: PRT
<213> ORGANISM: Bovine viral diarrhea virus

<400> SEQUENCE: 56

Asp Arg Tyr Phe Gln Gln Tyr Met Leu Lys Gly Lys Trp Gln Tyr Trp
1               5                   10                  15

Phe Asp Leu Asp
            20

<210> SEQ ID NO 57
<211> LENGTH: 22
<212> TYPE: PRT
<213> ORGANISM: Classical swine fever virus

<400> SEQUENCE: 57

Thr Leu Leu Asn Gly Ser Ala Phe Tyr Leu Val Cys Pro Ile Gly Trp
1               5                   10                  15

Thr Gly Val Ile Glu Cys
            20

<210> SEQ ID NO 58
<211> LENGTH: 19
<212> TYPE: PRT
<213> ORGANISM: Classical swine fever virus

<400> SEQUENCE: 58

Ser Tyr Phe Gln Gln Tyr Met Leu Lys Gly Glu Tyr Gln Tyr Trp Phe
1               5                   10                  15

Asp Leu Asp

<210> SEQ ID NO 59
<211> LENGTH: 22
<212> TYPE: PRT
<213> ORGANISM: Bovine viral diarrhea virus

<400> SEQUENCE: 59

-continued

```
Thr Leu Leu Asn Gly Pro Ala Phe Gln Leu Val Cys Pro Tyr Gly Trp
1               5                   10                  15

Thr Gly Thr Ile Glu Cys
            20


<210> SEQ ID NO 60
<211> LENGTH: 23
<212> TYPE: PRT
<213> ORGANISM: Bovine viral diarrhea virus

<400> SEQUENCE: 60

Asp Asn Tyr Phe Gln Gln Tyr Met Leu Lys Gly Lys Tyr Gln Tyr Trp
1               5                   10                  15

Phe Asp Leu Glu Ala Thr Asp
            20


<210> SEQ ID NO 61
<211> LENGTH: 22
<212> TYPE: PRT
<213> ORGANISM: Chamois pestivirus

<400> SEQUENCE: 61

Thr Leu Leu Asn Gly Ser Ala Phe Gln Met Val Cys Pro Phe Gly Trp
1               5                   10                  15

Thr Gly Gln Val Glu Cys
            20


<210> SEQ ID NO 62
<211> LENGTH: 23
<212> TYPE: PRT
<213> ORGANISM: Chamois pestivirus

<400> SEQUENCE: 62

Asp Ser Tyr Phe Gln Gln Tyr Met Leu Lys Gly Glu Tyr Gln Tyr Trp
1               5                   10                  15

Phe Asp Leu Asp Ala Lys Asp
            20


<210> SEQ ID NO 63
<211> LENGTH: 22
<212> TYPE: PRT
<213> ORGANISM: Alpha-virus

<400> SEQUENCE: 63

Gly Val Tyr Pro Phe Met Trp Gly Gly Ala Tyr Cys Phe Cys Asp Thr
1               5                   10                  15

Glu Asn Thr Gln Val Ser
            20


<210> SEQ ID NO 64
<211> LENGTH: 23
<212> TYPE: PRT
<213> ORGANISM: Alpha-virus

<400> SEQUENCE: 64

Ala Pro Phe Gly Cys Glu Ile Tyr Thr Asn Pro Ile Arg Ala Glu Asn
1               5                   10                  15

Cys Ala Val Gly Ser Ile Pro
            20


<210> SEQ ID NO 65
```

-continued

<211> LENGTH: 22
<212> TYPE: PRT
<213> ORGANISM: Alpha-virus

<400> SEQUENCE: 65

```
Ser Asp Phe Gly Gly Ile Ala Thr Val Lys Tyr Ser Ala Ser Lys Ser
1               5                   10                  15

Gly Lys Cys Ala Val His
            20
```

<210> SEQ ID NO 66
<211> LENGTH: 28
<212> TYPE: PRT
<213> ORGANISM: Alpha-virus

<400> SEQUENCE: 66

```
Phe Ser Thr Ala Asn Ile His Pro Glu Phe Arg Leu Gln Ile Cys Thr
1               5                   10                  15

Ser Tyr Val Thr Cys Lys Gly Asp Cys His Pro Pro
            20                  25
```

<210> SEQ ID NO 67
<211> LENGTH: 15
<212> TYPE: PRT
<213> ORGANISM: Venezuelan equine encephalitis virus

<400> SEQUENCE: 67

```
Gly Val Tyr Pro Phe Met Trp Gly Gly Ala Tyr Cys Phe Cys Asp
1               5                   10                  15
```

<210> SEQ ID NO 68
<211> LENGTH: 19
<212> TYPE: PRT
<213> ORGANISM: Venezuelan equine encephalitis virus

<400> SEQUENCE: 68

```
Gly Asp Cys His Pro Pro Lys Asp His Ile Val Thr His Pro Gln Tyr
1               5                   10                  15

His Ala Gln
```

<210> SEQ ID NO 69
<211> LENGTH: 12
<212> TYPE: PRT
<213> ORGANISM: Venezuelan equine encephalitis virus

<400> SEQUENCE: 69

```
Ala Val Ser Lys Thr Ala Trp Thr Trp Leu Thr Ser
1               5                   10
```

<210> SEQ ID NO 70
<211> LENGTH: 17
<212> TYPE: PRT
<213> ORGANISM: Chikungunya virus

<400> SEQUENCE: 70

```
Val His Cys Ala Ala Glu Cys His Pro Pro Lys Asp His Ile Val Asn
1               5                   10                  15

Tyr
```

<210> SEQ ID NO 71
<211> LENGTH: 20
<212> TYPE: PRT
<213> ORGANISM: Chikungunya virus

<400> SEQUENCE: 71

Pro Ala Ser His Thr Thr Leu Gly Val Gln Asp Ile Ser Ala Thr Ala
1 5 10 15

Met Ser Trp Val
20

<210> SEQ ID NO 72
<211> LENGTH: 30
<212> TYPE: PRT
<213> ORGANISM: Rubella virus

<400> SEQUENCE: 72

Ala Cys Thr Phe Trp Ala Val Asn Ala Tyr Ser Ser Gly Gly Tyr Ala
1 5 10 15

Gln Leu Ala Ser Tyr Phe Asn Pro Gly Gly Ser Tyr Tyr Lys
20 25 30

<210> SEQ ID NO 73
<211> LENGTH: 27
<212> TYPE: PRT
<213> ORGANISM: Rubella virus

<400> SEQUENCE: 73

Gln Tyr His Pro Thr Ala Cys Glu Val Glu Pro Ala Phe Gly His Ser
1 5 10 15

Asp Ala Ala Cys Trp Gly Phe Pro Thr Asp Thr
20 25

<210> SEQ ID NO 74
<211> LENGTH: 23
<212> TYPE: PRT
<213> ORGANISM: Rubella virus

<400> SEQUENCE: 74

Met Ser Val Phe Ala Leu Ala Ser Tyr Val Gln His Pro His Lys Thr
1 5 10 15

Val Arg Val Lys Phe His Thr
20

<210> SEQ ID NO 75
<211> LENGTH: 36
<212> TYPE: PRT
<213> ORGANISM: Human respiratory syncytial virus

<400> SEQUENCE: 75

Gly Ile Ile Arg Thr Leu Pro Asp Gly Cys His Tyr Ile Ser Asn Lys
1 5 10 15

Gly Val Asp Arg Val Gln Val Gly Asn Thr Val Tyr Tyr Leu Ser Lys
20 25 30

Glu Val Gly Lys
35

<210> SEQ ID NO 76
<211> LENGTH: 22
<212> TYPE: PRT
<213> ORGANISM: Rubella virus

<400> SEQUENCE: 76

Asn Val Thr Thr Glu His Pro Phe Cys Asn Met Pro His Gly Gln Leu
1 5 10 15

Glu Val Gln Val Pro Pro
20

<210> SEQ ID NO 77
<211> LENGTH: 20
<212> TYPE: PRT
<213> ORGANISM: Rubella virus

<400> SEQUENCE: 77

Asp Pro Gly Asp Leu Val Glu Tyr Ile Met Asn Tyr Thr Gly Asn Gln
1 5 10 15

Gln Ser Arg Trp
20

<210> SEQ ID NO 78
<211> LENGTH: 23
<212> TYPE: PRT
<213> ORGANISM: Rubella virus

<400> SEQUENCE: 78

Gly Ser Pro Asn Cys His Gly Pro Asp Trp Ala Ser Pro Val Cys Gln
1 5 10 15

Arg His Ser Pro Asp Cys Ser
20

<210> SEQ ID NO 79
<211> LENGTH: 15
<212> TYPE: PRT
<213> ORGANISM: Rubella virus

<400> SEQUENCE: 79

Arg Leu Val Gly Ala Thr Pro Glu Arg Pro Arg Leu Arg Leu Val
1 5 10 15

<210> SEQ ID NO 80
<211> LENGTH: 13
<212> TYPE: PRT
<213> ORGANISM: Rubella virus

<400> SEQUENCE: 80

Asp Ala Asp Asp Pro Leu Leu Arg Thr Ala Pro Gly Pro
1 5 10

<210> SEQ ID NO 81
<211> LENGTH: 18
<212> TYPE: PRT
<213> ORGANISM: Rubella virus

<400> SEQUENCE: 81

Gly Glu Val Trp Val Thr Pro Val Ile Gly Ser Gln Ala Arg Lys Cys
1 5 10 15

Gly Leu

<210> SEQ ID NO 82
<211> LENGTH: 17
<212> TYPE: PRT
<213> ORGANISM: Rabies virus

<400> SEQUENCE: 82

Gln His Met Glu Leu Leu Glu Ser Ser Val Ile Pro Leu Val His Pro
1 5 10 15

Leu

<210> SEQ ID NO 83
<211> LENGTH: 19
<212> TYPE: PRT
<213> ORGANISM: Tembusu virus

<400> SEQUENCE: 83

Leu Gly Asp Thr Ala Trp Asp Phe Gly Ser Val Gly Gly Val Leu Thr
1 5 10 15

Ser Ile Gly

<210> SEQ ID NO 84
<211> LENGTH: 19
<212> TYPE: PRT
<213> ORGANISM: Ilheus virus

<400> SEQUENCE: 84

Leu Gly Asp Thr Ala Trp Asp Phe Gly Ser Val Gly Gly Ile Phe Asn
1 5 10 15

Ser Ile Gly

<210> SEQ ID NO 85
<211> LENGTH: 14
<212> TYPE: PRT
<213> ORGANISM: Aroa virus

<400> SEQUENCE: 85

Asn Arg Gly Trp Asn Asn Gly Cys Gly Leu Phe Gly Lys Gly
1 5 10

<210> SEQ ID NO 86
<211> LENGTH: 14
<212> TYPE: PRT
<213> ORGANISM: Rubella virus

<400> SEQUENCE: 86

His Ile Arg Ala Gly Pro Tyr Gly His Ala Thr Val Glu Met
1 5 10

<210> SEQ ID NO 87
<211> LENGTH: 15
<212> TYPE: PRT
<213> ORGANISM: Rubella virus

<400> SEQUENCE: 87

Pro Glu Trp Ile His Ala His Thr Thr Ser Asp Pro Trp His Pro
1 5 10 15

<210> SEQ ID NO 88
<211> LENGTH: 18
<212> TYPE: PRT
<213> ORGANISM: Rubella virus

<400> SEQUENCE: 88

Pro Gly Pro Leu Gly Leu Lys Phe Lys Thr Val Arg Pro Val Ala Leu
1 5 10 15

Pro Arg

<210> SEQ ID NO 89
<211> LENGTH: 21
<212> TYPE: PRT
<213> ORGANISM: Rubella virus

<400> SEQUENCE: 89

Ala Leu Ala Pro Pro Arg Asn Val Arg Val Thr Gly Cys Tyr Gln Cys
1               5                   10                  15

Gly Thr Pro Ala Leu
            20

<210> SEQ ID NO 90
<211> LENGTH: 20
<212> TYPE: PRT
<213> ORGANISM: Rubella virus

<400> SEQUENCE: 90

Glu Gly Leu Ala Pro Gly Gly Gly Asn Cys His Leu Thr Val Asn Gly
1               5                   10                  15

Glu Asp Val Gly
            20

<210> SEQ ID NO 91
<211> LENGTH: 17
<212> TYPE: PRT
<213> ORGANISM: Rabies virus

<400> SEQUENCE: 91

Cys Lys Leu Lys Leu Cys Gly Val Leu Gly Leu Arg Leu Met Asp Gly
1               5                   10                  15

Thr

<210> SEQ ID NO 92
<211> LENGTH: 23
<212> TYPE: PRT
<213> ORGANISM: Rubella virus

<400> SEQUENCE: 92

Arg Ala Ser Ala Arg Val Ile Asp Pro Ala Ala Gln Ser Phe Thr Gly
1               5                   10                  15

Val Val Tyr Gly Thr His Thr
            20

<210> SEQ ID NO 93
<211> LENGTH: 24
<212> TYPE: PRT
<213> ORGANISM: Hanta-virus

<400> SEQUENCE: 93

Thr Ala Val Ser Glu Thr Arg Gln Thr Trp Ala Glu Trp Ala Ala Ala
1               5                   10                  15

His Trp Trp Gln Leu Thr Leu Gly
            20

<210> SEQ ID NO 94
<211> LENGTH: 20
<212> TYPE: PRT
<213> ORGANISM: Hanta-virus

<400> SEQUENCE: 94

Asn Pro Pro Asp Cys Pro Gly Val Gly Thr Gly Cys Thr Ala Cys Gly
1               5                   10                  15

Val Tyr Leu Asp
            20

<210> SEQ ID NO 95
<211> LENGTH: 21

```
<212> TYPE: PRT
<213> ORGANISM: Hanta-virus

<400> SEQUENCE: 95

Arg Lys Val Cys Ile Gln Leu Gly Thr Glu Gln Thr Cys Lys Thr Ile
1               5                   10                  15

Asp Ser Asn Asp Cys
            20


<210> SEQ ID NO 96
<211> LENGTH: 33
<212> TYPE: PRT
<213> ORGANISM: Hanta-virus

<400> SEQUENCE: 96

Asp Thr Leu Leu Phe Leu Gly Pro Leu Glu Glu Gly Gly Met Ile Phe
1               5                   10                  15

Lys Gln Trp Cys Thr Thr Thr Cys Gln Phe Gly Asp Pro Gly Asp Ile
            20                  25                  30

Met


<210> SEQ ID NO 97
<211> LENGTH: 24
<212> TYPE: PRT
<213> ORGANISM: Hanta-virus

<400> SEQUENCE: 97

Gly Ser Phe Arg Lys Lys Cys Ser Phe Ala Thr Leu Pro Ser Cys Gln
1               5                   10                  15

Tyr Asp Gly Asn Thr Val Ser Gly
            20


<210> SEQ ID NO 98
<211> LENGTH: 15
<212> TYPE: PRT
<213> ORGANISM: Hanta-virus

<400> SEQUENCE: 98

Ala Thr Lys Asp Ser Phe Gln Ser Phe Asn Ile Thr Glu Pro His
1               5                   10                  15


<210> SEQ ID NO 99
<211> LENGTH: 17
<212> TYPE: PRT
<213> ORGANISM: Hanta-virus

<400> SEQUENCE: 99

Gly Ser Gly Val Gly Phe Asn Leu Val Cys Ser Val Ser Leu Thr Glu
1               5                   10                  15

Cys


<210> SEQ ID NO 100
<211> LENGTH: 22
<212> TYPE: PRT
<213> ORGANISM: Hanta-virus

<400> SEQUENCE: 100

Lys Ala Cys Asp Ser Ala Met Cys Tyr Gly Ser Ser Thr Ala Asn Leu
1               5                   10                  15

Val Arg Gly Gln Asn Thr
            20
```

<210> SEQ ID NO 101
<211> LENGTH: 30
<212> TYPE: PRT
<213> ORGANISM: Hanta-virus

<400> SEQUENCE: 101

Gly Lys Gly Gly His Ser Gly Ser Lys Phe Met Cys Cys His Asp Lys
1 5 10 15

Lys Cys Ser Ala Thr Gly Leu Val Ala Ala Ala Pro His Leu
20 25 30

<210> SEQ ID NO 102
<211> LENGTH: 19
<212> TYPE: PRT
<213> ORGANISM: Hanta-virus

<400> SEQUENCE: 102

Asp Asp Gly Ala Pro Gln Cys Gly Val His Cys Trp Phe Lys Lys Ser
1 5 10 15

Gly Glu Trp

<210> SEQ ID NO 103
<211> LENGTH: 22
<212> TYPE: PRT
<213> ORGANISM: Ortho-bunya-virus

<400> SEQUENCE: 103

Lys His Asp Glu Leu Cys Thr Gly Pro Cys Pro Val Asn Ile Asn His
1 5 10 15

Gln Thr Gly Trp Leu Thr
20

<210> SEQ ID NO 104
<211> LENGTH: 22
<212> TYPE: PRT
<213> ORGANISM: Ortho-bunya-virus

<400> SEQUENCE: 104

Trp Gly Cys Glu Glu Phe Gly Cys Leu Ala Val Ser Asp Gly Cys Val
1 5 10 15

Phe Gly Ser Cys Gln Asp
20

<210> SEQ ID NO 105
<211> LENGTH: 24
<212> TYPE: PRT
<213> ORGANISM: Ortho-bunya-virus

<400> SEQUENCE: 105

Gly Asn Gly Val Pro Arg Phe Asp Tyr Leu Cys His Leu Ala Ser Arg
1 5 10 15

Lys Glu Val Ile Val Arg Lys Cys
20

<210> SEQ ID NO 106
<211> LENGTH: 14
<212> TYPE: PRT
<213> ORGANISM: Ortho-bunya-virus

<400> SEQUENCE: 106

Ser Cys Ala Gly Cys Ile Asn Cys Phe Gln Asn Ile His Cys
1 5 10

<210> SEQ ID NO 107
<211> LENGTH: 17
<212> TYPE: PRT
<213> ORGANISM: Rift Valley fever virus

<400> SEQUENCE: 107

```
Lys Thr Val Ser Ser Glu Leu Ser Cys Arg Glu Gly Gln Ser Tyr Trp
1               5                   10                  15

Thr
```

<210> SEQ ID NO 108
<211> LENGTH: 13
<212> TYPE: PRT
<213> ORGANISM: Rift Valley fever virus

<400> SEQUENCE: 108

```
Gly Ser Phe Ser Pro Lys Cys Leu Ser Ser Arg Arg Cys
1               5                   10
```

<210> SEQ ID NO 109
<211> LENGTH: 27
<212> TYPE: PRT
<213> ORGANISM: Rift Valley fever virus

<400> SEQUENCE: 109

```
Glu Asn Lys Cys Phe Glu Gln Cys Gly Gly Trp Gly Cys Gly Cys Phe
1               5                   10                  15

Asn Val Asn Pro Ser Cys Leu Phe Val His Thr
            20                  25
```

<210> SEQ ID NO 110
<211> LENGTH: 21
<212> TYPE: PRT
<213> ORGANISM: Rift Valley fever virus

<400> SEQUENCE: 110

```
Trp Gly Ser Val Ser Leu Ser Leu Asp Ala Glu Gly Ile Ser Gly Ser
1               5                   10                  15

Asn Ser Phe Ser Phe
            20
```

<210> SEQ ID NO 111
<211> LENGTH: 13
<212> TYPE: PRT
<213> ORGANISM: Rift Valley fever virus

<400> SEQUENCE: 111

```
Arg Gln Gly Phe Leu Gly Glu Ile Arg Cys Asn Ser Glu
1               5                   10
```

<210> SEQ ID NO 112
<211> LENGTH: 23
<212> TYPE: PRT
<213> ORGANISM: Rift Valley fever virus

<400> SEQUENCE: 112

```
Ala His Glu Ser Cys Leu Arg Ala Pro Asn Leu Val Ser Tyr Lys Pro
1               5                   10                  15

Met Ile Asp Gln Leu Glu Cys
            20
```

<210> SEQ ID NO 113
<211> LENGTH: 15
<212> TYPE: PRT
<213> ORGANISM: Rift Valley fever virus

<400> SEQUENCE: 113

Asp Pro Phe Val Val Phe Glu Arg Gly Ser Leu Pro Gln Thr Arg
1 5 10 15

<210> SEQ ID NO 114
<211> LENGTH: 17
<212> TYPE: PRT
<213> ORGANISM: Rift Valley fever virus

<400> SEQUENCE: 114

Gln Ala Phe Ser Lys Gly Ser Val Gln Ala Asp Leu Thr Leu Met Phe
1 5 10 15

Asp

<210> SEQ ID NO 115
<211> LENGTH: 17
<212> TYPE: PRT
<213> ORGANISM: Rift Valley fever virus

<400> SEQUENCE: 115

Cys Asp Ala Ala Phe Leu Asn Leu Thr Gly Cys Tyr Ser Cys Asn Ala
1 5 10 15

Gly

<210> SEQ ID NO 116
<211> LENGTH: 19
<212> TYPE: PRT
<213> ORGANISM: Rift Valley fever virus

<400> SEQUENCE: 116

Cys Gln Ile Leu His Phe Thr Val Pro Glu Val Glu Glu Glu Phe Met
1 5 10 15

Tyr Ser Cys

<210> SEQ ID NO 117
<211> LENGTH: 12
<212> TYPE: PRT
<213> ORGANISM: Rift Valley fever virus

<400> SEQUENCE: 117

Ser Thr Val Val Asn Pro Lys Ser Gly Ser Trp Asn
1 5 10

<210> SEQ ID NO 118
<211> LENGTH: 17
<212> TYPE: PRT
<213> ORGANISM: Rift Valley fever virus

<400> SEQUENCE: 118

Phe Phe Asp Trp Phe Ser Gly Leu Met Ser Trp Phe Gly Gly Pro Leu
1 5 10 15

Lys

<210> SEQ ID NO 119
<211> LENGTH: 16
<212> TYPE: PRT
<213> ORGANISM: Influenza A virus

<400> SEQUENCE: 119

Gly Leu Phe Gly Ala Ile Ala Gly Phe Ile Glu Gly Gly Trp Thr Gly
1 5 10 15

<210> SEQ ID NO 120
<211> LENGTH: 16
<212> TYPE: PRT
<213> ORGANISM: Influenza A virus

<400> SEQUENCE: 120

Gly Leu Phe Gly Ala Ile Ala Gly Phe Ile Glu Gly Gly Trp Gln Gly
1 5 10 15

<210> SEQ ID NO 121
<211> LENGTH: 16
<212> TYPE: PRT
<213> ORGANISM: Influenza A virus

<400> SEQUENCE: 121

Gly Ile Phe Gly Ala Ile Ala Gly Phe Ile Glu Asn Gly Trp Glu Gly
1 5 10 15

<210> SEQ ID NO 122
<211> LENGTH: 16
<212> TYPE: PRT
<213> ORGANISM: Influenza A virus

<400> SEQUENCE: 122

Gly Leu Phe Gly Ala Ile Ala Gly Phe Ile Glu Asn Gly Trp Gln Gly
1 5 10 15

<210> SEQ ID NO 123
<211> LENGTH: 16
<212> TYPE: PRT
<213> ORGANISM: Influenza A virus

<400> SEQUENCE: 123

Gly Ile Phe Gly Ala Ile Ala Gly Phe Ile Glu Gly Gly Trp Thr Gly
1 5 10 15

<210> SEQ ID NO 124
<211> LENGTH: 16
<212> TYPE: PRT
<213> ORGANISM: Influenza A virus

<400> SEQUENCE: 124

Gly Leu Phe Gly Ala Ile Ala Gly Phe Ile Glu Gly Gly Trp Ser Gly
1 5 10 15

<210> SEQ ID NO 125
<211> LENGTH: 16
<212> TYPE: PRT
<213> ORGANISM: Influenza A virus

<400> SEQUENCE: 125

Gly Leu Phe Gly Ala Ile Ala Gly Phe Ile Glu Gly Gly Trp Pro Gly
1 5 10 15

<210> SEQ ID NO 126
<211> LENGTH: 16
<212> TYPE: PRT
<213> ORGANISM: Influenza A virus

<400> SEQUENCE: 126

Gly Phe Phe Gly Ala Ile Ala Gly Phe Leu Glu Gly Gly Trp Glu Gly
1 5 10 15

<210> SEQ ID NO 127
<211> LENGTH: 16
<212> TYPE: PRT
<213> ORGANISM: Avulavirus

<400> SEQUENCE: 127

Gly Ala Ile Ala Leu Gly Val Ala Thr Ala Ala Ala Val Thr Ala Gly
1 5 10 15

<210> SEQ ID NO 128
<211> LENGTH: 17
<212> TYPE: PRT
<213> ORGANISM: Human respiratory syncytial virus

<400> SEQUENCE: 128

Phe Leu Gly Leu Ile Leu Gly Leu Gly Ala Ala Val Thr Ala Gly Val
1 5 10 15

Ala

<210> SEQ ID NO 129
<211> LENGTH: 15
<212> TYPE: PRT
<213> ORGANISM: Human respiratory syncytial virus

<400> SEQUENCE: 129

Thr Asn Glu Ala Val Val Ser Leu Thr Asn Gly Met Ser Val Leu
1 5 10 15

<210> SEQ ID NO 130
<211> LENGTH: 13
<212> TYPE: PRT
<213> ORGANISM: Human respiratory syncytial virus

<400> SEQUENCE: 130

Val Ile Arg Phe Gln Gln Leu Asn Lys Arg Leu Leu Glu
1 5 10

<210> SEQ ID NO 131
<211> LENGTH: 10
<212> TYPE: PRT
<213> ORGANISM: Human respiratory syncytial virus

<400> SEQUENCE: 131

Arg Glu Phe Ser Ser Asn Ala Gly Leu Thr
1 5 10

<210> SEQ ID NO 132
<211> LENGTH: 14
<212> TYPE: PRT
<213> ORGANISM: Human respiratory syncytial virus

<400> SEQUENCE: 132

Met Leu Thr Asp Arg Glu Leu Thr Ser Ile Val Gly Gly Met
1 5 10

<210> SEQ ID NO 133
<211> LENGTH: 16
<212> TYPE: PRT
<213> ORGANISM: Human respiratory syncytial virus

<400> SEQUENCE: 133

```
Tyr Val Ile Gln Leu Pro Leu Phe Gly Val Met Asp Thr Asp Cys Trp
1               5                   10                  15


<210> SEQ ID NO 134
<211> LENGTH: 21
<212> TYPE: PRT
<213> ORGANISM: Human respiratory syncytial virus

<400> SEQUENCE: 134

Cys Leu Ala Arg Ala Asp Asn Gly Trp Tyr Cys His Asn Ala Gly Ser
1               5                   10                  15

Leu Ser Tyr Phe Pro
            20


<210> SEQ ID NO 135
<211> LENGTH: 16
<212> TYPE: PRT
<213> ORGANISM: Human respiratory syncytial virus

<400> SEQUENCE: 135

Asp Thr Leu Lys Ser Leu Thr Val Pro Val Thr Ser Arg Glu Cys Asn
1               5                   10                  15


<210> SEQ ID NO 136
<211> LENGTH: 21
<212> TYPE: PRT
<213> ORGANISM: Human respiratory syncytial virus

<400> SEQUENCE: 136

Tyr Asp Cys Lys Ile Ser Thr Ser Lys Thr Tyr Val Ser Thr Ala Val
1               5                   10                  15

Leu Thr Thr Met Gly
            20


<210> SEQ ID NO 137
<211> LENGTH: 13
<212> TYPE: PRT
<213> ORGANISM: Human respiratory syncytial virus

<400> SEQUENCE: 137

Val Ser Cys Tyr Gly His Asn Ser Cys Thr Val Ile Asn
1               5                   10


<210> SEQ ID NO 138
<211> LENGTH: 22
<212> TYPE: PRT
<213> ORGANISM: Rabies virus

<400> SEQUENCE: 138

Glu Ser Leu Val Ile Ile Ser Pro Ser Val Ala Asp Leu Asp Pro Tyr
1               5                   10                  15

Asp Arg Ser Leu His Ser
            20


<210> SEQ ID NO 139
<211> LENGTH: 34
<212> TYPE: PRT
<213> ORGANISM: Human respiratory syncytial virus

<400> SEQUENCE: 139

Pro Leu Ser Phe Pro Asp Asp Lys Phe Asp Val Ala Ile Arg Asp Val
1               5                   10                  15

Glu His Ser Ile Asn Gln Thr Arg Thr Phe Leu Lys Ala Ser Asp Gln
```

20 25 30

Leu Leu

<210> SEQ ID NO 140
<211> LENGTH: 25
<212> TYPE: PRT
<213> ORGANISM: Human respiratory syncytial virus

<400> SEQUENCE: 140

Lys Ile Met Thr Ser Lys Thr Asp Ile Ser Ser Ser Val Ile Thr Ser
1 5 10 15

Ile Gly Ala Ile Val Ser Cys Tyr Gly
20 25

<210> SEQ ID NO 141
<211> LENGTH: 18
<212> TYPE: PRT
<213> ORGANISM: Coronavirinae

<400> SEQUENCE: 141

Arg Ser Ala Ile Glu Asp Leu Leu Phe Asp Lys Val Lys Leu Ser Asp
1 5 10 15

Val Gly

<210> SEQ ID NO 142
<211> LENGTH: 17
<212> TYPE: PRT
<213> ORGANISM: Coronavirinae

<400> SEQUENCE: 142

Val Pro Phe Tyr Leu Asn Val Gln Tyr Arg Ile Asn Gly Leu Gly Val
1 5 10 15

Thr

<210> SEQ ID NO 143
<211> LENGTH: 21
<212> TYPE: PRT
<213> ORGANISM: Coronavirinae

<400> SEQUENCE: 143

Val Leu Ser Gln Asn Gln Lys Leu Ile Ala Asn Ala Phe Asn Asn Ala
1 5 10 15

Leu His Ala Ile Gln
20

<210> SEQ ID NO 144
<211> LENGTH: 16
<212> TYPE: PRT
<213> ORGANISM: Coronavirinae

<400> SEQUENCE: 144

Thr Asn Ser Ala Leu Val Lys Ile Gln Ala Val Val Asn Ala Asn Ala
1 5 10 15

<210> SEQ ID NO 145
<211> LENGTH: 24
<212> TYPE: PRT
<213> ORGANISM: Coronavirinae

<400> SEQUENCE: 145

Ala Glu Ala Gln Ile Asp Arg Leu Ile Asn Gly Arg Leu Thr Ala Leu
1 5 10 15

Asn Ala Tyr Val Ser Gln Gln Leu
20

<210> SEQ ID NO 146
<211> LENGTH: 31
<212> TYPE: PRT
<213> ORGANISM: Coronavirinae

<400> SEQUENCE: 146

Ser Ala Ala Gln Ala Met Glu Lys Val Asn Glu Cys Val Lys Ser Gln
1 5 10 15

Ser Ser Arg Ile Asn Phe Cys Gly Asn Gly Asn His Ile Ile Ser
20 25 30

<210> SEQ ID NO 147
<211> LENGTH: 14
<212> TYPE: PRT
<213> ORGANISM: Coronavirinae

<400> SEQUENCE: 147

Ala Pro Tyr Gly Leu Tyr Phe Ile His Phe Asn Tyr Val Pro
1 5 10

<210> SEQ ID NO 148
<211> LENGTH: 32
<212> TYPE: PRT
<213> ORGANISM: Coronavirinae

<400> SEQUENCE: 148

Leu Gln Glu Ala Ile Lys Val Leu Asn His Ser Tyr Ile Asn Leu Lys
1 5 10 15

Asp Ile Gly Thr Tyr Glu Tyr Tyr Val Lys Trp Pro Trp Tyr Val Trp
20 25 30

<210> SEQ ID NO 149
<211> LENGTH: 23
<212> TYPE: PRT
<213> ORGANISM: Arena-virus

<400> SEQUENCE: 149

Asn Ala Leu Ile Asn Asp Gln Leu Ile Met Lys Asn His Leu Arg Asp
1 5 10 15

Ile Met Gly Ile Pro Tyr Cys
20

<210> SEQ ID NO 150
<211> LENGTH: 20
<212> TYPE: PRT
<213> ORGANISM: Arena-virus

<400> SEQUENCE: 150

Phe Thr Trp Thr Leu Ser Asp Ser Glu Gly Lys Asp Thr Pro Gly Gly
1 5 10 15

Tyr Cys Leu Thr
20

<210> SEQ ID NO 151
<211> LENGTH: 29
<212> TYPE: PRT
<213> ORGANISM: Arena-virus

<400> SEQUENCE: 151

Lys Cys Phe Gly Asn Thr Ala Ile Ala Lys Cys Asn Gln Lys His Asp
1               5                   10                  15

Glu Glu Phe Cys Asp Met Leu Arg Leu Phe Asp Phe Asn
            20                  25

<210> SEQ ID NO 152
<211> LENGTH: 24
<212> TYPE: PRT
<213> ORGANISM: Arena-virus

<400> SEQUENCE: 152

Met Leu Gln Lys Glu Tyr Met Glu Arg Gln Gly Lys Thr Pro Leu Gly
1               5                   10                  15

Leu Val Asp Leu Phe Val Phe Ser
            20

<210> SEQ ID NO 153
<211> LENGTH: 16
<212> TYPE: PRT
<213> ORGANISM: Hepatitis B virus

<400> SEQUENCE: 153

Phe Asn Pro Leu Gly Phe Phe Pro Ser His Gln Leu Asp Pro Leu Phe
1               5                   10                  15

<210> SEQ ID NO 154
<211> LENGTH: 13
<212> TYPE: PRT
<213> ORGANISM: Hepatitis B virus

<400> SEQUENCE: 154

Ala Asp Trp Asp Lys Asn Pro Asn Lys Asp Pro Trp Pro
1               5                   10

<210> SEQ ID NO 155
<211> LENGTH: 20
<212> TYPE: PRT
<213> ORGANISM: Hepatitis B virus

<400> SEQUENCE: 155

Met Glu Ser Ile Thr Ser Gly Phe Leu Gly Pro Leu Leu Val Leu Gln
1               5                   10                  15

Ala Val Phe Phe
            20

<210> SEQ ID NO 156
<211> LENGTH: 25
<212> TYPE: PRT
<213> ORGANISM: Hepatitis B virus

<400> SEQUENCE: 156

Leu Leu Thr Arg Ile Leu Thr Ile Pro Gln Ser Leu Asp Ser Trp Trp
1               5                   10                  15

Thr Ser Leu Asn Phe Leu Gly Gly Ala
            20                  25

<210> SEQ ID NO 157
<211> LENGTH: 12
<212> TYPE: PRT
<213> ORGANISM: Hepatitis B virus

<400> SEQUENCE: 157

Cys Pro Pro Thr Cys Pro Gly Tyr Arg Trp Met Cys

-continued 1 5 10

<210> SEQ ID NO 158
<211> LENGTH: 18
<212> TYPE: PRT
<213> ORGANISM: Hepatitis B virus

<400> SEQUENCE: 158

Leu Phe Ile Leu Leu Leu Cys Leu Ile Phe Leu Leu Val Leu Leu Asp
1 5 10 15

Tyr Gln

<210> SEQ ID NO 159
<211> LENGTH: 15
<212> TYPE: PRT
<213> ORGANISM: Rubella virus

<400> SEQUENCE: 159

Glu Thr Arg Thr Val Trp Gln Leu Ser Val Ala Gly Val Ser Cys
1 5 10 15

<210> SEQ ID NO 160
<211> LENGTH: 24
<212> TYPE: PRT
<213> ORGANISM: Bovine ephemeral fever virus

<400> SEQUENCE: 160

Leu Asp Gly Tyr Leu Cys Arg Lys Gln Lys Trp Glu Val Thr Cys Thr
1 5 10 15

Glu Thr Trp Tyr Phe Val Thr Asp
20

<210> SEQ ID NO 161
<211> LENGTH: 14
<212> TYPE: PRT
<213> ORGANISM: Bovine ephemeral fever virus

<400> SEQUENCE: 161

Lys Tyr Gln Ile Ile Glu Val Ile Pro Thr Glu Asn Glu Cys
1 5 10

<210> SEQ ID NO 162
<211> LENGTH: 24
<212> TYPE: PRT
<213> ORGANISM: Bovine ephemeral fever virus

<400> SEQUENCE: 162

Leu Lys Gly Glu Tyr Ile Pro Pro Tyr Tyr Pro Pro Thr Asn Cys Val
1 5 10 15

Trp Asn Ala Ile Asp Thr Gln Glu
20

<210> SEQ ID NO 163
<211> LENGTH: 18
<212> TYPE: PRT
<213> ORGANISM: Bovine ephemeral fever virus

<400> SEQUENCE: 163

Ile Glu Asp Pro Val Thr Met Thr Leu Met Asp Ser Lys Phe Thr Lys
1 5 10 15

Pro Cys

<210> SEQ ID NO 164
<211> LENGTH: 13
<212> TYPE: PRT
<213> ORGANISM: Bovine ephemeral fever virus

<400> SEQUENCE: 164

Leu His Cys Gln Ile Lys Ser Trp Glu Cys Ile Pro Val
1 5 10

<210> SEQ ID NO 165
<211> LENGTH: 15
<212> TYPE: PRT
<213> ORGANISM: Bovine ephemeral fever virus

<400> SEQUENCE: 165

Ser His Arg Asn Met Met Glu Ala Leu Tyr Leu Glu Ser Pro Asp
1 5 10 15

<210> SEQ ID NO 166
<211> LENGTH: 20
<212> TYPE: PRT
<213> ORGANISM: Bovine ephemeral fever virus

<400> SEQUENCE: 166

Leu Thr Phe Cys Gly Tyr Asn Gly Ile Leu Leu Asp Asn Gly Glu Trp
1 5 10 15

Trp Ser Ile Tyr
20

<210> SEQ ID NO 167
<211> LENGTH: 18
<212> TYPE: PRT
<213> ORGANISM: Bovine ephemeral fever virus

<400> SEQUENCE: 167

Glu Leu Glu His Glu Lys Cys Leu Gly Thr Leu Glu Lys Leu Gln Asn
1 5 10 15

Gly Glu

<210> SEQ ID NO 168
<211> LENGTH: 17
<212> TYPE: PRT
<213> ORGANISM: Bovine ephemeral fever virus

<400> SEQUENCE: 168

Leu Asp Leu Ser Tyr Leu Ser Pro Ser Asn Pro Gly Lys His Tyr Ala
1 5 10 15

Tyr

<210> SEQ ID NO 169
<211> LENGTH: 15
<212> TYPE: PRT
<213> ORGANISM: Bovine ephemeral fever virus

<400> SEQUENCE: 169

Ile Arg Ala Val Cys Tyr Tyr His Thr Phe Ser Met Asn Leu Asp
1 5 10 15

<210> SEQ ID NO 170
<211> LENGTH: 20
<212> TYPE: PRT
<213> ORGANISM: Vesiculovirus

<400> SEQUENCE: 170

```
Glu Trp Lys Thr Thr Cys Asp Tyr Arg Trp Tyr Gly Pro Gln Tyr Ile
1               5                   10                  15

Thr His Ser Ile
            20


<210> SEQ ID NO 171
<211> LENGTH: 15
<212> TYPE: PRT
<213> ORGANISM: Vesiculovirus

<400> SEQUENCE: 171

Leu Gly Phe Pro Pro Gln Ser Cys Gly Trp Ala Ser Val Thr Thr
1               5                   10                  15


<210> SEQ ID NO 172
<211> LENGTH: 23
<212> TYPE: PRT
<213> ORGANISM: Dengue

<400> SEQUENCE: 172

Lys Gly Ser Ser Ile Gly Lys Met Phe Glu Ser Thr Tyr Arg Gly Ala
1               5                   10                  15

Lys Arg Met Ala Ile Leu Gly
            20


<210> SEQ ID NO 173
<211> LENGTH: 23
<212> TYPE: PRT
<213> ORGANISM: Dengue

<400> SEQUENCE: 173

Lys Gly Ser Ser Ile Gly Lys Met Phe Glu Ala Thr Ala Arg Gly Ala
1               5                   10                  15

Arg Arg Met Ala Ile Leu Gly
            20


<210> SEQ ID NO 174
<211> LENGTH: 23
<212> TYPE: PRT
<213> ORGANISM: Dengue

<400> SEQUENCE: 174

Lys Gly Ser Ser Ile Gly Gln Met Phe Glu Thr Thr Met Arg Gly Ala
1               5                   10                  15

Lys Arg Met Ala Ile Leu Gly
            20


<210> SEQ ID NO 175
<211> LENGTH: 18
<212> TYPE: PRT
<213> ORGANISM: Hepatitis C virus

<400> SEQUENCE: 175

Pro Ala Leu Ser Thr Gly Leu Ile His Leu His Gln Asn Ile Val Asp
1               5                   10                  15

Val Gln


<210> SEQ ID NO 176
<211> LENGTH: 18
<212> TYPE: PRT
<213> ORGANISM: Hepatitis C virus
```

<400> SEQUENCE: 176

Pro Ala Leu Ser Thr Gly Leu Ile His Leu His Arg Asn Ile Val Asp
1 5 10 15

Val Gln

<210> SEQ ID NO 177
<211> LENGTH: 18
<212> TYPE: PRT
<213> ORGANISM: Hepatitis C virus

<400> SEQUENCE: 177

Pro Ala Leu Ser Thr Gly Leu Ile His Leu His Gln Asn Ile Val Asp
1 5 10 15

Thr Gln

<210> SEQ ID NO 178
<211> LENGTH: 18
<212> TYPE: PRT
<213> ORGANISM: Influenza A virus

<400> SEQUENCE: 178

Trp Thr Tyr Asn Ala Glu Leu Leu Val Leu Leu Glu Asn Glu Arg Thr
1 5 10 15

Leu Asp

<210> SEQ ID NO 179
<211> LENGTH: 18
<212> TYPE: PRT
<213> ORGANISM: Influenza A virus

<400> SEQUENCE: 179

Asn Ala Glu Leu Leu Val Leu Leu Glu Asn Glu Arg Thr Leu Asp Tyr
1 5 10 15

His Asp

<210> SEQ ID NO 180
<211> LENGTH: 18
<212> TYPE: PRT
<213> ORGANISM: Influenza A virus

<400> SEQUENCE: 180

Trp Thr Tyr Asn Ala Glu Leu Leu Val Leu Met Glu Asn Glu Arg Thr
1 5 10 15

Leu Asp

<210> SEQ ID NO 181
<211> LENGTH: 18
<212> TYPE: PRT
<213> ORGANISM: Influenza A virus

<400> SEQUENCE: 181

Asn Ala Glu Leu Leu Val Leu Met Glu Asn Glu Arg Thr Leu Asp Tyr
1 5 10 15

His Asp

<210> SEQ ID NO 182
<211> LENGTH: 18
<212> TYPE: PRT
<213> ORGANISM: Influenza A virus

<400> SEQUENCE: 182

```
Trp Ser Tyr Asn Ala Glu Leu Leu Val Ala Leu Glu Asn Gln His Thr
1               5                   10                  15

Ile Asp


<210> SEQ ID NO 183
<211> LENGTH: 18
<212> TYPE: PRT
<213> ORGANISM: Influenza A virus

<400> SEQUENCE: 183

Asn Ala Glu Leu Leu Val Ala Leu Glu Asn Gln His Thr Ile Asp Leu
1               5                   10                  15

Thr Asp


<210> SEQ ID NO 184
<211> LENGTH: 18
<212> TYPE: PRT
<213> ORGANISM: Influenza A virus

<400> SEQUENCE: 184

Asn Ala Glu Leu Leu Val Ala Leu Glu Asn Gln His Thr Ile Asp Val
1               5                   10                  15

Thr Asp


<210> SEQ ID NO 185
<211> LENGTH: 18
<212> TYPE: PRT
<213> ORGANISM: Influenza A virus

<400> SEQUENCE: 185

Asn Ala Glu Leu Leu Val Leu Met Glu Asn Glu Arg Thr Leu Asp Phe
1               5                   10                  15

His Asp


<210> SEQ ID NO 186
<211> LENGTH: 18
<212> TYPE: PRT
<213> ORGANISM: Influenza A virus

<400> SEQUENCE: 186

Asn Ala Glu Leu Leu Val Leu Leu Glu Asn Glu Arg Thr Leu Asp Met
1               5                   10                  15

His Asp


<210> SEQ ID NO 187
<211> LENGTH: 18
<212> TYPE: PRT
<213> ORGANISM: Influenza A virus

<400> SEQUENCE: 187

Trp Ser Tyr Asn Ala Glu Leu Leu Val Ala Met Glu Asn Gln His Thr
1               5                   10                  15

Ile Asp


<210> SEQ ID NO 188
<211> LENGTH: 18
<212> TYPE: PRT
<213> ORGANISM: Influenza A virus

<400> SEQUENCE: 188
```

Asn Ala Glu Leu Leu Val Ala Met Glu Asn Gln His Thr Ile Asp Leu
1 5 10 15

Ala Asp

<210> SEQ ID NO 189
<211> LENGTH: 18
<212> TYPE: PRT
<213> ORGANISM: Influenza A virus

<400> SEQUENCE: 189

Trp Ala Tyr Asn Ala Glu Leu Leu Val Leu Leu Glu Asn Gln Lys Thr
1 5 10 15

Leu Asp

<210> SEQ ID NO 190
<211> LENGTH: 18
<212> TYPE: PRT
<213> ORGANISM: Influenza A virus

<400> SEQUENCE: 190

Asn Ala Glu Leu Leu Val Leu Leu Glu Asn Gln Lys Thr Leu Asp Glu
1 5 10 15

His Asp

<210> SEQ ID NO 191
<211> LENGTH: 18
<212> TYPE: PRT
<213> ORGANISM: Influenza A virus

<400> SEQUENCE: 191

Trp Thr Tyr Gln Ala Glu Leu Leu Val Ala Met Glu Asn Gln His Thr
1 5 10 15

Ile Asp

<210> SEQ ID NO 192
<211> LENGTH: 18
<212> TYPE: PRT
<213> ORGANISM: Influenza A virus

<400> SEQUENCE: 192

Gln Ala Glu Leu Leu Val Ala Met Glu Asn Gln His Thr Ile Asp Met
1 5 10 15

Ala Asp

<210> SEQ ID NO 193
<211> LENGTH: 18
<212> TYPE: PRT
<213> ORGANISM: Influenza A virus

<400> SEQUENCE: 193

Trp Ser Tyr Asn Ala Gln Leu Leu Val Leu Leu Glu Asn Glu Lys Thr
1 5 10 15

Leu Asp

<210> SEQ ID NO 194
<211> LENGTH: 18
<212> TYPE: PRT
<213> ORGANISM: Influenza A virus

<400> SEQUENCE: 194

Asn Ala Gln Leu Leu Val Leu Leu Glu Asn Glu Lys Thr Leu Asp Leu

-continued 1 5 10 15

His Asp

<210> SEQ ID NO 195
<211> LENGTH: 18
<212> TYPE: PRT
<213> ORGANISM: Influenza A virus

<400> SEQUENCE: 195

Trp Ser Tyr Asn Ala Lys Leu Leu Val Leu Leu Glu Asn Asp Lys Thr
1 5 10 15

Leu Asp

<210> SEQ ID NO 196
<211> LENGTH: 18
<212> TYPE: PRT
<213> ORGANISM: Influenza A virus

<400> SEQUENCE: 196

Asn Ala Lys Leu Leu Val Leu Leu Glu Asn Asp Lys Thr Leu Asp Met
1 5 10 15

His Asp

<210> SEQ ID NO 197
<211> LENGTH: 18
<212> TYPE: PRT
<213> ORGANISM: Influenza A virus

<400> SEQUENCE: 197

Trp Ser Tyr Asn Ala Lys Leu Leu Val Leu Ile Glu Asn Asp Arg Thr
1 5 10 15

Leu Asp

<210> SEQ ID NO 198
<211> LENGTH: 18
<212> TYPE: PRT
<213> ORGANISM: Influenza A virus

<400> SEQUENCE: 198

Asn Ala Lys Leu Leu Val Leu Ile Glu Asn Asp Arg Thr Leu Asp Leu
1 5 10 15

His Asp

<210> SEQ ID NO 199
<211> LENGTH: 18
<212> TYPE: PRT
<213> ORGANISM: Influenza A virus

<400> SEQUENCE: 199

Ile Ser Ser Gln Ile Glu Leu Ala Val Leu Leu Ser Asn Glu Gly Ile
1 5 10 15

Ile Asn

<210> SEQ ID NO 200
<211> LENGTH: 18
<212> TYPE: PRT
<213> ORGANISM: Influenza A virus

<400> SEQUENCE: 200

Gln Ile Glu Leu Ala Val Leu Leu Ser Asn Glu Gly Ile Ile Asn Ser
1 5 10 15

Glu Asp

<210> SEQ ID NO 201
<211> LENGTH: 15
<212> TYPE: PRT
<213> ORGANISM: Influenza virus

<400> SEQUENCE: 201

Gly Leu Phe Gly Ala Ala Gly Phe Ile Glu Asn Gly Trp Glu Gly
1 5 10 15

<210> SEQ ID NO 202
<211> LENGTH: 14
<212> TYPE: PRT
<213> ORGANISM: flavivirus

<400> SEQUENCE: 202

Asp Arg Gly Trp Gly Asn Gly Cys Gly Asp Phe Gly Lys Gly
1 5 10

<210> SEQ ID NO 203
<211> LENGTH: 18
<212> TYPE: PRT
<213> ORGANISM: Influenza virus

<400> SEQUENCE: 203

Asn Ala Glu Leu Leu Val Leu Leu Glu Asn Glu Arg Thr Leu Asp Phe
1 5 10 15

His Asp

<210> SEQ ID NO 204
<211> LENGTH: 19
<212> TYPE: PRT
<213> ORGANISM: Dengue

<400> SEQUENCE: 204

Gly Asp Thr Ala Trp Asp Phe Gly Ser Val Gly Gly Val Leu Asn Ser
1 5 10 15

Leu Gly Lys

<210> SEQ ID NO 205
<211> LENGTH: 27
<212> TYPE: PRT
<213> ORGANISM: Porcine pestivirus isolate Bungowannah

<400> SEQUENCE: 205

Thr Leu Leu Asn Gly Pro Ala Phe Gln Leu Val Cys Pro Tyr Gly Trp
1 5 10 15

Thr Gly Thr Ile Glu Cys Asp Ser Tyr Tyr Gln
20 25

<210> SEQ ID NO 206
<211> LENGTH: 16
<212> TYPE: PRT
<213> ORGANISM: Rabies virus

<400> SEQUENCE: 206

Ile Leu Gly Pro Asp Gly Asn Val Leu Ile Pro Glu Met Gln Ser Ser
1 5 10 15

<210> SEQ ID NO 207
<211> LENGTH: 14

<212> TYPE: PRT
<213> ORGANISM: Rubella virus

<400> SEQUENCE: 207

Leu Leu Asn Thr Pro Pro Pro Tyr Gln Val Ser Cys Gly Gly
1 5 10

<210> SEQ ID NO 208
<211> LENGTH: 18
<212> TYPE: PRT
<213> ORGANISM: Influenza A virus

<400> SEQUENCE: 208

Trp Ser Tyr Asn Ala Glu Leu Leu Val Ala Met Glu Asn Gln His Leu
1 5 10 15

Ala Asp

<210> SEQ ID NO 209
<211> LENGTH: 27
<212> TYPE: PRT
<213> ORGANISM: Coronavirinae

<400> SEQUENCE: 209

Glu Val Phe Ala Gln Val Lys Gln Met Tyr Lys Thr Pro Thr Leu Lys
1 5 10 15

Tyr Phe Gly Gly Phe Asn Phe Ser Gln Ile Leu
20 25

<210> SEQ ID NO 210
<211> LENGTH: 27
<212> TYPE: PRT
<213> ORGANISM: Coronavirinae

<400> SEQUENCE: 210

Glu Val Phe Ala Gln Val Lys Gln Met Tyr Lys Thr Pro Ala Ile Lys
1 5 10 15

Asp Phe Gly Gly Phe Asn Phe Ser Gln Ile Leu
20 25

<210> SEQ ID NO 211
<211> LENGTH: 18
<212> TYPE: PRT
<213> ORGANISM: Coronavirinae

<400> SEQUENCE: 211

Ser Phe Ile Glu Asp Leu Leu Phe Asn Lys Val Thr Leu Ala Asp Ala
1 5 10 15

Gly Phe

<210> SEQ ID NO 212
<211> LENGTH: 18
<212> TYPE: PRT
<213> ORGANISM: Coronavirinae

<400> SEQUENCE: 212

Ser Ala Ile Glu Asp Leu Leu Phe Asn Lys Val Arg Leu Ser Asp Val
1 5 10 15

Gly Phe

<210> SEQ ID NO 213
<211> LENGTH: 18
<212> TYPE: PRT

<213> ORGANISM: Coronavirinae

<400> SEQUENCE: 213

Ser Leu Leu Glu Asp Leu Leu Phe Asn Lys Val Lys Leu Ser Asp Val
1 5 10 15

Gly Phe

<210> SEQ ID NO 214
<211> LENGTH: 18
<212> TYPE: PRT
<213> ORGANISM: Coronavirinae

<400> SEQUENCE: 214

Ser Ala Ile Glu Asp Leu Leu Phe Ser Lys Val Lys Leu Ala Asp Val
1 5 10 15

Gly Phe

<210> SEQ ID NO 215
<211> LENGTH: 18
<212> TYPE: PRT
<213> ORGANISM: Coronavirinae

<400> SEQUENCE: 215

Ser Ala Ile Glu Asp Leu Leu Phe Asp Lys Val Lys Leu Ser Asp Val
1 5 10 15

Gly Phe

<210> SEQ ID NO 216
<211> LENGTH: 17
<212> TYPE: PRT
<213> ORGANISM: Filoviridae

<400> SEQUENCE: 216

Gly Ala Ala Ile Gly Leu Ala Trp Ile Pro Tyr Phe Gly Pro Ala Ala
1 5 10 15

Glu

<210> SEQ ID NO 217
<211> LENGTH: 17
<212> TYPE: PRT
<213> ORGANISM: Filoviridae

<400> SEQUENCE: 217

Gly Ala Ala Val Gly Leu Ala Trp Ile Pro Tyr Phe Gly Pro Ala Ala
1 5 10 15

Glu

<210> SEQ ID NO 218
<211> LENGTH: 17
<212> TYPE: PRT
<213> ORGANISM: Filoviridae

<400> SEQUENCE: 218

Gly Ala Ala Ala Gly Leu Ala Trp Ile Pro Tyr Phe Gly Pro Ala Ala
1 5 10 15

Glu

<210> SEQ ID NO 219
<211> LENGTH: 17
<212> TYPE: PRT
<213> ORGANISM: Filoviridae

<400> SEQUENCE: 219

Asp Leu Ala Ala Gly Leu Ser Trp Ile Pro Phe Phe Gly Pro Gly Ile
1               5                   10                  15

Glu

<210> SEQ ID NO 220
<211> LENGTH: 17
<212> TYPE: PRT
<213> ORGANISM: Filoviridae

<400> SEQUENCE: 220

His Asn Ala Ala Gly Ile Ala Trp Ile Pro Tyr Phe Gly Pro Gly Ala
1               5                   10                  15

Glu

<210> SEQ ID NO 221
<211> LENGTH: 23
<212> TYPE: PRT
<213> ORGANISM: Hiv1

<400> SEQUENCE: 221

Ala Val Gly Leu Gly Ala Leu Phe Leu Gly Phe Leu Gly Ala Ala Gly
1               5                   10                  15

Ser Thr Met Gly Ala Ala Ser
            20

<210> SEQ ID NO 222
<211> LENGTH: 12
<212> TYPE: PRT
<213> ORGANISM: Hiv1

<400> SEQUENCE: 222

Leu Thr Leu Thr Gly Gln Ala Arg Gln Leu Leu Ser
1               5                   10

<210> SEQ ID NO 223
<211> LENGTH: 17
<212> TYPE: PRT
<213> ORGANISM: Hiv1

<400> SEQUENCE: 223

Gly Ile Val Gln Gln Gln Ser Asn Leu Leu Gln Ala Ile Glu Ala Gln
1               5                   10                  15

Gln

<210> SEQ ID NO 224
<211> LENGTH: 33
<212> TYPE: PRT
<213> ORGANISM: Hiv1

<400> SEQUENCE: 224

Gly Leu Gly Ala Met Phe Leu Gly Phe Leu Gly Ala Ala Gly Ser Thr
1               5                   10                  15

Met Gly Ala Ala Ser Leu Thr Leu Thr Val Gln Ala Arg Gln Leu Leu
            20                  25                  30

Ser

<210> SEQ ID NO 225
<211> LENGTH: 33
<212> TYPE: PRT

<213> ORGANISM: Hiv1

<400> SEQUENCE: 225

Gly Ile Gly Ala Met Phe Leu Gly Leu Leu Ser Ala Ala Gly Ser Thr
1 5 10 15

Met Ser Ala Ala Ala Ile Thr Leu Thr Val Gln Thr Arg Gln Leu Leu
20 25 30

Ser

<210> SEQ ID NO 226
<211> LENGTH: 33
<212> TYPE: PRT
<213> ORGANISM: Hiv1

<400> SEQUENCE: 226

Gly Ile Gly Ala Met Phe Leu Gly Leu Leu Ser Ala Ala Gly Ser Thr
1 5 10 15

Met Gly Ala Ala Ala Ile Thr Leu Thr Val Gln Thr Arg Gln Leu Leu
20 25 30

Ser

<210> SEQ ID NO 227
<211> LENGTH: 33
<212> TYPE: PRT
<213> ORGANISM: Hiv1

<400> SEQUENCE: 227

Gly Ile Gly Ala Val Phe Leu Gly Phe Leu Gly Ala Ala Gly Ser Thr
1 5 10 15

Met Gly Ala Ala Ser Ile Thr Leu Thr Val Gln Ala Arg Gln Leu Leu
20 25 30

Ser

<210> SEQ ID NO 228
<211> LENGTH: 33
<212> TYPE: PRT
<213> ORGANISM: Hiv1

<400> SEQUENCE: 228

Gly Val Gly Ala Leu Phe Leu Gly Phe Leu Ser Ala Ala Gly Ser Thr
1 5 10 15

Met Gly Ala Ala Ser Ile Thr Leu Thr Val Gln Ala Arg Gln Leu Leu
20 25 30

Ser

<210> SEQ ID NO 229
<211> LENGTH: 33
<212> TYPE: PRT
<213> ORGANISM: Hiv1

<400> SEQUENCE: 229

Gly Ile Gly Ala Met Ile Leu Gly Phe Leu Gly Ala Ala Gly Ser Thr
1 5 10 15

Met Gly Ala Ala Ser Ile Thr Leu Thr Val Gln Ala Arg Gln Leu Leu
20 25 30

Ser

<210> SEQ ID NO 230
<211> LENGTH: 33

<212> TYPE: PRT
<213> ORGANISM: Hiv1

<400> SEQUENCE: 230

```
Gly Leu Gly Ala Met Phe Leu Gly Phe Leu Gly Ala Ala Gly Ser Thr
1               5                   10                  15

Met Gly Ala Ala Ser Ile Thr Leu Thr Val Gln Ala Arg Gln Leu Leu
            20                  25                  30

Ser
```

<210> SEQ ID NO 231
<211> LENGTH: 33
<212> TYPE: PRT
<213> ORGANISM: Hiv1

<400> SEQUENCE: 231

```
Gly Phe Gly Ala Met Phe Leu Gly Phe Leu Gly Ala Ala Gly Ser Thr
1               5                   10                  15

Met Gly Ala Ala Ser Ile Thr Leu Thr Val Gln Ala Arg Gln Leu Leu
            20                  25                  30

Ser
```

<210> SEQ ID NO 232
<211> LENGTH: 33
<212> TYPE: PRT
<213> ORGANISM: Hiv1

<400> SEQUENCE: 232

```
Thr Leu Gly Ala Met Phe Leu Gly Phe Leu Gly Ala Ala Gly Ser Thr
1               5                   10                  15

Met Gly Ala Ala Ser Met Thr Leu Thr Val Gln Ala Arg Gln Leu Leu
            20                  25                  30

Ser
```

<210> SEQ ID NO 233
<211> LENGTH: 33
<212> TYPE: PRT
<213> ORGANISM: Hiv1

<400> SEQUENCE: 233

```
Gly Leu Gly Ala Val Phe Leu Gly Phe Leu Gly Ala Ala Gly Ser Thr
1               5                   10                  15

Met Gly Ala Ala Ser Ile Thr Leu Thr Val Gln Ala Arg Gln Leu Leu
            20                  25                  30

Ser
```

<210> SEQ ID NO 234
<211> LENGTH: 33
<212> TYPE: PRT
<213> ORGANISM: Hiv1

<400> SEQUENCE: 234

```
Thr Ile Gly Ala Met Phe Leu Gly Phe Leu Gly Ala Ala Gly Ser Thr
1               5                   10                  15

Met Gly Ala Ala Ser Ile Thr Leu Thr Val Gln Ala Arg Arg Leu Leu
            20                  25                  30

Ser
```

<210> SEQ ID NO 235

<211> LENGTH: 33
<212> TYPE: PRT
<213> ORGANISM: Hiv1

<400> SEQUENCE: 235

Thr Ile Gly Ala Met Phe Leu Gly Phe Leu Gly Ala Ala Gly Ser Thr
1 5 10 15

Met Gly Ala Ala Ser Met Thr Leu Thr Val Gln Ala Arg Leu Leu Leu
20 25 30

Ser

<210> SEQ ID NO 236
<211> LENGTH: 33
<212> TYPE: PRT
<213> ORGANISM: Hiv1

<400> SEQUENCE: 236

Thr Leu Gly Ala Met Phe Leu Gly Phe Leu Gly Ala Ala Gly Ser Thr
1 5 10 15

Met Gly Ala Ala Ser Met Thr Leu Thr Val Gln Ala Arg Leu Leu Phe
20 25 30

Ser

<210> SEQ ID NO 237
<211> LENGTH: 33
<212> TYPE: PRT
<213> ORGANISM: Hiv1

<400> SEQUENCE: 237

Thr Leu Gly Ala Met Phe Leu Gly Phe Leu Gly Ala Ala Gly Ser Thr
1 5 10 15

Met Gly Ala Ala Ser Leu Thr Leu Thr Val Gln Ala Arg Leu Leu Leu
20 25 30

Ser

<210> SEQ ID NO 238
<211> LENGTH: 33
<212> TYPE: PRT
<213> ORGANISM: Hiv1

<400> SEQUENCE: 238

Gly Val Gly Ala Met Phe Leu Gly Phe Leu Gly Ala Ala Gly Ser Thr
1 5 10 15

Met Gly Ala Ala Ser Leu Thr Leu Thr Val Gln Ala Arg Gln Leu Leu
20 25 30

Ser

<210> SEQ ID NO 239
<211> LENGTH: 33
<212> TYPE: PRT
<213> ORGANISM: Hiv1

<400> SEQUENCE: 239

Gly Leu Gly Ala Met Phe Leu Gly Phe Leu Gly Ala Ala Gly Ser Thr
1 5 10 15

Met Gly Ala Ala Ser Ile Thr Leu Thr Val Gln Ala Arg Leu Leu Leu
20 25 30

Ser

<210> SEQ ID NO 240
<211> LENGTH: 33
<212> TYPE: PRT
<213> ORGANISM: Hiv1

<400> SEQUENCE: 240

Thr Leu Gly Ala Val Phe Leu Gly Phe Leu Gly Ala Ala Gly Ser Thr
1               5                   10                  15

Met Gly Ala Ala Ser Leu Thr Leu Thr Val Gln Ala Arg Leu Leu Leu
            20                  25                  30

Ser

<210> SEQ ID NO 241
<211> LENGTH: 33
<212> TYPE: PRT
<213> ORGANISM: Hiv1

<400> SEQUENCE: 241

Gly Ile Gly Ala Val Phe Leu Gly Phe Leu Gly Ala Ala Gly Ser Thr
1               5                   10                  15

Met Gly Ala Ala Ser Ile Thr Leu Thr Val Gln Ala Arg Lys Leu Leu
            20                  25                  30

Ser

<210> SEQ ID NO 242
<211> LENGTH: 33
<212> TYPE: PRT
<213> ORGANISM: Hiv1

<400> SEQUENCE: 242

Gly Ile Gly Ala Leu Phe Leu Gly Phe Leu Gly Ala Ala Gly Ser Thr
1               5                   10                  15

Met Gly Ala Ala Ser Val Thr Leu Thr Val Gln Ala Arg Gln Leu Leu
            20                  25                  30

Ser

<210> SEQ ID NO 243
<211> LENGTH: 33
<212> TYPE: PRT
<213> ORGANISM: Hiv1

<400> SEQUENCE: 243

Gly Leu Gly Ala Leu Phe Leu Gly Phe Leu Gly Ala Ala Gly Ser Thr
1               5                   10                  15

Met Gly Ala Ala Ser Val Thr Leu Thr Val Gln Ala Arg Gln Leu Leu
            20                  25                  30

Ser

<210> SEQ ID NO 244
<211> LENGTH: 33
<212> TYPE: PRT
<213> ORGANISM: Hiv1

<400> SEQUENCE: 244

Gly Ile Gly Ala Met Phe Leu Gly Phe Leu Gly Ala Ala Gly Ser Thr
1               5                   10                  15

Met Gly Ala Ala Ser Ile Thr Leu Thr Val Gln Ala Arg Leu Leu Leu
            20                  25                  30

Ser

<210> SEQ ID NO 245
<211> LENGTH: 33
<212> TYPE: PRT
<213> ORGANISM: Hiv1

<400> SEQUENCE: 245

Gly Ile Gly Ala Met Phe Leu Gly Phe Leu Gly Ala Ala Gly Ser Thr
1 5 10 15

Met Gly Ala Ala Ser Val Thr Leu Thr Val Gln Ala Arg Leu Leu Leu
20 25 30

Ser

<210> SEQ ID NO 246
<211> LENGTH: 33
<212> TYPE: PRT
<213> ORGANISM: Hiv1

<400> SEQUENCE: 246

Ala Ile Gly Ala Leu Phe Leu Gly Phe Leu Gly Ala Ala Gly Ser Thr
1 5 10 15

Met Gly Ala Ala Ser Val Thr Leu Thr Val Gln Ala Arg Leu Leu Leu
20 25 30

Ser

<210> SEQ ID NO 247
<211> LENGTH: 33
<212> TYPE: PRT
<213> ORGANISM: Hiv1

<400> SEQUENCE: 247

Thr Leu Gly Ala Met Phe Leu Gly Phe Leu Gly Ala Ala Gly Ser Thr
1 5 10 15

Met Gly Ala Ala Ser Leu Thr Leu Thr Val Gln Ala Arg Gln Leu Leu
20 25 30

Ser

<210> SEQ ID NO 248
<211> LENGTH: 33
<212> TYPE: PRT
<213> ORGANISM: Hiv1

<400> SEQUENCE: 248

Gly Ile Gly Ala Leu Phe Leu Gly Phe Leu Gly Ala Ala Gly Ser Thr
1 5 10 15

Met Gly Ala Ala Ser Met Thr Leu Thr Val Gln Ala Arg Gln Leu Leu
20 25 30

Ser

<210> SEQ ID NO 249
<211> LENGTH: 33
<212> TYPE: PRT
<213> ORGANISM: Hiv1

<400> SEQUENCE: 249

Gly Ile Gly Ala Met Phe Leu Gly Phe Leu Gly Ala Ala Gly Ser Thr
1 5 10 15

Met Gly Ala Ala Ser Leu Thr Leu Thr Val Gln Ala Arg Gln Leu Leu
20 25 30

Ser

<210> SEQ ID NO 250
<211> LENGTH: 33
<212> TYPE: PRT
<213> ORGANISM: Hiv1

<400> SEQUENCE: 250

Gly Ile Gly Ala Val Phe Leu Gly Phe Leu Gly Ala Ala Gly Ser Thr
1 5 10 15

Met Gly Ala Ala Ser Met Thr Leu Thr Val Gln Ala Arg Leu Leu Leu
20 25 30

Ser

<210> SEQ ID NO 251
<211> LENGTH: 33
<212> TYPE: PRT
<213> ORGANISM: Hiv1

<400> SEQUENCE: 251

Gly Ile Gly Ala Leu Phe Leu Gly Phe Leu Gly Ala Ala Gly Ser Thr
1 5 10 15

Met Gly Ala Ala Ser Leu Thr Leu Thr Val Gln Ala Arg Gln Leu Leu
20 25 30

Ser

<210> SEQ ID NO 252
<211> LENGTH: 33
<212> TYPE: PRT
<213> ORGANISM: Hiv1

<400> SEQUENCE: 252

Gly Ile Gly Ala Val Phe Leu Gly Ile Leu Gly Ala Ala Gly Ser Thr
1 5 10 15

Met Gly Ala Ala Ser Ile Thr Leu Thr Val Gln Ala Arg Gln Leu Leu
20 25 30

Ser

<210> SEQ ID NO 253
<211> LENGTH: 33
<212> TYPE: PRT
<213> ORGANISM: Hiv1

<400> SEQUENCE: 253

Gly Ile Gly Ala Val Phe Leu Gly Phe Leu Gly Ala Ala Gly Ser Thr
1 5 10 15

Met Gly Ala Ala Ser Val Thr Leu Thr Val Gln Ala Arg Gln Leu Leu
20 25 30

Phe

<210> SEQ ID NO 254
<211> LENGTH: 33
<212> TYPE: PRT
<213> ORGANISM: Hiv1

<400> SEQUENCE: 254

Gly Leu Gly Ala Met Phe Phe Gly Phe Leu Gly Ala Ala Gly Ser Thr
1 5 10 15

Met Gly Ala Ala Ser Val Thr Leu Thr Val Gln Ala Arg Gln Leu Leu
20 25 30

Ser

<210> SEQ ID NO 255
<211> LENGTH: 33
<212> TYPE: PRT
<213> ORGANISM: Hiv1

<400> SEQUENCE: 255

Gly Ile Gly Ala Leu Phe Leu Gly Phe Leu Gly Ala Ala Gly Ser Thr
1 5 10 15

Met Gly Ala Ala Ser Ile Thr Leu Thr Val Gln Ala Arg Leu Leu Leu
20 25 30

Ser

<210> SEQ ID NO 256
<211> LENGTH: 33
<212> TYPE: PRT
<213> ORGANISM: Hiv1

<400> SEQUENCE: 256

Gly Leu Gly Ala Leu Phe Val Gly Phe Leu Gly Ala Ala Gly Ser Thr
1 5 10 15

Met Gly Ala Ala Ser Ile Thr Leu Thr Val Gln Ala Arg Gln Leu Leu
20 25 30

Ser

<210> SEQ ID NO 257
<211> LENGTH: 33
<212> TYPE: PRT
<213> ORGANISM: Hiv1

<400> SEQUENCE: 257

Gly Ile Gly Ala Leu Phe Leu Gly Phe Leu Gly Thr Ala Gly Ser Thr
1 5 10 15

Met Gly Ala Ala Ser Val Thr Leu Thr Val Gln Ala Arg Gln Leu Leu
20 25 30

Ser

<210> SEQ ID NO 258
<211> LENGTH: 33
<212> TYPE: PRT
<213> ORGANISM: Hiv1

<400> SEQUENCE: 258

Gly Ile Gly Ala Met Ile Phe Gly Phe Leu Gly Ala Ala Gly Ser Thr
1 5 10 15

Met Gly Ala Ala Ser Ile Thr Leu Thr Val Gln Ala Arg Gln Leu Leu
20 25 30

Ser

<210> SEQ ID NO 259
<211> LENGTH: 33
<212> TYPE: PRT
<213> ORGANISM: Hiv1

<400> SEQUENCE: 259

Gly Leu Gly Ala Val Leu Leu Gly Phe Leu Gly Thr Ala Gly Ser Thr
1 5 10 15

Met Gly Ala Ala Ser Leu Thr Leu Thr Val Gln Val Arg Gln Leu Leu
20 25 30

Ser

<210> SEQ ID NO 260
<211> LENGTH: 33
<212> TYPE: PRT
<213> ORGANISM: Hiv1

<400> SEQUENCE: 260

Gly Ile Gly Ala Val Leu Phe Gly Phe Leu Gly Ala Ala Gly Ser Thr
1 5 10 15

Met Gly Ala Ala Ser Ile Thr Leu Thr Val Gln Val Arg Gln Leu Leu
20 25 30

Ser

<210> SEQ ID NO 261
<211> LENGTH: 33
<212> TYPE: PRT
<213> ORGANISM: Hiv1

<400> SEQUENCE: 261

Gly Leu Gly Ala Leu Phe Leu Gly Phe Leu Gly Ala Ala Gly Ser Thr
1 5 10 15

Met Gly Ala Ala Ser Leu Thr Leu Thr Gly Gln Ala Arg Gln Leu Leu
20 25 30

Ser

<210> SEQ ID NO 262
<211> LENGTH: 33
<212> TYPE: PRT
<213> ORGANISM: Hiv1

<400> SEQUENCE: 262

Gly Thr Leu Gly Ala Met Phe Leu Gly Phe Leu Gly Ala Ala Gly Ser
1 5 10 15

Thr Met Gly Ala Ala Ser Met Thr Leu Thr Val Gln Ala Arg Gln Leu
20 25 30

Leu

<210> SEQ ID NO 263
<211> LENGTH: 33
<212> TYPE: PRT
<213> ORGANISM: Hiv1

<400> SEQUENCE: 263

Gly Thr Ile Gly Ala Met Phe Leu Gly Phe Leu Gly Ala Ala Gly Ser
1 5 10 15

Thr Met Gly Ala Ala Ser Ile Thr Leu Thr Val Gln Ala Arg Arg Leu
20 25 30

Leu

<210> SEQ ID NO 264
<211> LENGTH: 33
<212> TYPE: PRT
<213> ORGANISM: Hiv1

<400> SEQUENCE: 264

Gly Thr Ile Gly Ala Met Phe Leu Gly Phe Leu Gly Ala Ala Gly Ser
1 5 10 15

Thr Met Gly Ala Ala Ser Met Thr Leu Thr Val Gln Ala Arg Leu Leu 20 25 30

Leu

<210> SEQ ID NO 265
<211> LENGTH: 33
<212> TYPE: PRT
<213> ORGANISM: Hiv1

<400> SEQUENCE: 265

Ile Gly Ala Leu Phe Leu Gly Phe Leu Gly Ala Ala Gly Ser Thr Met
1 5 10 15

Gly Ala Ala Ser Val Thr Leu Thr Val Gln Ala Arg Leu Leu Leu Ser
20 25 30

Gly

<210> SEQ ID NO 266
<211> LENGTH: 23
<212> TYPE: PRT
<213> ORGANISM: Lentivirus

<400> SEQUENCE: 266

Ala Val Gly Met Val Ile Phe Leu Leu Val Leu Ala Ile Met Ala Met
1 5 10 15

Thr Ala Ser Val Thr Ala Ala
20

<210> SEQ ID NO 267
<211> LENGTH: 20
<212> TYPE: PRT
<213> ORGANISM: Lentivirus

<400> SEQUENCE: 267

Phe Gly Ile Ser Ala Ile Val Ala Ala Ile Val Ala Ala Thr Ala Ile
1 5 10 15

Ala Ala Ser Ala
20

<210> SEQ ID NO 268
<211> LENGTH: 21
<212> TYPE: PRT
<213> ORGANISM: Lentivirus

<400> SEQUENCE: 268

Thr Leu Ala Leu Val Thr Ala Thr Thr Ala Gly Leu Ile Gly Thr Thr
1 5 10 15

Thr Gly Thr Ser Ala
20

<210> SEQ ID NO 269
<211> LENGTH: 21
<212> TYPE: PRT
<213> ORGANISM: Lentivirus

<400> SEQUENCE: 269

His Val Met Leu Ala Leu Ala Thr Val Leu Ser Met Ala Gly Ala Gly
1 5 10 15

Thr Gly Ala Thr Ala
20

<210> SEQ ID NO 270
<211> LENGTH: 20

<212> TYPE: PRT
<213> ORGANISM: Lentivirus

<400> SEQUENCE: 270

Gly Ile Gly Leu Val Ile Met Leu Val Thr Met Ala Ile Val Ala Ala
1 5 10 15

Ala Gly Ala Ser
20

<210> SEQ ID NO 271
<211> LENGTH: 20
<212> TYPE: PRT
<213> ORGANISM: Lentivirus

<400> SEQUENCE: 271

Gly Val Met Val Leu Gly Phe Leu Gly Phe Leu Ala Met Ala Gly Ser
1 5 10 15

Ala Met Gly Ala
20

<210> SEQ ID NO 272
<211> LENGTH: 20
<212> TYPE: PRT
<213> ORGANISM: Lentivirus

<400> SEQUENCE: 272

Gly Val Phe Val Leu Gly Phe Leu Gly Phe Leu Ala Thr Ala Gly Ser
1 5 10 15

Ala Met Gly Ala
20

<210> SEQ ID NO 273
<211> LENGTH: 19
<212> TYPE: PRT
<213> ORGANISM: Lentivirus

<400> SEQUENCE: 273

Gly Ala Ile Val Leu Gly Leu Leu Gly Phe Leu Gly Leu Ala Gly Ser
1 5 10 15

Ala Met Gly

<210> SEQ ID NO 274
<211> LENGTH: 28
<212> TYPE: PRT
<213> ORGANISM: Lentivirus

<400> SEQUENCE: 274

Gly Ile Gly Leu Val Ile Val Leu Ala Ile Met Ala Ile Ile Ala Ala
1 5 10 15

Ala Gly Ala Gly Leu Gly Val Ala Asn Ala Val Gln
20 25

<210> SEQ ID NO 275
<211> LENGTH: 21
<212> TYPE: PRT
<213> ORGANISM: PRRS virus Type I

<400> SEQUENCE: 275

Ser Arg Lys Leu Gly Arg Ser Leu Ile Pro His Ser Cys Phe Trp Trp
1 5 10 15

Leu Phe Leu Leu Cys
20

<210> SEQ ID NO 276
<211> LENGTH: 17
<212> TYPE: PRT
<213> ORGANISM: PRRS virus Type I

<400> SEQUENCE: 276

Gly Asn Gly Asn Ser Ser Thr Tyr Gln Tyr Ile Tyr Asn Leu Thr Ile
1               5                   10                  15

Cys

<210> SEQ ID NO 277
<211> LENGTH: 24
<212> TYPE: PRT
<213> ORGANISM: PRRS virus Type I

<400> SEQUENCE: 277

Gly Thr Ala Trp Leu Ser Thr His Phe Ser Trp Ala Val Glu Thr Phe
1               5                   10                  15

Val Leu Tyr His Ile Leu Ser Leu
            20

<210> SEQ ID NO 278
<211> LENGTH: 23
<212> TYPE: PRT
<213> ORGANISM: PRRS virus Type I

<400> SEQUENCE: 278

Gly Phe Leu Thr Thr Ser His Phe Phe Asp Thr Leu Gly Leu Gly Ala
1               5                   10                  15

Val Ser Ile Thr Gly Phe Cys
            20

<210> SEQ ID NO 279
<211> LENGTH: 21
<212> TYPE: PRT
<213> ORGANISM: PRRS virus Type I

<400> SEQUENCE: 279

Arg Tyr Ala His Thr Arg Phe Thr Asn Phe Ile Val Asp Asp Arg Gly
1               5                   10                  15

Arg Ile His Arg Trp
            20

<210> SEQ ID NO 280
<211> LENGTH: 17
<212> TYPE: PRT
<213> ORGANISM: PRRS virus Type II

<400> SEQUENCE: 280

Ser Asn Asn Asn Ser Ser His Ile Gln Leu Ile Tyr Asn Leu Thr Leu
1               5                   10                  15

Cys

<210> SEQ ID NO 281
<211> LENGTH: 24
<212> TYPE: PRT
<213> ORGANISM: PRRS virus Type II

<400> SEQUENCE: 281

Gly Thr Asp Trp Leu Ala Gln Lys Phe Asp Trp Ala Val Glu Thr Phe
1               5                   10                  15

Val Ile Phe Pro Val Leu Thr His
20

<210> SEQ ID NO 282
<211> LENGTH: 23
<212> TYPE: PRT
<213> ORGANISM: PRRS virus Type II

<400> SEQUENCE: 282

Gly Ala Leu Thr Thr Ser His Phe Leu Asp Thr Val Gly Leu Ala Thr
1 5 10 15

Val Ser Thr Ala Gly Tyr Tyr
20

<210> SEQ ID NO 283
<211> LENGTH: 21
<212> TYPE: PRT
<213> ORGANISM: PRRS virus Type II

<400> SEQUENCE: 283

Ile Tyr Ala Val Cys Ala Leu Ala Ala Leu Ile Cys Phe Val Ile Arg
1 5 10 15

Leu Ala Lys Asn Cys
20

<210> SEQ ID NO 284
<211> LENGTH: 32
<212> TYPE: PRT
<213> ORGANISM: PRRS virus Type II

<400> SEQUENCE: 284

Val Ser Thr Ala Gly Tyr Tyr His Gly Arg Tyr Val Leu Ser Ser Ile
1 5 10 15

Tyr Ala Val Cys Ala Leu Ala Ala Leu Ile Cys Phe Val Ile Arg Leu
20 25 30

<210> SEQ ID NO 285
<211> LENGTH: 29
<212> TYPE: PRT
<213> ORGANISM: Artificial Sequence
<220> FEATURE:
<223> OTHER INFORMATION: SARS virus plus solubility tail GGEKEKEK

<400> SEQUENCE: 285

Ala Glu Val Gln Ile Asp Arg Leu Ile Thr Gly Arg Leu Gln Ser Leu
1 5 10 15

Gln Thr Tyr Val Cys Gly Gly Glu Lys Glu Lys Glu Lys
20 25

<210> SEQ ID NO 286
<211> LENGTH: 26
<212> TYPE: PRT
<213> ORGANISM: Artificial Sequence
<220> FEATURE:
<223> OTHER INFORMATION: SARS virus plus solubility tail GGEKEKEK

<400> SEQUENCE: 286

Gly Ala Ala Ile Gly Leu Ala Trp Ile Pro Tyr Phe Gly Pro Ala Ala
1 5 10 15

Glu Cys Gly Gly Glu Lys Glu Lys Glu Lys
20 25

```
<210> SEQ ID NO 287
<211> LENGTH: 25
<212> TYPE: PRT
<213> ORGANISM: Artificial Sequence
<220> FEATURE:
<223> OTHER INFORMATION: Influenza virus plus solubility tail GGEKEKEK

<400> SEQUENCE: 287

Gly Leu Phe Gly Ala Ile Ala Gly Phe Ile Glu Asn Gly Trp Glu Gly
1               5                   10                  15

Cys Gly Gly Glu Lys Glu Lys Glu Lys
            20                  25


<210> SEQ ID NO 288
<211> LENGTH: 23
<212> TYPE: DNA
<213> ORGANISM: Artificial sequence
<220> FEATURE:
<223> OTHER INFORMATION: IL-2 beta forward

<400> SEQUENCE: 288

gtggcaatga ggatgacttg ttc                                              23


<210> SEQ ID NO 289
<211> LENGTH: 22
<212> TYPE: DNA
<213> ORGANISM: Artificial sequence
<220> FEATURE:
<223> OTHER INFORMATION: IL-2 beta reverse

<400> SEQUENCE: 289

tagtggtggt cggagattcg ta                                               22


<210> SEQ ID NO 290
<211> LENGTH: 21
<212> TYPE: DNA
<213> ORGANISM: Artificial sequence
<220> FEATURE:
<223> OTHER INFORMATION: IL-6 forward

<400> SEQUENCE: 290

agccactcac ctcttcagaa c                                                21


<210> SEQ ID NO 291
<211> LENGTH: 21
<212> TYPE: DNA
<213> ORGANISM: Artificial sequence
<220> FEATURE:
<223> OTHER INFORMATION: IL-6 reverse

<400> SEQUENCE: 291

gcctctttgc tgctttcaca c                                                21


<210> SEQ ID NO 292
<211> LENGTH: 19
<212> TYPE: DNA
<213> ORGANISM: Artificial sequence
<220> FEATURE:
<223> OTHER INFORMATION: IL-10 forward

<400> SEQUENCE: 292

gtgatgcccc aagctgaga                                                   19


<210> SEQ ID NO 293
<211> LENGTH: 20
<212> TYPE: DNA
```

-continued

<213> ORGANISM: Artificial sequence
<220> FEATURE:
<223> OTHER INFORMATION: IL-10 reverse

<400> SEQUENCE: 293
cacggccttg ctcttgtttt 20

<210> SEQ ID NO 294
<211> LENGTH: 20
<212> TYPE: DNA
<213> ORGANISM: Artificial sequence
<220> FEATURE:
<223> OTHER INFORMATION: TNF-alpha forward

<400> SEQUENCE: 294
ctgctgcact ttggagtgat 20

<210> SEQ ID NO 295
<211> LENGTH: 20
<212> TYPE: DNA
<213> ORGANISM: Artificial sequence
<220> FEATURE:
<223> OTHER INFORMATION: TNF-alpha reverse

<400> SEQUENCE: 295
agatgatctg actgcctggg 20

<210> SEQ ID NO 296
<211> LENGTH: 18
<212> TYPE: DNA
<213> ORGANISM: Artificial sequence
<220> FEATURE:
<223> OTHER INFORMATION: NF-kappaB forward

<400> SEQUENCE: 296
tgagtcctgc tccttcca 18

<210> SEQ ID NO 297
<211> LENGTH: 18
<212> TYPE: DNA
<213> ORGANISM: Artificial sequence
<220> FEATURE:
<223> OTHER INFORMATION: NF-kappaB reverse

<400> SEQUENCE: 297
gcttcggtgt agcccatt 18

<210> SEQ ID NO 298
<211> LENGTH: 22
<212> TYPE: DNA
<213> ORGANISM: Artificial sequence
<220> FEATURE:
<223> OTHER INFORMATION: RPL13a forward

<400> SEQUENCE: 298
catcgtggct aaacaggtac tg 22

<210> SEQ ID NO 299
<211> LENGTH: 20
<212> TYPE: DNA
<213> ORGANISM: Artificial sequence
<220> FEATURE:
<223> OTHER INFORMATION: RPL13a reverse

<400> SEQUENCE: 299
gcacgacctt gagggcagca 20

-continued

```
<210> SEQ ID NO 300
<211> LENGTH: 20
<212> TYPE: DNA
<213> ORGANISM: Artificial sequence
<220> FEATURE:
<223> OTHER INFORMATION: RPL37A forward

<400> SEQUENCE: 300

attgaaatca gccagcacgc                                    20


<210> SEQ ID NO 301
<211> LENGTH: 21
<212> TYPE: DNA
<213> ORGANISM: Artificial sequence
<220> FEATURE:
<223> OTHER INFORMATION: RPL37A reverse

<400> SEQUENCE: 301

aggaaccaca gtgccagatc c                                  21
```